(12) United States Patent
Gold et al.

(10) Patent No.: US 12,414,934 B2
(45) Date of Patent: Sep. 16, 2025

(54) COMBINATION THERAPIES

(71) Applicants: Aardvark Therapeutics, Inc., San Diego, CA (US); The Spanish National Cancer Research Centre, Madrid (ES)

(72) Inventors: Daniel P. Gold, San Diego, CA (US); Miguel Quintela-Fandino, Madrid (ES)

(73) Assignees: Aardvark Therapeutics, Inc., San Diego, CA (US); The Spanish National Cancer Research Centre, Madrid (ES)

( * ) Notice: Subject to any disclaimer, the term of this patent is extended or adjusted under 35 U.S.C. 154(b) by 1075 days.

(21) Appl. No.: 17/202,755

(22) Filed: Mar. 16, 2021

(65) Prior Publication Data

US 2021/0267936 A1 Sep. 2, 2021

Related U.S. Application Data

(62) Division of application No. 15/546,900, filed as application No. PCT/US2016/016008 on Feb. 1, 2016, now Pat. No. 10,980,774.

(60) Provisional application No. 62/111,030, filed on Feb. 2, 2015.

(51) Int. Cl.

| | | |
|---|---|---|
| A61K 31/353 | (2006.01) |
| A61K 31/404 | (2006.01) |
| A61K 31/44 | (2006.01) |
| A61K 31/454 | (2006.01) |
| A61K 31/496 | (2006.01) |
| A61K 31/506 | (2006.01) |
| A61K 45/06 | (2006.01) |
| C07K 16/30 | (2006.01) |

(52) U.S. Cl.
CPC .......... *A61K 31/353* (2013.01); *A61K 31/404* (2013.01); *A61K 31/44* (2013.01); *A61K 31/454* (2013.01); *A61K 31/496* (2013.01); *A61K 31/506* (2013.01); *A61K 45/06* (2013.01); *C07K 16/30* (2013.01); *A61K 2300/00* (2013.01)

(58) Field of Classification Search
CPC .... A61K 31/353; A61K 31/404; A61K 31/44; A61K 31/454; A61K 31/496; A61K 31/506; A61K 45/06; C07K 16/30
USPC ........................................................ 514/456
See application file for complete search history.

(56) References Cited

U.S. PATENT DOCUMENTS

| | | |
|---|---|---|
| 3,340,276 A | 9/1967 | Carney et al. |
| 3,471,520 A | 10/1969 | Klaus et al. |
| 3,535,344 A | 10/1970 | Klaus et al. |
| 4,157,984 A | 6/1979 | Zilliken |
| 4,218,489 A | 8/1980 | Zilliken |
| 4,232,122 A | 11/1980 | Zilliken |
| 4,234,577 A | 11/1980 | Zilliken |
| 4,366,082 A | 12/1982 | Zilliken |
| 4,366,248 A | 12/1982 | Zilliken |
| 4,368,264 A | 1/1983 | Zilliken |
| 4,390,559 A | 6/1983 | Zilliken |
| 4,447,622 A | 5/1984 | Salman et al. |
| 4,644,012 A | 2/1987 | Tsuda et al. |
| 4,814,346 A | 3/1989 | Albert et al. |
| 5,024,998 A | 6/1991 | Bodor |
| 5,059,609 A | 10/1991 | Eggler et al. |
| 5,134,127 A | 7/1992 | Stella et al. |
| 5,280,040 A | 1/1994 | Labroo et al. |
| 5,376,645 A | 12/1994 | Stella et al. |
| 5,389,646 A | 2/1995 | Labroo |
| 5,464,862 A | 11/1995 | Labroo et al. |
| 5,696,149 A | 12/1997 | Korsgaard et al. |
| 5,726,202 A | 3/1998 | Shalmi et al. |
| 5,756,539 A | 5/1998 | Skrumsager et al. |
| 5,780,503 A | 7/1998 | Biftu et al. |
| 5,849,461 A | 12/1998 | Hatakeyama et al. |
| 5,874,418 A | 2/1999 | Stella et al. |
| 5,883,118 A | 3/1999 | Shalmi et al. |
| 5,919,817 A | 7/1999 | Jacobsen et al. |
| 5,958,967 A | 9/1999 | Jacobsen et al. |
| 5,985,306 A | 11/1999 | Jacobsen et al. |
| 5,994,390 A | 11/1999 | Jacobsen et al. |
| 5,998,451 A | 12/1999 | Eggler et al. |
| 6,005,003 A | 12/1999 | Nique |
| 6,043,269 A | 3/2000 | Jacobsen et al. |
| 6,316,494 B1 | 11/2001 | Jacobsen et al. |
| 6,479,467 B1 | 11/2002 | Buchanan et al. |
| 6,509,323 B1 | 1/2003 | Davis |
| 6,528,042 B1 | 3/2003 | Brown et al. |
| 6,610,671 B2 | 8/2003 | Buchanan et al. |
| 6,610,733 B2 | 8/2003 | Park et al. |
| 6,645,951 B1 | 11/2003 | Jo et al. |

(Continued)

FOREIGN PATENT DOCUMENTS

| | | |
|---|---|---|
| CA | 2581316 A1 | 3/2006 |
| CA | 2641541 A1 | 4/2010 |

(Continued)

OTHER PUBLICATIONS

Abegaz et al.: Isoflavonoids from the roots of Salsola somalensis. Phytochemistry. 30(4):1281-4, 1991 (Abstract Only in English).

Agarwal et al.: Isoflavones of two Iris species. Phytochemistry (Elsevier) 23(11):2703-4, 1984. (Abstract Only in English).

Agarwal et al.: Phenolic constituents of Iris Milesii rhizomes, Phytochemistry (Elsevier) 23(6):1342-3, 1984. (Abstract Only in English).

Aggarwal et al.: From chemoprevention to chemotherapy: common targets and common goals. Expert Opin. Investig. Drugs. 2004;13(10):1327-38.

(Continued)

*Primary Examiner* — Kahsay Habte
(74) *Attorney, Agent, or Firm* — McNeill PLLC

(57) ABSTRACT

Provided herein are methods of treating and sensitizing cancer comprising administering a glycolytic inhibitor and an oxidative phosphorylation inhibitor.

13 Claims, 6 Drawing Sheets

(56) References Cited

U.S. PATENT DOCUMENTS

| | | |
|---|---|---|
| 6,649,648 B1 | 11/2003 | Kelly et al. |
| 6,660,804 B1 | 12/2003 | Weltrowski et al. |
| 7,056,952 B1 | 6/2006 | Joannou |
| 7,202,273 B2 | 4/2007 | Kelly et al. |
| 7,601,855 B2 | 10/2009 | Heaton et al. |
| 7,906,554 B2 | 3/2011 | Kelly et al. |
| 8,080,675 B2 | 12/2011 | Heaton et al. |
| 8,084,628 B2 | 12/2011 | Heaton et al. |
| 8,163,795 B2 | 4/2012 | Heaton et al. |
| 8,461,361 B2 | 6/2013 | Heaton et al. |
| 8,697,891 B2 | 4/2014 | Heaton et al. |
| 8,957,109 B2 | 2/2015 | Heaton et al. |
| 9,138,478 B2 | 9/2015 | Heaton et al. |
| 9,198,895 B2 | 12/2015 | Heaton et al. |
| 9,381,186 B2 | 7/2016 | Heaton et al. |
| 9,663,484 B2 | 5/2017 | Jeoffreys et al. |
| 9,708,283 B2 | 7/2017 | Moreno |
| 9,981,936 B2 | 5/2018 | Moreno |
| 10,105,346 B2 | 10/2018 | Jeoffreys et al. |
| 10,369,132 B2 | 8/2019 | Moreno |
| 10,973,799 B2 | 4/2021 | Moreno |
| 10,980,774 B2 * | 4/2021 | Gold ............... A61K 31/496 |
| 11,723,893 B2 | 8/2023 | Moreno |
| 2002/0128468 A1 | 9/2002 | Buchanan et al. |
| 2004/0063663 A1 | 4/2004 | Buchanan et al. |
| 2004/0106575 A1 | 6/2004 | Zhang et al. |
| 2004/0109888 A1 | 6/2004 | Pun et al. |
| 2004/0209825 A1 | 10/2004 | Lahey et al. |
| 2006/0074126 A1 | 4/2006 | Heaton et al. |
| 2006/0074127 A1 | 4/2006 | Heaton et al. |
| 2006/0167037 A1 | 7/2006 | Kelly et al. |
| 2006/0167083 A1 | 7/2006 | Kelly |
| 2006/0183728 A1 | 8/2006 | Kelly et al. |
| 2007/0155695 A1 | 7/2007 | Wirth et al. |
| 2008/0014249 A1 | 1/2008 | Heaton et al. |
| 2008/0069900 A1 | 3/2008 | Kelly et al. |
| 2009/0317490 A1 | 12/2009 | Heaton et al. |
| 2010/0130598 A1 | 5/2010 | Brown et al. |
| 2010/0152284 A1 | 6/2010 | Brown et al. |
| 2010/0173983 A1 | 7/2010 | Brown et al. |
| 2012/0004296 A1 | 1/2012 | Heaton et al. |
| 2012/0039917 A1 | 2/2012 | Husband et al. |
| 2012/0114766 A1 | 5/2012 | Heaton et al. |
| 2012/0172424 A1 | 7/2012 | Heaton et al. |
| 2012/0251630 A1 | 10/2012 | Alvero et al. |
| 2014/0093498 A1 | 4/2014 | Gschwind et al. |
| 2014/0170243 A1 | 6/2014 | Heaton et al. |
| 2015/0238458 A1 | 8/2015 | Heaton et al. |
| 2015/0352074 A1 | 12/2015 | Heaton et al. |
| 2016/0136129 A1 | 5/2016 | Heaton et al. |
| 2016/0287555 A1 | 10/2016 | Heaton et al. |
| 2017/0246142 A1 | 8/2017 | Jeoffreys et al. |
| 2017/0342044 A1 | 11/2017 | Moreno |
| 2018/0015067 A1 | 1/2018 | Gold et al. |
| 2019/0142790 A1 | 5/2019 | Jeoffreys et al. |
| 2021/0000790 A1 | 1/2021 | Jeoffreys et al. |
| 2023/0145478 A1 | 5/2023 | Jeoffreys et al. |
| 2023/0372287 A1 | 11/2023 | Jeoffreys et al. |
| 2024/0165073 A1 | 5/2024 | Moreno |

FOREIGN PATENT DOCUMENTS

| | | |
|---|---|---|
| EP | 0267155 A2 | 5/1988 |
| EP | 0313295 A2 | 4/1989 |
| EP | 0470310 A1 | 2/1992 |
| EP | 0955286 A1 | 11/1999 |
| EP | 3253208 A1 | 12/2017 |
| GB | 1433013 A | 4/1976 |
| JP | 2000506507 A | 5/2000 |
| JP | 2001502706 A | 2/2001 |
| JP | 2001502711 A | 2/2001 |
| JP | 2002529372 A | 9/2002 |
| JP | 2003508526 A | 3/2003 |
| JP | 2005504796 A | 2/2005 |
| JP | 2005528391 A | 9/2005 |
| JP | 2006096734 A | 4/2006 |
| JP | 2008513376 A | 5/2008 |
| JP | 2012144537 A | 8/2012 |
| JP | 2013541563 A | 11/2013 |
| JP | 2014237638 A | 12/2014 |
| WO | WO-8002098 A1 | 10/1980 |
| WO | WO-9408986 A1 | 4/1994 |
| WO | WO-9420099 A1 | 9/1994 |
| WO | WO-9621442 A1 | 7/1996 |
| WO | WO-9621443 A1 | 7/1996 |
| WO | WO-9621444 A1 | 7/1996 |
| WO | WO-9622091 A1 | 7/1996 |
| WO | WO-9622092 A1 | 7/1996 |
| WO | WO-9622093 A1 | 7/1996 |
| WO | WO-9725035 A1 | 7/1997 |
| WO | WO-9725036 A1 | 7/1997 |
| WO | WO-9725037 A1 | 7/1997 |
| WO | WO-9725038 A1 | 7/1997 |
| WO | WO-9802154 A1 | 1/1998 |
| WO | WO-9802156 A1 | 1/1998 |
| WO | WO-9808503 A1 | 3/1998 |
| WO | WO-9817662 A1 | 4/1998 |
| WO | WO-9818770 A1 | 5/1998 |
| WO | WO-9818771 A1 | 5/1998 |
| WO | WO-9818772 A1 | 5/1998 |
| WO | WO-9818773 A1 | 5/1998 |
| WO | WO-9818774 A1 | 5/1998 |
| WO | WO-9818775 A1 | 5/1998 |
| WO | WO-9818776 A1 | 5/1998 |
| WO | WO-9818778 A1 | 5/1998 |
| WO | WO-9818779 A1 | 5/1998 |
| WO | WO-9825916 A1 | 6/1998 |
| WO | WO-9832437 A1 | 7/1998 |
| WO | WO-9833499 A1 | 8/1998 |
| WO | WO-9833500 A1 | 8/1998 |
| WO | WO-9936050 A1 | 7/1999 |
| WO | WO-9949862 A1 | 10/1999 |
| WO | WO-9955898 A1 | 11/1999 |
| WO | WO-9963974 A2 | 12/1999 |
| WO | WO-9965893 A1 | 12/1999 |
| WO | WO-0049009 A1 | 8/2000 |
| WO | WO-0066576 A1 | 11/2000 |
| WO | WO-0107031 A1 | 2/2001 |
| WO | WO-0117986 A1 | 3/2001 |
| WO | WO-0126651 A2 | 4/2001 |
| WO | WO-0154699 A1 | 8/2001 |
| WO | WO-0202548 A1 | 1/2002 |
| WO | WO-02059113 A1 | 8/2002 |
| WO | WO-03016270 A2 | 2/2003 |
| WO | WO-03035635 A1 | 5/2003 |
| WO | WO-03063859 A1 | 8/2003 |
| WO | WO-03086386 A1 | 10/2003 |
| WO | WO-2004030662 A1 | 4/2004 |
| WO | WO-2005049008 A1 | 6/2005 |
| WO | WO-2005049627 A1 | 6/2005 |
| WO | WO-2006032085 A1 | 3/2006 |
| WO | WO-2006032086 A1 | 3/2006 |
| WO | WO-2008052256 A1 | 5/2008 |
| WO | WO-2008113100 A1 | 9/2008 |
| WO | WO-2010022467 A1 | 3/2010 |
| WO | WO-2010045674 A1 | 4/2010 |
| WO | WO-2012061409 A1 | 5/2012 |
| WO | WO-2012061413 A2 | 5/2012 |
| WO | WO-2015117202 A1 | 8/2015 |
| WO | WO-2016126618 A1 | 8/2016 |

OTHER PUBLICATIONS

Akimoto et al.: Genistein, a tyrosine kinase inhibitor, enhanced radiosensitivity in human esophageal cancer cell lines in vitro: possible involvement of inhibition of survival signal transduction pathways. Int. J. Radiation Oncology Biol. Phys. 2001; 50(1):195-201.

ALDRICH Handbook of Fine Chemicals and Laboratory Equipment © 2002, Sigma-Aldrich Pty Limited, Australia: Note: Sigma-Aldrich is a US Company, catalogue/handbook from which the pages derive from is the AU publication.

(56) References Cited

OTHER PUBLICATIONS

Alvero AB, Brown D, Montagna M, Matthews M, Mor G. (2007) Phenoxodiol-Topotecan Co-5 Administration Exhibit Significant Anti-Tumor Activity Without Major Adverse Side Effects. Cancer Biol Ther. 6:612-7.

Alvero AB, Kelly M, Rossi P, Leiser A, Brown D, Rutherford T, Mor G. (2008) Anti-tumor activity of phenoxodiol: from bench to clinic. Future Oncol. 4(4):475-82.

Antus et al.: Synthesis of some pterocarpenes obtained from Brya ebenus, J. Chem. Soc., Perkin Trans. 6:1389-94, 1982 (Abstract Only in English).

Arnone et al.: Isoflavonoid constituents of the West African red wood, *Baphia nitida*. Phtyochemistry. 20(4):799-801, 1981. (Abstract Only in English).

Bartelink et al. The combined use of radiotherapy and chemotherapy in the treatment of solid tumours. Eur J Cancer 38(2):216-222 (2002).

Bellisarii et al.: Tumor necrosis factor-$\alpha$ and cardiovascular diseases. Ital Heart J. 2001;2(6):408-17.

Berge et al. Pharmaceutical Salts. Journal of Pharmaceutical Sciences 66(1):1-19 (Jan. 1977).

Berridge MV, Tan AS. (1998) Trans-plasma membrane electron transport a cellular assay for NADH- and NADPH-oxidase based on extracellular, superoxide-mediated reduction of the sulfonated tetrazolium salt WST-1. Protoplasma. 205:74-82.

Bundgaard. Design and Application of Prodrugs. Textbook of Drug Design and Development. Krosgaard-Larsen and Bundgaard. Chapter 5. pp. 113-191 (1991).

Bundgaard. Design of Prodrugs. Elsevier (12 pgs.) (1985).

Bundgaard. Means to Enhance Penetration: Prodrugs as a Means to Improve the Delivery of Peptide Drugs. Advanced Drug Delivery Review 8:1-38 (1992).

Bury et al.: Synthesis and pharmacological evaluation of novel cis-3,4-diaryl-hydroxychromanes as high affinity partial agonists for the estrogen receptor. Bioorg Med Chem. 2002;10:125-145.

Caltagirone et al.: Flavanoids apigenin and quercetin inhibit melanoma growth and metastatic potential. Int J Cancer Suppl. 87(4):595-600, 2002. (Abstract Only in English).

Caltagirone et al.: Interaction with type II estrogen binding sites and antiproliferative activity of tamoxifen and quercetin in human non-small-cell lung cancer, American Journal of Respiratory Cell and Molecular Biology. 17:(1):51-9, 1997. (Abstract Only in English).

Challa, et al. Cyclodextrins in drug delivery: an updated review. AAPS PharmSciTech. Oct. 14, 2005;6(2):E329-357. doi: 10.1208/pt060243.

Constantinou et al.: Phenoxodiol (2H-1-Benzopyran-7-0, 1, 3-(4-hydroxyphenyl), a Novel Isoflavone Derivative, Inhibits DNA Topoisomerase II by Stabilizing the Cleavable Complex. Anticancer Research. 2002;22:2581-86.

Constantinou et al.: Phenoxodiol, a novel isofavone derivative, inhibits dimethylbenz[a]anthracene(DMBA)-induced mammary carcinogenesis in female Sprague—Dawley rats. Eur J Cancer. 2003; 39:1012-18.

De Vincenzo et al.:Flavanoids and negative control of cell proliferation in ovarian tumors. Acta Medica Romana. 30(1-2):126-32, 1992. (Abstract Only in English).

Dorai, et al , Role of chemopreventive agents in cancer therapy. Cancer Lett. 215:129-40, 2004.

Ettmayer et al., Medicinal Chemistry, Lessons Learned from Marketed and Investigational Prodrugs, vol. 47, No. 10, pp. 2394-2404 (2004).

Fukui et al.: The synthesis of irisolone, Bull. Chem. Soc. Japan. 38(6):887-93, 1965 (Abstract Only in English).

Gamble et al.: Phenoxodiol, an experimental anticancer drug, shows potent antiangiogenic properties in addition to its antitumour effects. Int. J. Cancer. 118:2412-20, 2006.

Giacomelli et al., Silybin and its bioavailable, phospholipid complex(IdB 1016) potentiate in vitro and in vivo the activity of cisplatin. Life Sciences. Feb. 8, 2002; 70(12):1447-59 (Abstract Only in English).

Gokmen-Polar et al.: Gene Expression Analysis Reveals Distinct Pathways of Resistance to Bevacizumab in Xenograft Models of Human ER-Positive Breast Cancer. Journal of Cancer. 5(8):533-645 (2014).

Gupta et al., The use of Friedel-Crafts reactions for the synthesis of deoxybenzoins. Indian J Chem. 1968; 6(9):481-4 (Abstract Only in English).

Hem Chandra Jha et al.: Carbon-13-chemical shift assignments of chromones and isoflavones. Can J Chem. 58:1211-19, 1980.

Hersey et al.: How melanoma cells evade trail-induced apoptosis. Nat Rev Cancer. Nov. 2001; 1(2)142-50.

Horie et al.: Studies of the selective O-alkylation and dealkylation of flavonoids. XX. A convenient method for synthesizing 5,6,7-trihydroxyisoflavones and 5,6-dihydroxy-7-methoxyisoflavones. Pharm Bull. 44(3):486-91, 1996. (Abstract Only in English).

Hu et al., Identification of CYP1A2 as the main isoform for the Phase 1 hydroxylated metabolism of genistein and a prodrug converting exzyme of methylated isoflavones. Drug Metabolism and Dispostion, 31(7):924-931, 2003.

Caltagirone et al.: Flavonoids apigenin and quercetin inhibit melanoma growth and metastatic potential. Int. J. Can, 2000, 87(4), pp. 595-600.

Ito et al.: Isoflavonoids from Belamcanda chinensis. Pharm Bull. 49(9):1229-31, 2001 (Abstract Only in English).

Kakeji et al.: Preclinical studies of the combination of angiogenic inhibitors with cytotoxic agents. Invest New Drugs. 15:39-48, 1997.

Kamsteeg et al.: Phenoxodiol—an isoflavone analog-induces apoptosis in chemoresistant ovarian cancer cells. Oncogene. 22:2611-20, 2003.

Kang et al.: "Scientific Analysis of Formulation Theory of Chungpesagan-tang; In vitro Cytotoxicity of Cisplatin Combined with Chungpesagan-tang", Natural Product Sciences, vol. 6(4), pp. 165-169, 2000.

Kanzawa et al.: Evaluation of synergism by a novel three-dimensional model for the combined action of cisplatin and etoposide on the growth of a human small-cell lung-cancer cell line, SBC-3. Int. J. Cancer 71, 311-319, 1997.

Khoshyomn et al.: Synergistic Action of Genistein and Ciplatin on Growth Inhibition and Cytotoxicity of Human Medulloblastoma Cells. Pediatr Neurosurg. 33:123-31, 2000.

Kinjo et al.: Novel santalin analogs from *Pterpcarpus santalinus* (leguminosae): their biogenesis and anti-oxidative activities. Tennen Yuki Kagobutsu Toronkai Koen Yoshishu. 37:493-8, 1995. (Abstract Only in English).

Klus et al.: Formation of polyhydroxylated isoflavones from the soybean seed isoflavones daidzein and glycitein by bacteria isolated from tempe. Arch Microbiol. 164(6):428-34, 1995 (Abstract Only in English).

Kothari, et al. Inhibition of cholesterol ester transfer protein by CGS 25159 and changes in lipoproteins in hamsters: Atherosclerosis. (Shannon, Ireland) 128(1):59-66, 1997.

Kulling et al.: Oxidative metabolism of the soy isoflavones daidzein and genistein in humans in vitro and in vivo. J Agric Food Chem. 2001; 49(6):3024-33 (Abstract Only in English).

Lasithiotakis et al.: Combined Inhibition of MAPK and mTOR Signaling Inhibits Growth, Induces Cell Death, and Abrogates Invasive Growth of Melanoma Cells. The Society for Investigative Dermatology. vol. 128:2013-2023 (2008).

Lawson, Estrogenic activity of some derivatives of isoflaven and isoflavanol. J Chem Soc. 4448-50, 1954 (Abstract Only in English).

Lei et al.: Enhancement of Chemosensitivity and Programmed Cell death by Tyrosine Kinase Inhibitors Correlates with EGFR Expression in Non-Small Cell Lung Cancer Cells. Anticancer Res. 19:221-28, 1989.

Leslie, Science,vol. 327, 2010, p. 1573.

Li et al.: Apoptosis-Inducing Effect of Chemotherapeutic Agents Is Potentiated by Soy Isoflavone Genistein, a Natural Inhibitor of NF-KB in BxPC-3 Pancreatic Cancer Cell Line. Pancreas. (28)4:e90-5, 2004.

Mani et al.: Isoflavones. I. Bromination of isoflavones. J Inst Chem. 1974; 46(Pt.3):61-5 (Abstract Only in English).

(56) References Cited

OTHER PUBLICATIONS

Mani, et al, Isoflavones. III. Nitration of 7,8- and 6,7-dihydroxyisoflavones and their methyl ether. J Inst Chem. 1971; 43(6):234-40 (Abstract Only in English).
Mansour et al.: Enhancement of Chemotherapeutic Efficacy by Combining Agents that Block IL-10 in CLL Cell Lines. New Jersey Medical School, UMDNJ, Newark, NJ, USA Blood. Nov. 16, 2002; 100(11) Abstract No. 4997. Print (Abstract Only in English).
McDonnell et al.: Improvement in Efficacy of Chemoradiotherapy by Addition of and Antiangiogenic Agent in a Murine Tumor Model. J Surg Res. 2004; 116:19-23.
Micheli et al.: "Coumestro, Plant Phenolics, and Synthetic Estrogens: a Correlation of Structure and Activity", Journal of Medicinal and Pharmaceutical Chemistry, vol. 5, 1962, pp. 321-335.
Modified Cyclodextrins: Scaffolds and Templates for Supramolecular Chemistry (Eds. Christopher J. Easton, Stephen F. Lincoln, Imperial College Press, London, UK, 1999).
Montandon et al.: In-vitro versus in-vivo activities of new 5-lipoxygenase inhibitors with anti-inflammatory activity, Int J Tissue React. 1989; 11(3); 107-12 (Abstract Only in English).
Nakata et al., C225 Antiepidermal Growth Factor Receptor Antibody Enhances the Efficacy of Docetaxel Chemoradiotherapy. Int J Radiation Oncology Biol Phys. 2004; 59(4): 1163-73.
Navarro et al. Targeting Tumor Mitochondrial Metabolism Overcomes Resistance to Antiangiogenics. Cell Reports 15:2705-2718 (2016).
Nazir, et al. "Immunomodulatory Activity of Isoflavones Isolated from Iris Germananica (Iridacceae) on T-lymphocytes and Cytokines." Phytotherapy Research. 2009.
Neelam et al.: Combination of flavone acetic acid (FAA) with adriamycin, cis-platinum and diflouoromethylornithine (DFMO) in vitro against human colon cancer cells. Invest New Drugs. Aug. 1990; 8(3):263-8 (Abstract Only in English).
O'Dwyer et al.: Antitumor Activity and Biochemical Effects of Aphidicolin Glycinate(NSC 303812) Alone and in Combination with Cisplatin in Vivo. Cancer Res. Feb. 1, 1994; 54:724-29.
O'Neill et al.: Inducible Isoflavonoids from the Lima Bean, Phaseolus Lunatus. Phytochemistry. 1986; 25(6): 1315-22.
PCT/AU2005/001435 International Search Report dated Dec. 21, 2005.
PCT/AU2005/001436 International Search Report dated Dec. 21, 2005.
PCT/US2011/058815 International Preliminary Report on Patentability dated May 7, 2013.
PCT/US2011/058815 International Search Report and Written Opinion dated Mar. 12, 2012.
PCT/US2011/058820 International Preliminary Report on Patentability dated May 8, 2013.
PCT/US2011/058820 Search Report and Written Opinion dated Jun. 21, 2012.
PCT/US2016/016008 International Preliminary Report on Patentability dated Aug. 8, 2017.
PCT/US2016/016008 International Search Report and Written Opinion dated Apr. 19, 2016.
Piha-Paul et al.: Advanced gynecologic malignancies treated with a combination of the VEGF inhibitor bevacizumab and the mTOR inhibitor temsirolimus. Oncotarget. 5(7):1846-1855 (2014).
Portlock, et al. (Lymphoma research Foundation, getting the Facts, Mar. 2007).
Powles: A phase Ib study investigating the combination of everolimus and dovitinib in vascular endothelial grown factor refractory clear cell renal cancer. European Journal of Cancer. 50(12):2057-2064 (2014).
Rafi et al.: Modulation of bcl-2 and Cytotoxicity by Licochalcone-A, a Novel Estrogenic Flavonoid. Anticancer Res. 20:2653-58, 2000.
Ravindranath et al.: Anticancer Therapeutic Potential of Soy Isoflavone, Genistein. Complementary and Alternative Approaches to Biomedicine, edited by Edwin L. Cooper and Nobuo Yamaguchi. Kluwer Academic/Plenum Publishers. p. 121, 2004.

Registration No. 1157-39-7, 4H-1-Benzopyran-4-one, 7-methoxy-3-(4-methoxyphenyl)-methyl-(9CI), Nov. 16, 1984.
Registration No. 116703-40-3, 4H-1-Benzopyran-4-one, 2,3-dihydro-7,8-dimethoxy-3-(4-methoxyphenyl)-(9CI), Oct. 2, 1988.
Registration No. 116703-49-2, 4H-1-Benzopyran-4-one, 2,3-dihydro-7,8-dihydroxy-3-(4-methoxyphenyl)-(9CI), Oct. 2, 1988.
Registration No. 116718-51-5, 4H-1-Benzopyran-4-one, 7-hydroxy-3-(4-methoxyphenyl)-8-methyl-methyl-(9CI), Oct. 2, 1988.
Registration No. 124093-18-1, 4H-1-Benzopyran-4-one, 2,3-dihydro-7-hydroxy-3-(4-hydroxy-3-methoxyphenyl)-(9CI), Dec. 1, 1989.
Registration No. 129159-04-2, 4H-1-Benzopyran-4-one, 2,3-dihydro-3-(4-hydroxyphenyl)-(9CI), Aug. 31, 1990.
Registration No. 129159-05-3, 4H-1-Benzopyran-4-one, 3-(3,4-dihydroxyphenyl)-2,3-dihydro-(9CI), Aug. 31, 1990.
Registration No. 13139-86-1, Magnesium, bromo(4-methoxyphenyl)-(9CI), Nov. 16, 1984.
Registration No. 142050-44-0, 4H-1-Benzopyran-4-one, 7-hydroxy-3-[4-methoxy-3-(methoxy-t3)phenyl]-(9CI), Jun. 26, 1992.
Registration No. 143358-24-1, 4H-1-Benzopyran-4-one, 2,3-dihydro-7-methoxy-3-(4-methoxyphenyl)-(+)-(9CI), Sep. 9, 1992.
Registration No. 143358-39-8, 4H-1-Benzopyran-4-one, 2,3-dihydro-7-methoxy-3-(4-methoxyphenyl)-(-) (9CI), Sep. 9, 1992.
Registration No. 15236-11-0, 4H-1-Benzopyran-4-one, 2,3-dihydro-7-methoxy-3-(4-methoxyphenyl)-(9CI), Nov. 16, 1984.
Registration No. 16750-63-3, Magnesium, bromo(2-methoxyphenyl)-(9CI), Nov. 16, 1984.
Registration No. 201678-33-3, 4H-1-Benzopyran-4-one, 3-(3,4-dimethoxyphenyl)-2,3-dihydro-7,8-dimethoxy-(9CI), Feb. 22, 1998.
Registration No. 206257-38-7, 4H-1-Benzopyran-4-one, 2, 3-dihydro-3-(4-hydroxyphenyl)-7-methoxy-(9CI), Jun. 3, 1998.
Registration No. 24160-14-3, 4H-1-Benzopyran-4-one, 3-(3,4-dimethoxyphenyl)-7-hydroxy-(9CI), Nov. 16, 1984.
Registration No. 288267-24-3, 4H-1-Benzopyran-4-one, 7-hydroxy-3-(4-hydroxy-3-methoxyphenyl)-8-methyl-(9CI), Sep. 6, 2000.
Registration No. 304892-19-1, 4H-1-Benzopyran-4-one, 3-(3,4-dihydroxyphenyl)-2,3-dihydro-7-hydroxy-(9CI), Nov. 29, 2000.
Registration No. 36282-40-3, Magnesium, bromo(3-methoxyphenyl)-, Nov. 16, 1984.
Registration No. 39604-72-3, 4H-1-Benzopyran-4-one, 2,3-dihydro-7methoxy-3-(4-methoxyphenyl)-8-methyl-(9CI), Nov. 16, 1984.
Registration No. 4626-22-6, 4H-1-Benzopyran-4-one, 2,3-dihydro-7-hydroxy-3-(4-methoxyphenyl)-(9CI), Nov. 16, 1984.
Registration No. 67492-31-3, 4H-1-Benzopyran-4-one, 2,3-dihydro-7-hydroxy-3-(3-hydroxy-4-methoxyphenyl)-(9CI), Nov. 16, 1984.
Registration No. 680195-83-9, 4H-1-Benzopyran-4-one, 2,3-dihydro-7,8-dihydroxy-3-(4-hydroxyphenyl)-(9CI), May 6, 2004.
Registration No. 83206-83-1, 4H-1-Benzopyran-4-one, 3-(3,4-dimethoxyphenyl)-2,3-dihydro-7-hydroxy-(9CI), Nov. 16, 1984.
Registration No. 85915-64-6, 2H-1-Benzopyran-7-ol, 4-[5-(3,4-dihydro-7-hydroxy-2-H-1-benzopyran-3-yl)-4-hydroxy-2-methoxyphenyl]-3,4-dihydro-3-(2-hydroxy-4-methoxyphenyl)-,[3S-[3α-4β(R*)]]-(9CI), Nov. 16, 1984.
Registration No. 85915-66-8, 2H-1-Benzopyran, 4-[5-(3,4-dihydro-7-methoxy-2H-1-benzopyran-3-y1)-2,4-dimethoxyphenyl]-3-(2,4-dimethoxypheny1)-3,4-dihydro-7-methoxy-, [3S-[3α4β(R*)]]-(9CI), Nov. 16, 1984.
Registration No. 95307-73-6, 4H1-Benzopyran-4-one-2-d, 2,3-dihydro-2-d-7-hydroxy-3-(4-methoxyphenyl)-(9CI), Mar. 16, 1985.
Registration No. 95457-39-9, 4H-1-Benzopyran-4-one-4-14C, 3-(3,4-dimethoxyphenyl)-7-hydroxy-(9CI), Mar. 23, 1985.
Registration No. 95541-42-7, 1,3-Benzenediol, 4-[3,4-dihydro-3-(2-hydroxy-4-methoxyphenyl)-7-methoxy-2H-1-benzopyran-4-yl]-,(3R-trans)-(9CI), Mar. 30, 1985.
Registration No. 95541-43-8, 2H-Benzopyran, 3,4-bis(2,4-dimethoxyphenyl)-3,4-dihydro-7-methoxy-,(3R-trans)-(9CI), Mar. 30, 1985.
Registration No. 95541-44-9, 1,3,5-Benzenetriol,2-[3,4-dihydro-3-(2-hydroxy-4-methoxyphenyl)-7-methoxy-2H-1-benzopyran-4-yl)-,(3R-trans)-(9CI) (1984).
Registration No. 95541-45-0, 1,3,5-Benzenetriol,2,4-bis[3,4-dihydro-3-(2-hydroxy-4-methoxyphenyl)-7-methoxy-2H-1-benzopyran-4-yl]-,[3R-[3α,4β(3R*,4S"])-(9CI) (1984).

(56) References Cited

OTHER PUBLICATIONS

Registration No. 95541-46-1, 2H-1-Benzopyran,3-(2,4-dimethoxyphyenyl)-3,4-dihydro-7-methoxy-4(2,4,6-trimethoxyphenyl)-,(3R-trans)-(9CI) (1984).
Registration No. 95541-51-8, 2H-1-Benzopyran-7-ol,3-[3,4-dihydro-3-(2-hydroxy-4-methoxyphenyl)-7-methoxy-2H-1-benzopyran-4-yl]-2-hydroxy-4-methoxyphenyl]-3,4-dihydro-,[3R-3α,4β(S*)]-(9CI) (1984).
Registration No. 95541-53-0, 2H-1-Benzopyran,4-[5(3,4-dihyrdro-7-methoxy-2H-1-benzopyran-3-y1)-2,4-dimethoxyphenyl]-3-(2,4-dimethoxyphenyl)-3,4-dihydro-7-methoxy-,[3R-[3α,4β(S*)]]-(9CI) (1984).
Registration No. 95541-54-1, 2H-1-Benzopyran-7-ol,3-[-[4-dihydro-4-[4-hydroxy-5-(7-hydroxy-2H-1-benzopyran-3-y1)-2-methoxyphenyl]-3-(2-hydroxy-4-methon/phenyl)-(3S-trans)-(9CI) (1984).
Registration No. 95541-57-4, 2H-1-Benzopyran,4-[2,4-dimethoxy-5-(7-methoxy-2H-1-benzopyran-3-yl)phenyl]-3-(2,4-dimethoxyphenyl)-3,4-dihydro-7-methoxy-,(3S-trans)-(9CI) (1984).
Registration No. 95541-66-5, 2H-1-Benzopyran, 4-(2,4-dimethoxyphenyl)-3,4-dihydro-7-methoxy-3-[4-methoxy-2-(methoxymethoxy)phenyl]-,(3R-trans)-(9CI) (1984).
Registration No. 95762-78-0, 2H-1-Benzopyran,4,4'-(2,4,6-trimethoxy-1,3-phenylene)bix[3-(2,4-dimethoxyphenyl)-3,4-dihydro-7-methoxy-,[3R[3α,4β(3'R*,4'S*)]]-(9CI) (1984).
Scambia et al.: Antiproliferative effect of silybin on gynaecological malignancies; synergism with cisplatin and doxorubicin. Eur J Cancer. May 1996; 32A(5):877-82 (Abstract Only in English).
Scambia, G. Synergistic antiproliferative activity of quercetin and cisplatin on ovarian cancer cell growth. Anti-Cancer Drugs Oct. 1990; 1(1):45-8 (Abstract Only in English).
Sepulveda-Boza et al.: The preparation of new isoflavones, Synthetic Communications. 2001; 3(12):1933-40.
Stella, Expert Opinion on Therapeutic Patents, Prodrugs as therapeutics, vol. 14, No. 3, pp. 277-280 (2004).
Szlosarek et al.: Tumour necrosis factor a: a potential target for the therapy of solid tumours. The Lancet Oncology. Sep. 2003; 4:565-73.
Tamura et al.: Genistein Enhances the Cisplatin-Induced Inhibition of Cell Growth and Apoptosis in Human Malignant Melanoma Cells. Pigment Cell Res. 2003; 16:470-76 (Abstract Only in English).
Teo et al.: Synthesis of 3-(p-fluorophenyl)-4-arylchrom-3-enes as selective ligands for antiestrogen-binding sites. J Chem Res. Synopses. 1990; 1:4-5 (Abstract Only in English).
Teo et al.: Synthesis of arylchromenes and arylchromans. Bulletin of the Singapore National Institute of Chemistry. 1994; 22:69-74 (Abstract Only in English).
Therasse et al., New guidelines to evaluate the response to treatment in solid tumors. J. Natl. Cancer Inst., 92 (3): 205-216 (2000).
Therasse et al. New guidelines to evaluate the response to treatment in solid tumors: European Organization for Research and Treatment of Cancer, National Cancer Institute of the United States, National Cancer Institute of Canada. J Natl Cancer Inst 92:205-216 (2000).
Todorov et al.: Role of a proteolysis-inducing factor(PIF) in a cachexia induced by a human melanoma(G361). Br J Cancer. 1999; 80(11):1734-37.
Tubiana. The combination of radiotherapy and chemotherapy: a review. Int J Radiat Biol 55(4):497-511 (1989).
U.S. Appl. No. 14/186,940 Office Action mailed Nov. 21, 2014.
U.S. Appl. No. 11/230,726 Office Action dated Aug. 10, 2007.
U.S. Appl. No. 11/230,726 Office Action dated Jan. 22, 2007.
U.S. Appl. No. 11/230,726 Office Action dated Mar. 4, 2008.
U.S. Appl. No. 11/230,726 Office Action dated Oct. 28, 2008.
U.S. Appl. No. 12/551,277 Office Action dated Jan. 6, 2011.
U.S. Appl. No. 12/551,277 Office Action dated May 28, 2010.
U.S. Appl. No. 13/293,947 Office Action dated Jul. 20, 2012.
U.S. Appl. No. 13/293,947 Office Action dated May 24, 2013.
U.S. Appl. No. 13/293,947 Office Action dated Nov. 8, 2012.
U.S. Appl. No. 14/186,940 Office Action dated Aug. 6, 2014.
U.S. Appl. No. 13/891,975 Office Action dated Apr. 23, 2014.
U.S. Appl. No. 11/230,505 Office Action dated Dec. 17, 2009.
U.S. Appl. No. 11/230,505 Office Action dated Jun. 9, 2008.
U.S. Appl. No. 11/230,505 Office Action dated Mar. 12, 2009.
U.S. Appl. No. 11/230,505 Office Action dated Sep. 4, 2007.
"U.S. Appl. No. 13/061,112 Final Office Action mailed May 28, 2015".
U.S. Appl. No. 13/415,697 Office Action dated Jul. 6, 2012.
U.S. Appl. No. 13/881,599 Office Action dated Apr. 9, 2015.
U.S. Appl. No. 13/881,599 Office Action dated Aug. 18, 2016.
U.S. Appl. No. 13/881,599 Office Action dated Sep. 18, 2014.
U.S. Appl. No. 13/881,609 Office Action dated Apr. 10, 2015.
U.S. Appl. No. 13/881,609 Office Action dated Aug. 7, 2015.
U.S. Appl. No. 13/881,609 Office Action dated May 16, 2016.
U.S. Appl. No. 14/922,472 Office Action dated Sep. 26, 2016.
U.S. Appl. No. 15/175,386 Office Action dated May 10, 2018.
U.S. Appl. No. 15/175,386 Office Action dated Oct. 6, 2017.
U.S. Appl. No. 15/456,182 Office Action dated Nov. 20, 2017.
U.S. Appl. No. 15/546,900 Office Action dated Sep. 26, 2019.
U.S. Appl. No. 15/622,569 Office Action dated Sep. 7, 2017.
U.S. Appl. No. 15/961,259 Office Action dated Sep. 5, 2018.
U.S. Appl. No. 16/129,589 Final Office Action dated Nov. 7, 2019.
U.S. Appl. No. 16/129,589 Office Action dated Apr. 18, 2019.
U.S. Appl. No. 16/129,589 Office Action dated Mar. 19, 2020.
U.S. Appl. No. 16/444,981 Final Office Action dated Aug. 20, 2020.
U.S. Appl. No. 16/444,981 Office Action dated Mar. 3, 2020.
Varady, J. The flavonoids of Podocarpus spicatus. I. Structure of podospicatin. Synthesis of podospicatin mono-, di-, and trimethyl ethers. Periodica Polytech. 1963; 7(4):241-58 (Abstract Only in English).
Verma et al., Smooth Conversion of 3,4-Diarylcoumarins and 3,4,5-Triaryl-2(5H)-furanones to 2H-Chromene and 2,5-Dihydrofuran Derivatives with Dimethyl Sulfide-Borane Complex. Synthesis. 1988; 1:68-70.
Voss, C. et al., New isoflavonoids as inhibitors of porcine 5-lipoxygenase. Biochem Pharmacol. 1992; 44(1):157-62 (Abstract Only in English).
Waud et al.: Antitumor drug cross-resistance in vivo in a cisplatin-resistant murine P388 leukemia, Cancer Chemotherapy and Pharmacology. 1991; 27 (6):456-63 (Abstract Only in English).
Weidenborner et al.: Control of storage fungi of the genus *Aspergillus* on legumes with flavonoids and isoflavonoids. Angewandte Botanik. 1990: 64(1-2):175-90 (Abstract Only in English).
Widder et al. Section III: Prodrugs Kinetics. Method in Enzymology. 112:309-396 (1985).
Wolfbeis et al.: The Absorption and Fluorescence of Isoflavones and the Effect of Shift Reagents. Z Naturforsch. 39b:238-43, 1984.
Zyner et al.: Platinum(II) and palladium(II) N,0-Chelates with substituted flavanone containing ligangs. Acta Pol Pharm. 1999; 56(2): 159-67.
Zyner et al.: Pt(II) and Pt(II) complexes of 3-aminoflavone: In vitro and in vivo evaluation. Pharmazie. 1999; 54(12):945-46.
U.S. Appl. No. 17/023,681 Office Action dated Nov. 18, 2021.
U.S. Appl. No. 17/193,335 Office Action dated Sep. 15, 2022.
U.S. Appl. No. 18/340,308 Office Action dated Jul. 3, 2024.

* cited by examiner

COMBINATION THERAPIES

CROSS-REFERENCE TO RELATED APPLICATIONS

This application is a divisional of U.S. application Ser. No. 15/546,900, filed Jul. 27, 2017, which is a § 371 U.S. National Stage Entry of International Application No. PCT/US2016/016008, filed Feb. 1, 2016, which claims the benefit of U.S. Application Ser. No. 62/111,030, filed Feb. 2, 2015, which is hereby incorporated by reference in its entirety.

BACKGROUND OF THE INVENTION

Cancer is the leading cause of death worldwide.

SUMMARY OF THE INVENTION

Provided herein are pharmaceutical compositions, methods of treating disease, and kits. Provided in certain embodiments herein is a composition, wherein the composition comprises an oxidative phosphorylation inhibitor and a glycolytic inhibitor. In some embodiments, the composition further comprises a pharmaceutically acceptable excipient. In some embodiments, the composition comprises a liquid vehicle(s) to provide a physiologically acceptable formulation for parenteral administration. Also provided herein are combination therapies, comprising administration of an oxidative phosphorylation inhibitor and a glycolytic inhibitor to an individual in need thereof. In some embodiments, the oxidative phosphorylation inhibitor is a mitochondrial oxygenase inhibitor. In some embodiments, the oxidative phosphorylation inhibitor is a benzopyran derivative. In some embodiments, the combination therapy comprises administration of a benzopyran derivative and a glycolytic inhibitor. Some embodiments of the present invention provide a method for the treatment of cancer comprising administration of the composition to an individual in need of cancer therapy.

In some embodiments, the benzopyran derivative is a compound of Formula (II) or a pharmaceutically acceptable salt thereof:

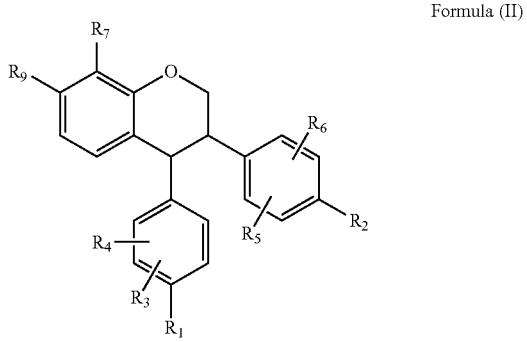

Formula (II)

wherein
$R_1$ is hydroxy, alkoxy, haloalkyl, or halo;
$R_2$ is hydroxy or alkoxy;
$R_3$, $R_4$, $R_5$, and $R_6$ are independently hydrogen, hydroxy, alkoxy, halo, haloalkyl, or alkyl;
$R_7$ is alkyl or hydrogen; and
$R_9$ is hydroxy or alkoxy.

Some embodiments provided herein describe a method of treating a disease or disorder associated with dysregulation of cell proliferation, comprising administering to a subject in need thereof an effective amount of:
(i) a glycolytic inhibitor; and
(ii) a compound of Formula (II) or a pharmaceutically acceptable salt thereof:

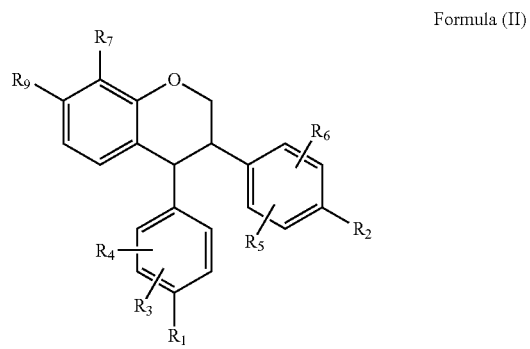

Formula (II)

wherein
$R_1$ is hydroxy, alkoxy, haloalkyl, or halo;
$R_2$ is hydroxy or alkoxy;
$R_3$, $R_4$, $R_5$, and $R_6$ are independently hydrogen, hydroxy, alkoxy, halo, haloalkyl, or alkyl;
$R_7$ is alkyl or hydrogen; and
$R_9$ is hydroxy or alkoxy.

In some embodiments, $R_1$ is hydroxy or alkoxy. In some embodiments, $R_2$ is hydroxy. In some embodiments, $R_3$, $R_4$, $R_5$, and $R_6$ are independently hydrogen or alkyl. In other embodiments, $R_3$, $R_4$, $R_5$, and $R_6$ are independently hydrogen. In some embodiments, $R_7$ is methyl or hydrogen.

In certain embodiments, $R_1$ is hydroxy or alkoxy; $R_2$ is hydroxy or alkoxy; $R_3$, $R_4$, $R_5$, and $R_6$ are independently hydrogen, hydroxy, alkoxy, or alkyl; $R_7$ is alkyl or hydrogen; and $R_9$ is hydroxy or alkoxy. In certain embodiments, $R_1$ is hydroxy or alkoxy; $R_2$ is hydroxy or alkoxy; $R_3$, $R_4$, $R_5$, and $R_6$ are independently hydrogen; $R_7$ is alkyl or hydrogen; and $R_9$ is hydroxy. In some embodiments, $R_1$ is hydroxy or methoxy; $R_2$ is hydroxy or methoxy; $R_3$, $R_4$, $R_5$, and $R_6$ are independently hydrogen, hydroxy, methoxy, methyl; $R_7$ is methyl or hydrogen; and $R_9$ is hydroxy or methoxy. In some embodiments, $R_1$ is hydroxy or methoxy; $R_2$ is hydroxy or methoxy; $R_3$, $R_4$, $R_5$, and $R_6$ are independently hydrogen; $R_7$ is methyl or hydrogen; and $R_9$ is hydroxy.

In some embodiments, the glycolytic inhibitor is a hexokinase inhibitor. In some instances, the hexokinase inhibitor is 2-deoxyglucose, 2-fluorodeoxyglucose, or 3-bromopyruvate.

In some embodiments, the glycolytic inhibitor is a glucose-6-phosphate dehydrogenase inhibitor. In some instances, the glucose-6-phosphate dehydrogenase inhibitor is red algal bromophenols.

In some embodiments, the glycolytic inhibitor is an angiogenesis inhibitor. In some instances, the angiogenesis inhibitor is nintedanib (BIBF 1120), bevacizumab (Avastin), everolimus (Afinitor), temsirolimus (Torisel), lenalidomide (Revlimid), pazopanib (Votrient), ramucirumab (Cyramza), sorafenib (Nexavar), sunitinib (Sutent), thalidomide (Thalomid), vandetanib (Caprelsa), cediranib (Recentin), axitinib (Inlyta), motesanib, vatalanib, dovitinib, brivanib, linifanib, tivozanib, lenvatinib, regorafenib (Stivarga), foretinib, telatinib, cabozantinib (Cometriq), nilotinib (Tasigna), tandutinib, imatinib (Gleevec), BMS-690514, quizartinib (AC220), orantinib, olaratumab, erlotinib (Tarceva), gefitinib (Iressa), afatinib (Gilotrif), lapatinib (Tykerb), varlitinib, AEE-788, trastuzumab (Herceptin), cetuximab (Erbitux), panitumumab (Vectibix), nimotuzumab, pertuzumab (Omnitarg), ertumaxomab, or zalutumumab. In some embodiments, the angiogenesis inhibitor is nintedanib (BIBF 1120), bevacizumab (Avastin), sorafenib (Nexavar), sunitinib (Sutent), thalidomide (Thalomid), or imatinib (Gleevec). In certain embodiments, the angiogenesis inhibitor is nintedanib (BIBF 1120).

In some embodiments, the disease or disorder to be treated is cancer. In some embodiments, the disease or disorder is breast cancer, colon cancer, prostate cancer, pancreatic cancer, leukemia, lymphoma, ovarian cancers, neuroblastoma, glioblastoma, kidney cancer, bladder cancer, gastrointestinal stromal tumors, liver cancer, head and neck cancer, lung cancer, melanoma, or a hematological malignancy. In certain embodiments, the disease or disorder is breast cancer. In certain embodiments, the cancer is refractory, non-responsive, or resistant to chemotherapy and/or haploidentical stem cell transplantation. In some embodiments, the cancer is non-responsive or resistant to the glycolytic inhibitor.

In some embodiments, the glycolytic inhibitor and compound of formula (II) are administered simultaneously or sequentially.

Other embodiments provided herein describe a method of treating chemoresistant cancer comprising administering to a subject in need thereof an effective amount of:
(i) a glycolytic inhibitor; and
(ii) a compound of Formula (II) or a pharmaceutically acceptable salt thereof:

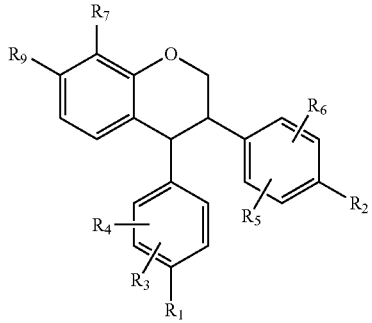

Formula (II)

wherein
$R_1$ is hydroxy, alkoxy, haloalkyl, or halo;
$R_2$ is hydroxy or alkoxy;
$R_3$, $R_4$, $R_5$, and $R_6$ are independently hydrogen, hydroxy, alkoxy, halo, haloalkyl, or alkyl;
$R_7$ is alkyl or hydrogen; and
$R_9$ is hydroxy or alkoxy.

In some embodiments, the chemoresistant cancer is breast cancer, colon cancer, prostate cancer, pancreatic cancer, leukemia, lymphoma, ovarian cancers, neuroblastoma, glioblastoma, kidney cancer, bladder cancer, gastrointestinal stromal tumors, liver cancer, head and neck cancer, lung cancer, melanoma, or a hematological malignancy. In some embodiments, the cancer is resistant to the glycolytic inhibitor. In certain embodiments, the glycolytic inhibitor is nintedanib (BIBF 1120).

Also provided herein, in some embodiments, is a method of killing cancer cells in a human, wherein the cancer cells include cancer cells that create ATP for energy anaerobically and cancer cells that aerobically generate ATP, the method comprising administering to a subject in need thereof an effective amount of:
(i) a glycolytic inhibitor; and
(ii) a compound of Formula (II) or a pharmaceutically acceptable salt thereof:

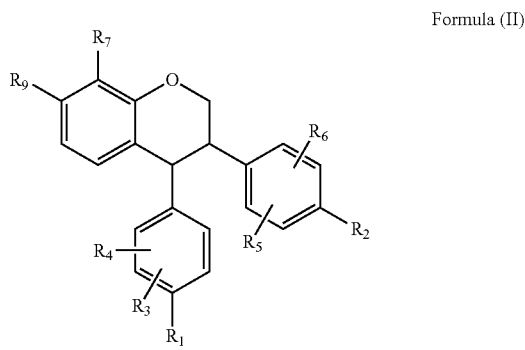

Formula (II)

wherein
$R_1$ is hydroxy, alkoxy, haloalkyl, or halo;
$R_2$ is hydroxy or alkoxy;
$R_3$, $R_4$, $R_5$, and $R_6$ are independently hydrogen, hydroxy, alkoxy, halo, haloalkyl, or alkyl;
$R_7$ is alkyl or hydrogen; and
$R_9$ is hydroxy or alkoxy.

Some embodiments provided herein describe a kit comprising one or more containers filled with a glycolytic inhibitor and one or more containers filled with a compound of Formula (II) or a pharmaceutically acceptable salt thereof:

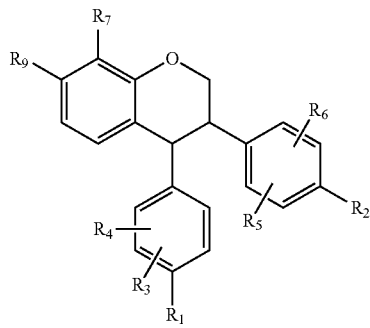

Formula (II)

wherein
$R_1$ is hydroxy, alkoxy, haloalkyl, or halo;
$R_2$ is hydroxy or alkoxy;
$R_3$, $R_4$, $R_5$, and $R_6$ are independently hydrogen, hydroxy, alkoxy, halo, haloalkyl, or alkyl;
$R_7$ is alkyl or hydrogen; and
$R_9$ is hydroxy or alkoxy.

DETAILED DESCRIPTION OF THE INVENTION

Figure 1:
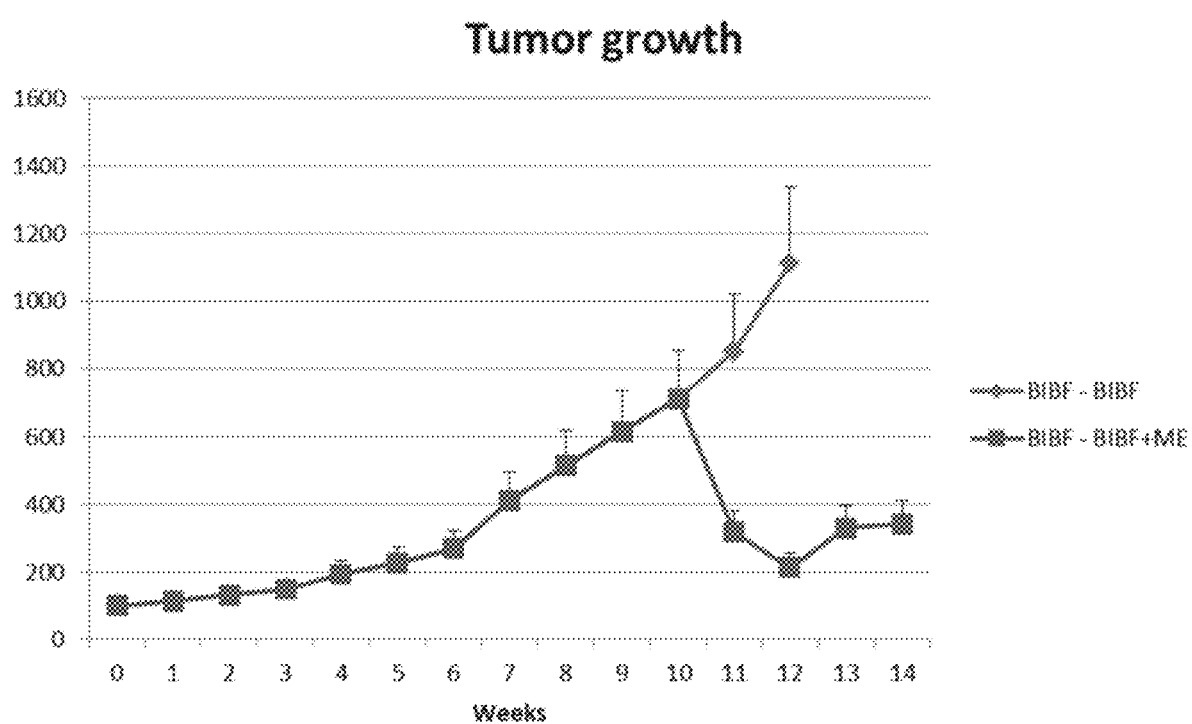
FIG. 1 depicts tumor growth in a mouse model of breast cancer with sequential treatment of nintedanib (BIBF) and compound 5 (ME).

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

There is a continuing need to develop and provide effective therapies for the treatment of cancer. Described herein are combination compositions and combination therapies for the treatment of cancer. The compositions and therapies described herein comprise a benzopyran derivative (e.g., substituted diaryl chroman derivatives and super-benzopyrans, such as Trilexium™ and Trx-1) and glycolytic inhibitors. Also provided herein are methods to induce apoptosis in a cancer cell, methods to treat cancer in individuals in need of cancer therapy, and methods to increase sensitivity of a cancer cell to a chemotherapeutic agent and/or radiation therapy (or to sensitize an individual to a particular chemotherapy).

Certain Definitions

Unless otherwise noted, terminology used herein should be given its normal meaning as understood by one of skill in the art.

The term "alkyl" as used herein, alone or in combination, refers to an optionally substituted straight-chain, or optionally substituted branched-chain saturated hydrocarbon monoradical having from one to about ten carbon atoms, more preferably one to six carbon atoms. Examples include, but are not limited to methyl, ethyl, n-propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, n-butyl, isobutyl, sec-butyl, t-butyl, n-pentyl, isopentyl, neopentyl, tert-amyl and hexyl, and longer alkyl groups, such as heptyl, octyl and the like. Whenever it appears herein, a numerical range such as "$C_1$-$C_6$ alkyl" or —$C_{1-6}$ alkyl, means that the alkyl group may consist of 1 carbon atom, 2 carbon atoms, 3 carbon atoms, 4 carbon atoms, 5 carbon atoms or 6 carbon atoms, although the present definition also covers the occurrence of the term "alkyl" where no numerical range is designated.

The terms "$C_1$-$C_3$-alkyl" and "$C_1$-$C_6$-alkyl" as used herein refer to saturated, straight- or branched-chain hydrocarbon radicals derived from a hydrocarbon moiety containing between one and three, one and six, and one and twelve carbon atoms, respectively, by removal of a single hydrogen atom. Examples of $C_1$-$C_3$-alkyl radicals include methyl, ethyl, propyl and isopropyl. Examples of $C_1$-$C_6$-alkyl radicals include, but are not limited to, methyl, ethyl, propyl, isopropyl, n-butyl, tert-butyl, neopentyl and n-hexyl.

The term "cycloalkyl" as used herein refers to a monovalent group derived from a monocyclic or bicyclic saturated carbocyclic ring compound containing between three and twenty carbon atoms by removal of a single hydrogen atom.

The term "$C_3$-$C_6$ cycloalkyl" denoted a monovalent group derived from a monocyclic or bicyclic saturated carbocyclic ring compound by removal of a single hydrogen atom. Examples include cyclopropyl, cyclobutyl, cyclopentyl, cyclohexyl.

The alkyl group or cycloalkyl group may optionally be substituted by one or more of fluorine, chlorine, bromine, iodine, carboxyl, $C_{1-4}$ alkoxycarbonyl, $C_{1-4}$ alkylaminocarbonyl, di-($C_{1-4}$ alkyl)-aminocarbonyl, hydroxyl, $C_{1-4}$ alkoxy, formyloxy, $C_{1-4}$ alkylcarbonyloxy, $C_{1-4}$ alkylthio, $C_{3-6}$ cycloalkyl or phenyl.

The term "alkoxy" as used herein, alone or in combination, refers to an alkyl ether radical, —O-alkyl, including the groups —O-aliphatic and —O-carbocyclyl, wherein the alkyl, aliphatic and carbocyclyl groups may be optionally substituted, and wherein the terms alkyl, aliphatic and carbocyclyl are as defined herein. Non-limiting examples of alkoxy radicals include methoxy, ethoxy, n-propoxy, iso-propoxy, n-butoxy, iso-butoxy, sec-butoxy, tert-butoxy and the like.

The terms "$C_1$-$C_3$-alkoxy", "$C_1$-$C_6$-alkoxy" as used herein refers to the $C_1$-$C_3$-alkyl group and $C_1$-$C_6$-alkyl group, as previously defined, attached to the parent molecular moiety through an oxygen atom. Examples of $C_1$-$C_6$-alkoxy radicals include, but are not limited to, methoxy, ethoxy, propoxy, isopropoxy, n-butoxy, tert-butoxy, neopentoxy and n-hexoxy.

The term "halo" and "halogen" as used herein refer to an atom selected from fluorine, chlorine, bromine and iodine.

The term "haloalkyl" includes "alkyl" wherein one or more such as 1, 2, 3, 4, or 5 of the hydrogens have been replaced by a halo atom. The haloalkyl may be straight chain or branched chain "alkyl" unit. Non-limiting examples include —$CH_2F$, —$CHF_2$, —$CF_3$, —$CH_2CH_2F$, —$CH_2CHF_2$, —$CH_2CF_3$, —$CF_2CH_2F$, —$CF_2CHF_2$, —$CF_2CF_3$, —$CH_2Cl$, —$CHCl_2$, —$CCl_3$, —$CH_2Br$, —$CHBr_2$, and —$CBr_3$.

The term "fluoroalkyl" includes "alkyl" wherein one or more such as 1, 2, 3, 4, or 5 of the hydrogens have been replaced by fluoro. The fluoroalkyl may be straight chain or branched chain "alkyl" unit. Preferred fluoroalkyl groups include trifluoromethyl and pentafluoroethyl.

The term "acceptable" with respect to a formulation, composition, or ingredient, as used herein, means having no persistent detrimental effect on the general health of the subject being treated.

The term "pharmaceutically acceptable", as used herein, refers to a material, including but not limited, to a salt, carrier or diluent, which does not abrogate the biological activity or properties of the compound, and is relatively nontoxic, i.e., the material may be administered to an individual without causing undesirable biological effects or interacting in a deleterious manner with any of the components of the composition in which it is contained.

The term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. For example, S. M. Berge, et al. describes pharmaceutically acceptable salts in detail in J. Pharmaceutical Sciences, 66: 1-19 (1977), incorporated herein by reference for this purpose. The salts are prepared in situ during the final isolation and purification of the compounds described herein, or separately by reacting the free base function with a suitable organic acid. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other documented methodologies such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxyethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate.

It should be understood that a reference to a salt includes the solvent addition forms or crystal forms thereof, particularly solvates or polymorphs. Solvates contain either stoichiometric or non-stoichiometric amounts of a solvent, and are often formed during the process of crystallization with pharmaceutically acceptable solvents such as water, ethanol, and the like. Hydrates are formed when the solvent is water, or alcoholates are formed when the solvent is alcohol. Polymorphs include the different crystal packing arrangements of the same elemental composition of a compound. Polymorphs usually have different X-ray diffraction patterns, infrared spectra, melting points, density, hardness, crystal shape, optical and electrical properties, stability, and solubility. Various factors such as the recrystallization solvent, rate of crystallization, and storage temperature may cause a single crystal form to dominate.

The term "cyclodextrin," as used herein, refers to cyclic carbohydrates consisting of at least six to eight sugar molecules in a ring formation. The outer part of the ring contains water soluble groups; at the center of the ring is a relatively nonpolar cavity able to accommodate small molecules.

The terms "administer," "administering," "administration," and the like, as used herein, refer to the methods that may be used to enable delivery of compounds or compositions to the desired site of biological action. These methods include, but are not limited to oral routes, intraduodenal routes, parenteral injection (including intravenous, subcutaneous, intraperitoneal, intramuscular, intravascular or infusion), topical and rectal administration. Those of skill in the art are familiar with administration techniques that can be employed with the compounds and methods described herein. In some embodiments, the compounds and compositions described herein are administered orally.

The terms "co-administration" or the like, as used herein, are meant to encompass administration of the selected therapeutic agents to a single patient, and are intended to include treatment regimens in which the agents are administered by the same or different route of administration or at the same or different time.

The term "effective amount," as used herein, refers to a sufficient amount of an agent or a compound being administered which will relieve to some extent one or more of the symptoms of the disease or condition being treated. The result can be reduction and/or alleviation of the signs, symptoms, or causes of a disease, or any other desired alteration of a biological system. An appropriate "effective" amount in any individual case may be determined using techniques, such as a dose escalation study.

The term "pharmaceutical combination" as used herein, means a product that results from the mixing or combining of more than one active ingredient and includes both fixed and non-fixed combinations of the active ingredients. The term "fixed combination" means that the active ingredients, e.g. a compound described herein, or a pharmaceutically acceptable salt thereof, and a co-agent, are both administered to a patient simultaneously in the form of a single entity or dosage. The term "non-fixed combination" means that the active ingredients, e.g. a compound described herein, or a pharmaceutically acceptable salt thereof, and a co-agent, are administered to a patient as separate entities either simultaneously, concurrently or sequentially with no specific intervening time limits, wherein such administration provides effective levels of the two compounds in the body of the patient. The latter also applies to cocktail therapy, e.g. the administration of three or more active ingredients.

The term "patient", "subject" or "individual" are used interchangeably. As used herein, they refer to individuals suffering from a disorder, and the like, encompasses mammals and non-mammals. None of the terms require that the individual be under the care and/or supervision of a medical professional. Mammals are any member of the Mammalian class, including but not limited to humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish and the like. In some embodiments of the methods and compositions provided herein, the individual is a mammal. In preferred embodiments, the individual is a human.

The terms "treat", "treating" or "treatment", as used herein, include alleviating, abating or ameliorating a disease or condition or one or more symptoms thereof, preventing additional symptoms, ameliorating or preventing the underlying metabolic causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition, and are intended to include prophylaxis. The terms further include achieving a therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the individual, notwithstanding that the individual is still be afflicted with the underlying disorder. For prophylactic benefit, the compositions are administered to an individual at risk of developing a particular disease, or to an individual reporting one or more of the physiological symptoms of a disease, even though a diagnosis of this disease has not been made.

The terms "preventing" or "prevention" refer to a reduction in risk of acquiring a disease or disorder (i.e., causing at least one of the clinical symptoms of the disease not to develop in a subject that may be exposed to or predisposed to the disease but does not yet experience or display symptoms of the disease).

The term "carrier" as used herein, refers to relatively nontoxic chemical compounds or agents that facilitate the incorporation of a compound into cells or tissues.

A dosage of an oxidative phosphorylation inhibitor or a glycolytic inhibitor may be expressed in absolute or relative terms. For example, a dosage of either an oxidative phosphorylation inhibitor or a glycolytic inhibitor may be expressed as a certain number of milligrams (mg) of an oxidative phosphorylation inhibitor or a glycolytic inhibitor, or a pharmaceutically acceptable salt thereof, administered to a patient. In relative terms, a dosage of an oxidative phosphorylation inhibitor or a glycolytic inhibitor herein may be expressed as "mg/kg," which expresses the number of milligrams the oxidative phosphorylation inhibitor or glycolytic inhibitor, or pharmaceutically acceptable salt thereof, administered to a patient per kg of the patient's body weight. Dosage may also be expressed in terms of mg/m², indicating the mass of active ingredient administered per square meter of the patient's estimated surface area.

Benzopyran Derivative Compounds

Some embodiments of the present invention describe benzopyran derivatives. In some embodiments, the benzopyran derivative is a substituted diaryl chroman derivative, super-benzopyrans, or a combination thereof.

In some embodiments, the benzopyran derivative has the structure of Formula (I):

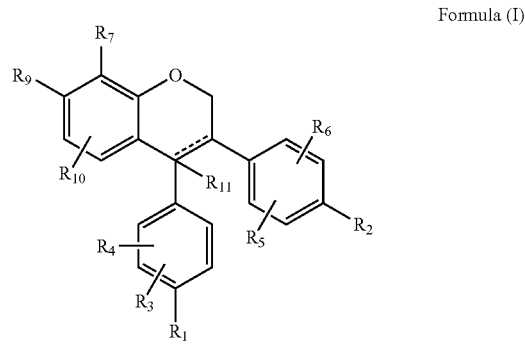

Formula (I)

wherein $R_1$ is hydrogen, hydroxy, halo, $NR_{14}R_{15}$, $C_{3-6}$cycloalkyl, $C_{1-6}$alkoxy, $C_{1-6}$haloalkyl, $C_{2-6}$alkenyl, $COOR_{12}$, $COR_{13}$, $(O)_nC_{1-4}$alkyleneNR$_{14}R_{15}$ or $C_{1-6}$alkyl optionally substituted by one or more hydroxy, chloro, bromo, iodo or $NR_{14}R_{15}$ groups;

$R_2$, $R_3$, $R_4$, $R_5$, $R_6$, $R_9$, and $R_{10}$ are independently hydrogen, hydroxy, halo, $NR_{14}R_{15}$, $C_{3-6}$cycloalkyl, $C_{1-6}$alkoxy, $C_{1-6}$haloalkyl, $C_{2-6}$alkenyl, $COOR_{12}$, $COR_{13}$, or $C_{1-6}$alkyl optionally substituted by one or more hydroxy, chloro, bromo, iodo or $NR_{14}R_{15}$ groups;

$R_7$ is hydrogen, hydroxy, halo, $NR_{14}R_{15}$, $C_{3-6}$cycloalkyl, $C_{1-6}$alkoxy, $C_{2-6}$alkenyl, $C_{1-6}$haloalkyl or $C_{1-6}$alkyl optionally substituted by one or more hydroxy, chloro, bromo, iodo or $NR_{14}R_{15}$ groups;

the drawing ==== and $R_2$ together represent a double bond or the drawing ==== represents a single bond and $R_{11}$ is hydrogen, hydroxy, $NR_{14}R_{15}$, $C_{1-3}$alkoxy, $C_{1-3}$fluoroalkyl, halo or $C_{1-3}$alkyl optionally substituted by one or more hydroxy, chloro, bromo, iodo or $NR_{14}R_{15}$ groups;

$R_{11}$ and $R_{12}$ are independently hydrogen, $C_{1-6}$alkyl, $C_{3-6}$cycloalkyl, or trialkyl silyl;

$R_{13}$ is hydrogen, $C_{1-6}$alkyl, $C_{3-6}$cycloalkyl or $NR_{14}R_{15}$;

n represents 0 or 1; and $R_{14}$ and $R_{15}$ independently represent hydrogen or $C_{1-6}$alkyl or $NR_{14}R_{15}$ when taken together represents a 5 or 6 membered heteroaromatic or heterocyclic, or a pharmaceutically acceptable salt thereof.

Some embodiments of the present invention describe a benzopyran derivative having the structure of Formula (II):

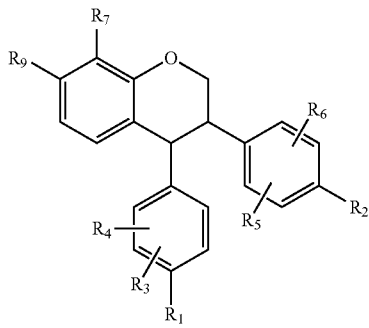

Formula (II)

$R_1$ is hydroxy, alkoxy, haloalkyl, or halo;
$R_2$ is hydroxy or alkoxy;
$R_3$, $R_4$, $R_5$, and $R_6$ are independently hydrogen, hydroxy, alkoxy, halo, haloalkyl, or alkyl and
$R_7$ is alkyl or hydrogen; and
$R_9$ is hydroxy or alkoxy;
or a pharmaceutically acceptable salt thereof.

In some embodiments, $R_1$ is hydroxy or alkoxy. In some embodiments, $R_1$ is hydroxy. In other embodiments, $R_1$ is $C_1$-$C_6$alkoxy. In further or additional embodiments, $R_1$ is $C_1$-$C_3$alkoxy. In other embodiments, $R_1$ is $C_1$-$C_2$alkoxy. In specific embodiments, $R_1$ is methoxy. In specific embodiments, $R_1$ is ethoxy. In specific embodiments, $R_1$ is propoxy. In specific embodiments, $R_1$ is iso-propoxy. In specific embodiments, $R_1$ is butoxy. In specific embodiments, $R_1$ is iso-butoxy. In specific embodiments, $R_1$ is sec-butoxy. In specific embodiments, $R_1$ is tert-butoxy. In specific embodiments, $R_1$ is pentyloxy. In specific embodiments, $R_1$ is hexyloxy. In further or alternative embodiments, $R_1$ is fluoro. In other embodiments, $R_1$ is chloro. In other embodiments, $R_1$ is iodo. In other embodiments, $R_1$ is bromo. In other embodiments, $R_1$ is haloalkyl. In other embodiments, $R_1$ is halo$C_{1-6}$alkyl. In other embodiments, $R_1$ is halo$C_{1-3}$alkyl. In other embodiments, $R_1$ is halo$C_{1-2}$alkyl. In specific embodiments, $R_1$ is monofluoromethyl. In specific embodiments, $R_1$ is difluoromethyl. In specific embodiments, $R_1$ is trifluoromethyl.

In some embodiments, $R_2$ is hydroxy. In some embodiments, $R_2$ is $C_1$-$C_6$alkoxy. In further or additional embodiments, $R_2$ is $C_1$-$C_3$alkoxy. In further or additional embodiments, $R_2$ is $C_1$-$C_2$alkoxy. In specific embodiments, $R_2$ is methoxy. In specific embodiments, $R_2$ is ethoxy. In specific embodiments, $R_2$ is propoxy. In specific embodiments, $R_2$ is iso-propoxy. In specific embodiments, $R_2$ is butoxy. In specific embodiments, $R_2$ is iso-butoxy. In specific embodiments, $R_2$ is sec-butoxy. In specific embodiments, $R_2$ is tert-butoxy. In specific embodiments, $R_2$ is pentyloxy. In specific embodiments, $R_2$ is hexyloxy.

In some embodiments, $R_3$, $R_4$, $R_5$, and $R_6$ are independently hydrogen, alkoxy, or alkyl. In some embodiments, $R_3$, $R_4$, $R_5$, and $R_6$ are independently hydrogen or alkyl. In other embodiments, $R_3$, $R_4$, $R_5$, and $R_6$ are independently hydrogen.

In some embodiments, $R_3$ is hydrogen. In some embodiments, $R_3$ is $C_1$-$C_6$alkyl. In other embodiments, $R_3$ is $C_1$-$C_3$alkyl. In other embodiments, $R_3$ is $C_1$-$C_2$alkyl. In specific embodiments, $R_3$ is methyl. In specific embodiments, $R_3$ is ethyl. In specific embodiments, $R_3$ is propyl. In specific embodiments, $R_3$ is iso-propyl. In specific embodiments, $R_3$ is butyl. In specific embodiments, $R_3$ is iso-butyl. In specific embodiments, $R_3$ is sec-butyl. In specific embodiments, $R_3$ is tert-butyl. In specific embodiments, $R_3$ is pentyl. In specific embodiments, $R_3$ is hexyl. In some embodiments, $R_3$ is $C_1$-$C_6$alkoxy. In further or additional embodiments, $R_3$ is $C_1$-$C_3$alkoxy. In further or additional embodiments, $R_3$ is $C_1$-$C_2$alkoxy. In specific embodiments, $R_3$ is methoxy. In specific embodiments, $R_3$ is ethoxy. In specific embodiments, $R_3$ is propoxy. In further or alternative embodiments, $R_3$ is fluoro. In other embodiments, $R_3$ is chloro. In other embodiments, $R_3$ is iodo. In other embodiments, $R_3$ is bromo. In other embodiments, $R_3$ is haloalkyl. In other embodiments, $R_3$ is halo$C_{1-6}$alkyl. In other embodiments, $R_3$ is halo$C_{1-3}$alkyl. In other embodiments, $R_3$ is halo$C_{1-2}$alkyl. In specific embodiments, $R_3$ is monofluoromethyl. In specific embodiments, $R_3$ is difluoromethyl. In specific embodiments, $R_3$ is trifluoromethyl.

In some embodiments, $R_4$ is hydrogen. In some embodiments, $R_4$ is $C_1$-$C_6$alkyl. In other embodiments, $R_4$ is $C_1$-$C_3$alkyl. In other embodiments, $R_4$ is $C_1$-$C_2$alkyl. In specific embodiments, $R_4$ is methyl. In specific embodiments, $R_4$ is ethyl. In specific embodiments, $R_4$ is propyl. In specific embodiments, $R_4$ is iso-propyl. In specific embodiments, $R_4$ is butyl. In specific embodiments, $R_4$ is iso-butyl. In specific embodiments, $R_4$ is sec-butyl. In specific embodiments, $R_4$ is tert-butyl. In specific embodiments, $R_4$ is pentyl. In specific embodiments, $R_4$ is hexyl. In some embodiments, $R_4$ is $C_1$-$C_6$alkoxy. In further or additional embodiments, $R_4$ is $C_1$-$C_3$alkoxy. In further or additional embodiments, $R_4$ is $C_1$-$C_2$alkoxy. In specific embodiments, $R_4$ is methoxy. In specific embodiments, $R_4$ is ethoxy. In specific embodiments. $R_4$ is propoxy. In further or alternative embodiments, $R_4$ is fluoro. In other embodiments, $R_4$ is chloro. In other embodiments, $R_4$ is iodo. In other embodiments, $R_4$ is bromo. In other embodiments, $R_4$ is haloalkyl. In other embodiments, $R_4$ is halo$C_{1-6}$alkyl. In other embodiments, $R_4$ is halo$C_{1-3}$alkyl. In other embodiments, $R_4$ is halo$C_{1-2}$alkyl. In specific embodiments, $R_4$ is monofluoromethyl. In specific embodiments, $R_4$ is difluoromethyl. In specific embodiments, $R_4$ is trifluoromethyl.

In some embodiments, $R_5$ is hydrogen. In some embodiments, $R_5$ is $C_1$-$C_6$alkyl. In other embodiments, $R_5$ is $C_1$-$C_3$alkyl. In other embodiments, $R_5$ is $C_1$-$C_2$alkyl. In specific embodiments, $R_5$ is methyl. In specific embodiments, $R_5$ is ethyl. In specific embodiments, $R_5$ is propyl. In specific embodiments, $R_5$ is iso-propyl. In specific embodiments, $R_5$ is butyl. In specific embodiments, $R_5$ is iso-butyl. In specific embodiments, $R_5$ is sec-butyl. In specific embodiments, $R_5$, is tert-butyl. In specific embodiments, $R_5$ is pentyl. In specific embodiments, $R_5$ is hexyl. In some embodiments, $R_5$ is $C_1$-$C_6$alkoxy. In further or additional embodiments, $R_5$ is $C_1$-$C_3$alkoxy. In further or additional embodiments, $R_5$ is $C_1$-$C_2$alkoxy. In specific embodiments, $R_5$ is methoxy. In specific embodiments, $R_5$ is ethoxy. In specific embodiments, $R_5$ is propoxy. In further or alternative embodiments, $R_5$ is fluoro. In other embodiments, $R_5$ is chloro. In other embodiments, $R_5$ is iodo. In other embodiments, $R_5$ is bromo. In other embodiments, $R_5$ is haloalkyl. In other embodiments, $R_5$ is halo$C_{1-6}$alkyl. In other embodiments, $R_5$ is halo$C_{1-3}$alkyl. In other embodiments, $R_5$ is halo$C_{1-2}$alkyl. In specific embodiments, $R_5$ is monofluoromethyl. In specific embodiments, $R_5$ is difluoromethyl. In specific embodiments, $R_5$ is trifluoromethyl.

In some embodiments, $R_6$ is hydrogen. In some embodiments, $R_6$ is $C_1$-$C_6$alkyl. In other embodiments, $R_6$ is $C_1$-$C_3$alkyl. In other embodiments, $R_6$ is $C_1$-$C_2$alkyl. In specific embodiments, $R_6$ is methyl. In specific embodiments, $R_6$ is ethyl. In specific embodiments, $R_6$ is propyl. In specific embodiments, $R_6$ is iso-propyl. In specific embodiments, $R_6$ is butyl. In specific embodiments, $R_6$ is iso-butyl. In specific embodiments, $R_6$ is sec-butyl. In specific embodiments, $R_6$ is tert-butyl. In specific embodiments, $R_6$ is pentyl. In specific embodiments, $R_6$ is hexyl. In some embodiments, $R_6$ is $C_1$-$C_6$alkoxy. In further or additional embodiments, $R_6$ is $C_1$-$C_3$alkoxy. In further or additional embodiments, $R_6$ is $C_1$-$C_2$alkoxy. In specific embodiments, $R_6$ is methoxy. In specific embodiments, $R_6$ is ethoxy. In specific embodiments, $R_6$ is propoxy. In further or alternative embodiments, $R_6$ is fluoro. In other embodiments, $R_6$ is chloro. In other embodiments, $R_6$ is iodo. In other embodiments, $R_6$ is bromo. In other embodiments, $R_6$ is haloalkyl. In other embodiments, $R_6$ is halo$C_{1-6}$alkyl. In other embodiments, $R_6$ is halo$C_{1-3}$alkyl. In other embodiments, $R_6$ is halo$C_{1-2}$alkyl. In specific embodiments, $R_6$ is monofluoromethyl. In specific embodiments, $R_6$ is difluoromethyl. In specific embodiments, $R_6$ is trifluoromethyl.

In some embodiments, $R_7$ is $C_1$-$C_6$alkyl. In other embodiments, $R_7$ is $C_1$-$C_3$alkyl. In other embodiments, $R_7$ is $C_1$-$C_2$alkyl. In specific embodiments, $R_7$ is methyl. In specific embodiments, $R_7$ is ethyl. In specific embodiments, $R_7$ is propyl. In specific embodiments, $R_7$ is isopropyl. In alternative embodiments, $R_7$ is hydrogen. In some embodiments, $R_7$ is methyl or hydrogen.

In some embodiments, $R_9$ is hydroxy. In some embodiments, $R_9$ is $C_1$-$C_6$alkoxy. In further or additional embodiments, $R_9$ is $C_1$-$C_3$alkoxy. In further or additional embodiments, $R_9$ is $C_1$-$C_2$alkoxy. In specific embodiments, $R_9$ is methoxy. In specific embodiments, $R_9$ is ethoxy. In specific embodiments, $R_9$ is propoxy. In specific embodiments, $R_9$ is iso-propoxy. In specific embodiments, $R_9$ is butoxy. In specific embodiments, $R_9$ is iso-butoxy. In specific embodiments, $R_9$ is sec-butoxy. In specific embodiments, $R_9$ is tert-butoxy. In specific embodiments, $R_9$ is pentyloxy. In specific embodiments, $R_9$ is hexyloxy.

In certain embodiments, $R_1$ is hydroxy or alkoxy; $R_2$ is hydroxy or alkoxy; $R_3$, $R_4$, $R_5$, and $R_6$ are independently hydrogen, hydroxy, alkoxy, or alkyl; $R_7$ is alkyl or hydrogen; and $R_9$ is hydroxy or alkoxy.

In certain embodiments, $R_1$ is hydroxy or alkoxy; $R_2$ is hydroxy or alkoxy; $R_3$, $R_4$, $R_5$, and $R_6$ are independently hydrogen; $R_7$ is alkyl or hydrogen; and $R_9$ is hydroxy.

In some embodiments, $R_1$ is hydroxy or methoxy; $R_2$ is hydroxy or methoxy; $R_3$, $R_4$, $R_5$, and $R_6$ are independently hydrogen, hydroxy, methoxy, methyl, $R_7$ is methyl or hydrogen; and $R_9$ is hydroxy or methoxy.

In some embodiments, $R_1$ is hydroxy or methoxy; $R_2$ is hydroxy or methoxy; $R_3$, $R_4$, $R_5$, and $R_6$ are independently hydrogen; $R_7$ is methyl or hydrogen; and $R_9$ is hydroxy.

In some embodiments, compounds of the general Formula (II) have the substituents $R_1$, $R_3$, and $R_4$ distributed as shown below:

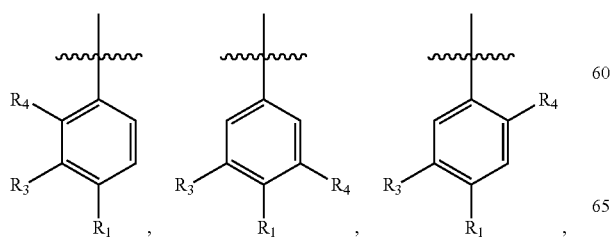

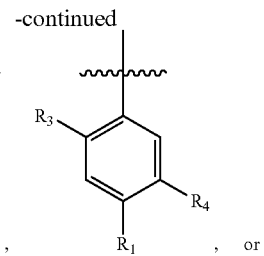

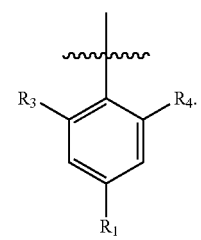

In some embodiments, compounds of the general Formula (II) have the substituents $R_2$, $R_5$, and $R_6$ distributed as shown below:

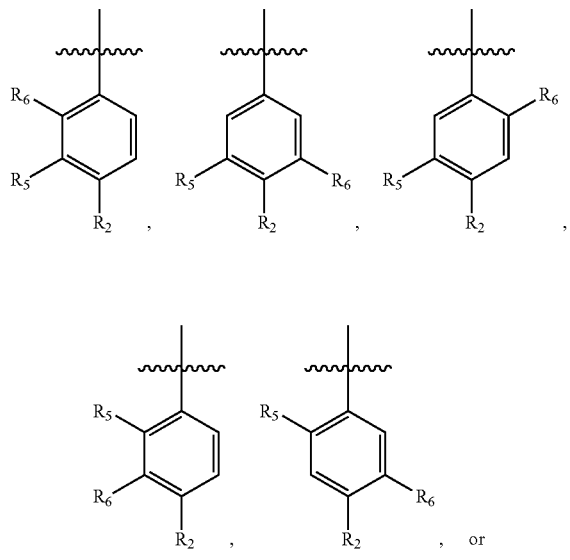

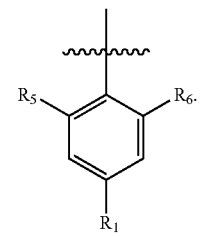

Some embodiments provided herein describe a compound of Formula (II) that has a structure of Formula (III-a) or (III-b):

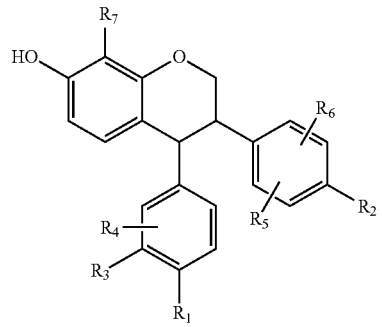

Formula (III-a)

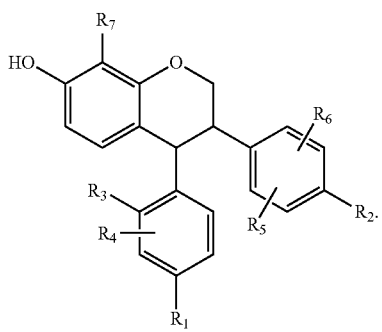

Formula (III-b)

Some embodiments provided herein describe a compound of Formula (II) that has a structure of Formula (IV):

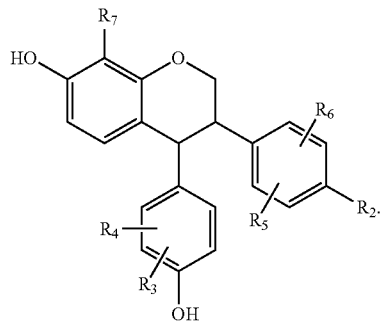

Formula (IV)

Some embodiments provided herein describe a compound of Formula (IV) that has a structure of Formula (IV-a) or (IV-b):

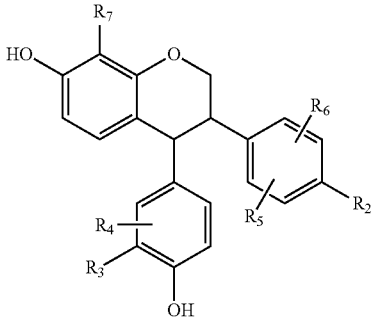

Formula (IV-a)

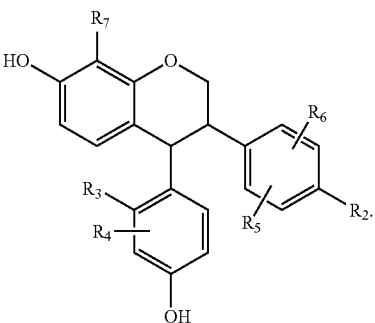

Formula (IV-b)

In some embodiments, compounds of the general Formula (IV) have the substituents $R_3$ and $R_4$ distributed as shown below:

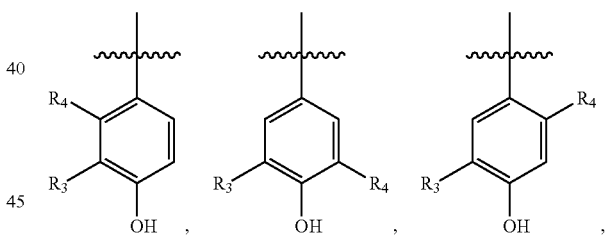

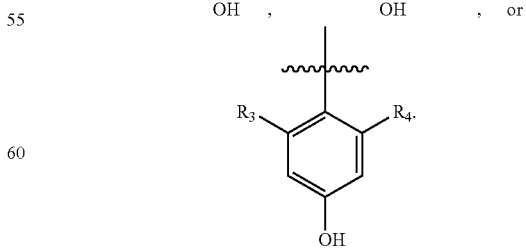

For any and all of the embodiments, substituents are selected from among a subset of the listed alternatives.

Any combination of the groups described above for the various variables is contemplated herein. Throughout the specification, groups and substituents thereof are chosen by one skilled in the field to provide stable moieties and compounds.
Exemplary compounds include the following compounds:
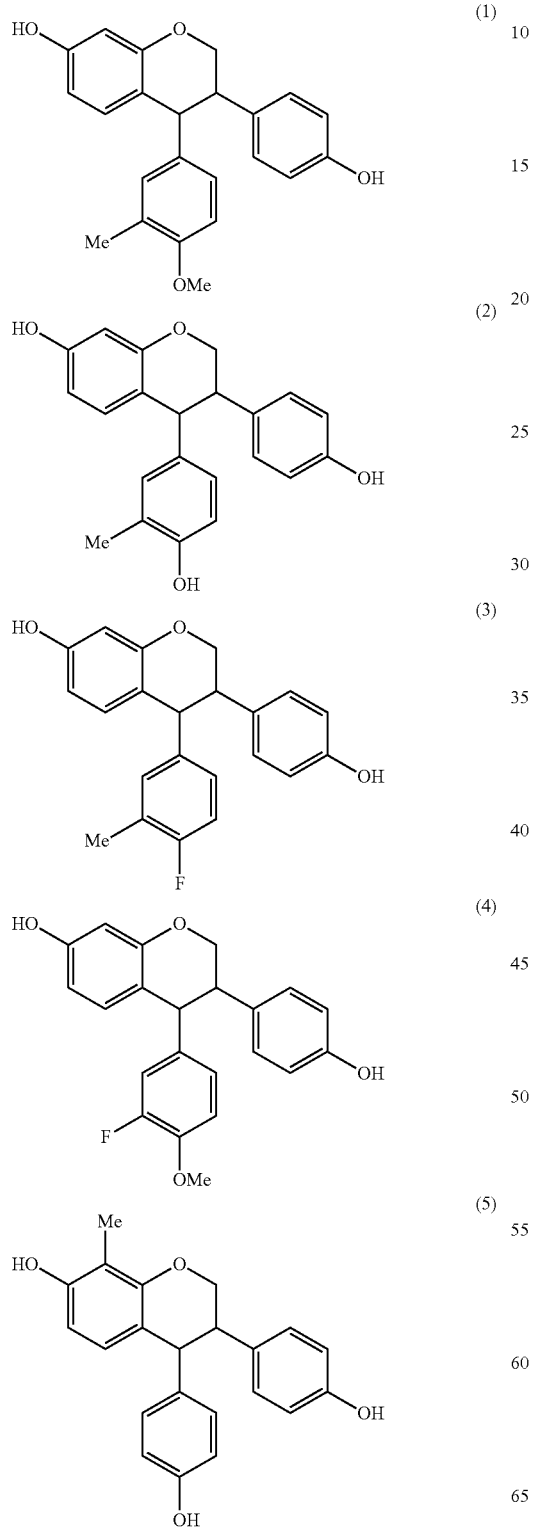
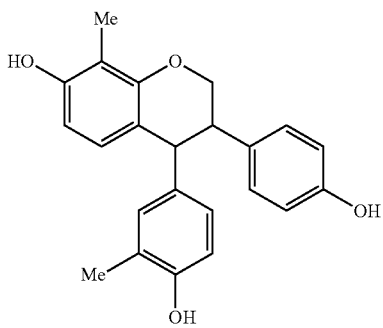
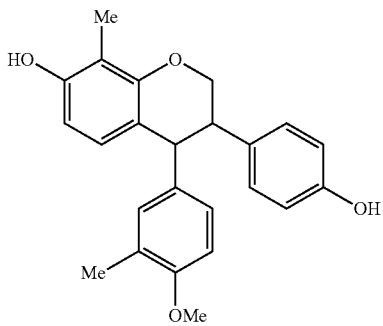
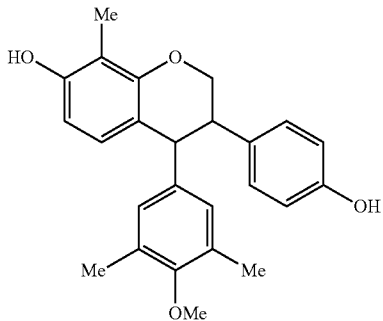
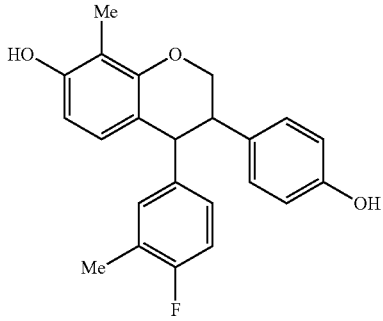
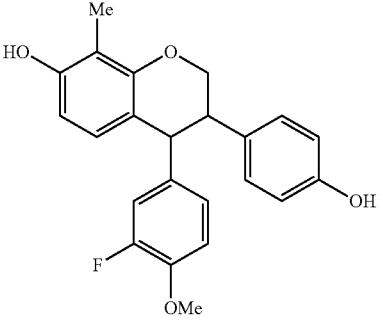

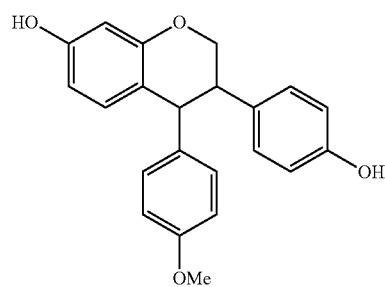
(11)
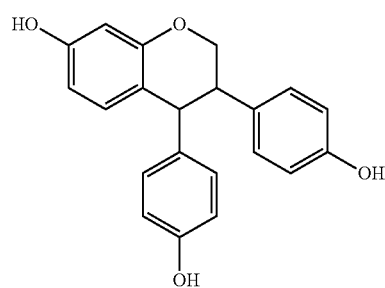
(12)
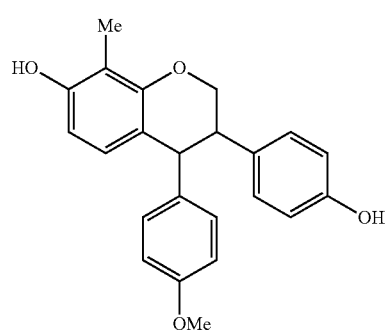
(13)
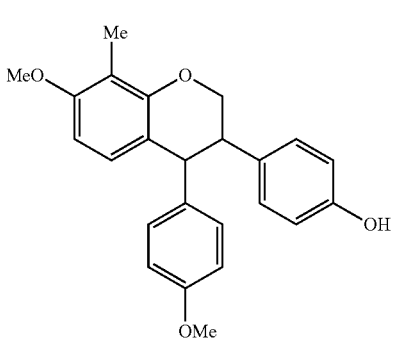
(14)
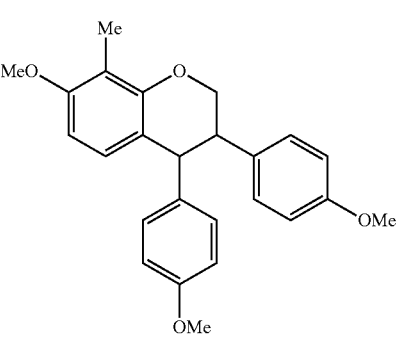
(15)
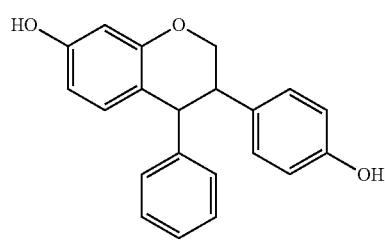
(16)
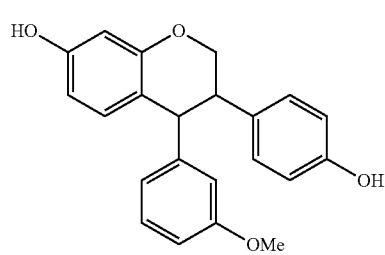
(17)
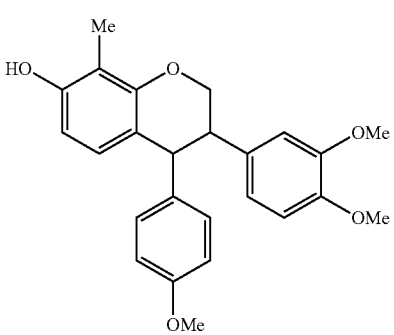
(18)
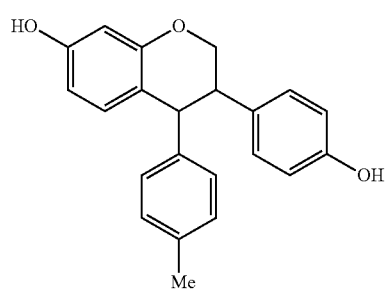
(19)
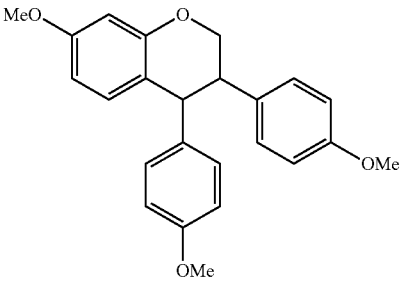
(20)

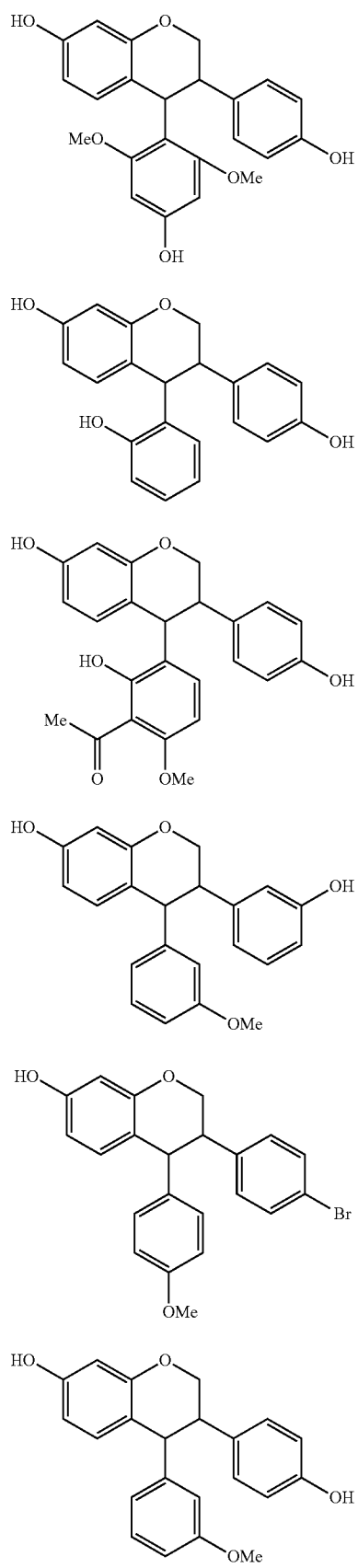

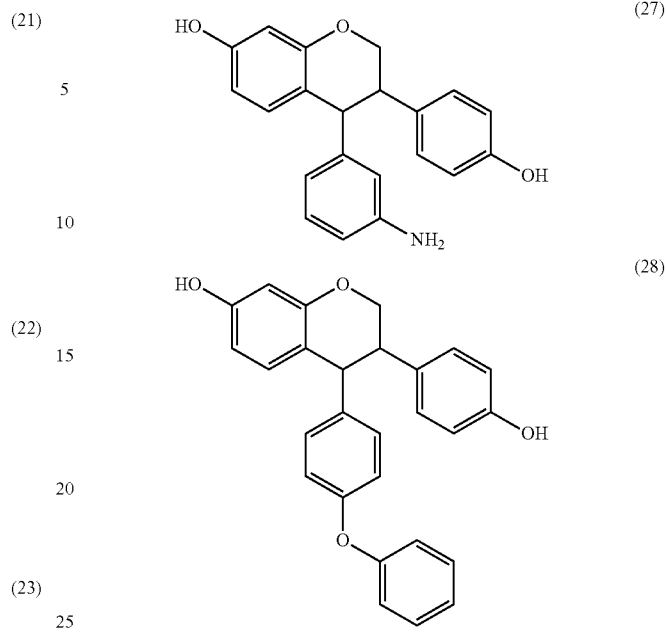

or salts or a derivative thereof.

Exemplary compounds include the following compounds:

3-(4-hydroxyphenyl)-4-(4-methoxy-3-methylphenyl)chroman-7-ol (compound 1);

3-(4-hydroxyphenyl)-4-(4-hydroxy-3-methylphenyl)chroman-7-ol (compound 2);

3-(4-hydroxyphenyl)-4-(4-fluoro-3-methylphenyl)chroman-7-ol (compound 3);

3-(4-hydroxyphenyl)-4-(4-methoxy-3-fluorophenyl)chroman-7-ol (compound 4);

3-(4-hydroxyphenyl)-4-(4-hydroxyphenyl)-8-methylchroman-7-ol (compound 5);

3-(4-hydroxyphenyl)-4-(4-hydroxy-3-methylphenyl)-8-methylchroman-7-ol (compound 6);

3-(4-hydroxyphenyl)-4-(4-methoxy-3-methylphenyl)-8-methylchroman-7-ol (compound 7);

3-(4-hydroxyphenyl)-4-(4-methoxy-3,5-dimethylphenyl)-8-methylchroman-7-ol (compound 8);

3-(4-hydroxyphenyl)-4-(4-fluoro-3-methylphenyl)-8-methylchroman-7-ol (compound 9);

3-(4-hydroxyphenyl)-4-(4-methoxy-3-fluorophenyl)-8-methylchroman-7-ol (compound 10);

3-(4-hydroxyphenyl)-4-(4-methoxyphenyl)chroman-7-ol (compound 11);

3-(4-hydroxyphenyl)-4-(4-hydroxyphenyl)chroman-7-ol (compound 12);

3-(4-hydroxyphenyl)-4-(4-methoxyphenyl)-8-methylchroman-7-ol (compound 13);

3-(4-hydroxyphenyl)-4-(4-methoxyphenyl)-7-methoxy-8-methylchroman (compound 14);

3-(4-methoxyphenyl)-4-(4-methoxyphenyl)-7-methoxy-8-methylchroman-7-ol (compound 15);

3-(4-hydroxyphenyl)-4-phenylchroman-7-ol (compound 16);

3-(4-hydroxyphenyl)-4-(3-methoxyphenyl)chroman-7-ol (compound 17);

3-(3,4-dimethoxyphenyl)-4-(4-methoxyphenyl)-8-methylchroman-7-ol (compound 18);

3-(4-hydroxyphenyl)-4-p-tolylchroman-7-ol (compound 19);

3-(4-methoxyphenyl)-4-(4-methoxyphenyl)-7-methoxychroman (compound 20);
4-(4-hydroxy-2,6-dimethoxyphenyl)-3-(4-hydroxyphenyl)chroman-7-ol (compound 21);
3-(4-hydroxyphenyl)-4-(2-hydroxyphenyl)chroman-7-ol (compound 22);
3-(4-hydroxyphenyl)-4-(3-acyl-2-hydroxy-4-methoxyphenyl)chroman-7-ol (compound 23);
3-(3-hydroxyphenyl)-4-(3-methoxyphenyl)chroman-7-ol (compound 24);
3-(4-bromophenyl)-4-(4-methoxyphenyl)chroman-7-ol (compound 25);
3-(4-hydroxyphenyl)-4-(3-methoxyphenyl)chroman-7-ol (compound 26);
4-(3-aminophenyl)-3-(4-hydroxyphenyl)chroman-7-ol (compound 27); and
3-(4-hydroxyphenyl)-4-(4-phenoxyphenyl)chroman-7-ol (compound 28).

It will be clear to persons skilled in the art that in the compounds according to certain embodiments of the invention, the aryl substituents on the heterocyclic ring can be cis or trans relative to each other. In certain embodiments of the invention, these substituents will be cis.

The compounds according to some embodiments of this invention include two chiral centers. The present invention includes all the enantiomers and diastereomers as well as mixtures thereof in any proportions. The invention also extends to isolated enantiomers or pairs of enantiomers. Some of the compounds herein (including, but not limited to benzopyran derivatives and reagents for producing the aforementioned compounds) have asymmetric carbon atoms and can therefore exist as enantiomers or diastereomers. Diastereomeric mixtures can be separated into their individual diastereomers on the basis of their physical chemical differences by methods such as chromatography and/or fractional crystallization. Enantiomers can be separated by converting the enantiomeric mixture into a diastereomeric mixture by reaction with an appropriate optically active compound (e.g., alcohol), separating the diastereomers and converting (e.g., hydrolyzing) the individual diastereomers to the corresponding pure enantiomers. All such isomers, including diastereomers, enantiomers, and mixtures thereof are considered as part of the compositions described herein.

The compounds according to some embodiments are racemic mixture. In other embodiments, any compound described herein is in the optically pure form (e.g., optically active (+) and (−), (R)- and (S)-, d- and l-, or (D)- and (L)-isomers). In certain preferred embodiments, a compound of Formulas (I), (II), (III), or (IV) is the d-isomer. Accordingly, provided herein, in some embodiments, is the optically active d-isomer having a structure of Formulas (I), (II), (III), or (IV) in enantiomeric excess. In some embodiments, the d-isomer of a compound of Formulas (I), (II), (III), or (IV) is provided in at least 50%, 55%, 60%, 65%, 70%, 75%, 80%, 85%, 88%, 90%, 91%, 92%, 93%, 94%, 95%, 96%, 97%, 98%, 99%, 95%, or 99.9% enantiomeric excess. In other embodiments, the d-isomer of a compound of Formulas (I), (II), (III), or (IV) is provided in greater than 50%, 55%, 60%, 65%, 70%, 75%, 80%, 85%, 88%, 90%, 91%, 92%, 93%, 94%, 95%, 96%, 97%, 98%, 99%, 99.5%, or 99.9% enantiomeric excess. In specific embodiments, of a compound of Formulas (I), (II), (III), or (IV) has greater than 95% enantiomeric excess.

Specific optically active compounds (i.e., enantiomers) of Formulas (I). (II), (III), or (IV) include:
d-cis-3-(4-hydroxyphenyl)-4-(4-methoxy-3-methylphenyl)chroman-7-ol (d-1);
d-cis-3-(4-hydroxyphenyl)-4-(4-hydroxy-3-methylphenyl)chroman-7-ol (d-2);
d-cis-3-(4-hydroxyphenyl)-4-(4-fluoro-3-methylphenyl)chroman-7-ol (d-3);
d-cis-3-(4-hydroxyphenyl)-4-(4-methoxy-3-fluorophenyl)chroman-7-ol (d-4);
d-cis-3-(4-hydroxyphenyl)-4-(4-hydroxyphenyl)-8-methylchroman-7-ol (d-5);
d-cis-3-(4-hydroxyphenyl)-4-(4-hydroxy-3-methylphenyl)-8-methylchroman-7-ol (d-6);
d-cis-3-(4-hydroxyphenyl)-4-(4-methoxy-3-methylphenyl)-8-methylchroman-7-ol (d-7);
d-cis-3-(4-hydroxyphenyl)-4-(4-methoxy-3,5-dimethylphenyl)-8-methylchroman-7-ol (d-8);
d-cis-3-(4-hydroxyphenyl)-4-(4-fluoro-3-methylphenyl)-8-methylchroman-7-ol (d-9);
d-cis-3-(4-hydroxyphenyl)-4-(4-methoxy-3-fluorophenyl)-8-methylchroman-7-ol (d-10);
d-cis-3-(4-hydroxyphenyl)-4-(4-methoxyphenyl)chroman-7-ol (d-11);
d-cis-3-(4-hydroxyphenyl)-4-(4-hydroxyphenyl)chroman-7-ol (d-12);
d-cis-3-(4-hydroxyphenyl)-4-(4-methoxyphenyl)-8-methylchroman-7-ol (d-13);
d-cis-(4-hydroxyphenyl)-4-(4-methoxyphenyl)-7-methoxy-8-methylchroman (d-14);
d-cis-(4-methoxyphenyl)-4-(4-methoxyphenyl)-7-methoxy-8-methylchroman-7-ol (d-15);
d-cis-3-(4-hydroxyphenyl)-4-phenylchroman-7-ol (d-16);
d-cis-3-(4-hydroxyphenyl)-4-(3-methoxyphenyl)chroman-7-ol (d-17);
d-cis-3-(3,4-dimethoxyphenyl)-4-(4-methoxyphenyl)-8-methylchroman-7-ol (d-18);
d-cis-3-(4-hydroxyphenyl)-4-p-tolylchroman-7-ol (d-19);
d-cis-3-(4-methoxyphenyl)-4-(4-methoxyphenyl)-7-methoxychroman (d-20);
d-cis-4-(4-hydroxy-2,6-dimethoxyphenyl)-3-(4-hydroxyphenyl)chroman-7-ol (d-21);
d-cis-3-(4-hydroxyphenyl)-4-(2-hydroxyphenyl)chroman-7-ol (d-22);
d-cis-3-(4-hydroxyphenyl)-4-(3-acyl-2-hydroxy-4-methoxyphenyl)chroman-7-ol (d-23);
d-cis-3-(3-hydroxyphenyl)-4-(3-methoxyphenyl)chroman-7-ol (d-24);
d-cis-3-(4-bromophenyl)-4-(4-methoxyphenyl)chroman-7-ol (d-25);
d-cis-3-(4-hydroxyphenyl)-4-(3-methoxyphenyl)chroman-7-ol (d-26);
d-cis-4-(3-aminophenyl)-3-(4-hydroxyphenyl)chroman-7-ol (d-27);
d-cis-3-(4-hydroxyphenyl)-4-(4-phenoxyphenyl)chroman-7-ol (d-28);
cis-3-(4-hydroxyphenyl)-4-(4-methoxy-3-methylphenyl)chroman-7-ol (l-1);
l-cis-3-(4-hydroxyphenyl)-4-(4-hydroxy-3-methylphenyl)chroman-7-ol (l-2);
l-cis-3-(4-hydroxyphenyl)-4-(4-fluoro-3-methylphenyl)chroman-7-ol (l-3);
l-cis-3-(4-hydroxyphenyl)-4-(4-methoxy-3-fluorophenyl)chroman-7-ol (l-4);
l-cis-3-(4-hydroxyphenyl)-4-(4-hydroxyphenyl)-8-methylchroman-7-ol (l-5);
l-cis-3-(4-hydroxyphenyl)-4-(4-hydroxy-3-methylphenyl)-8-methylchroman-7-ol (l-6);
l-cis-3-(4-hydroxyphenyl)-4-(4-methoxy-3-methylphenyl)-8-methylchroman-7-ol (l-7);

l-cis-3-(4-hydroxyphenyl)-4-(4-methoxy-3,5-dimethylphenyl)-8-methylchroman-7-ol (1-8);
cis-3-(4-hydroxyphenyl)-4-(4-fluoro-3-methylphenyl)-8-methylchroman-7-ol (1-9);
l-cis-3-(4-hydroxyphenyl)-4-(4-methoxy-3-fluorophenyl)-8-methylchroman-7-ol (1-10);
l-cis-3-(4-hydroxyphenyl)-4-(4-methoxyphenyl)chroman-7-ol (1-11);
l-cis-3-(4-hydroxyphenyl)-4-(4-hydroxyphenyl)chroman-7-ol (1-12);
l-cis-3-(4-hydroxyphenyl)-4-(4-methoxyphenyl)-8-methylchroman-7-ol (1-13);
cis-(4-hydroxyphenyl)-4-(4-methoxyphenyl)-7-methoxy-8-methylchroman (1-14);
l-cis-(4-methoxyphenyl)-4-(4-methoxyphenyl)-7-methoxy-8-methylchroman-7-ol (1-15);
l-cis-3-(4-hydroxyphenyl)-4-phenylchroman-7-ol (1-16);
l-cis-3-(4-hydroxyphenyl)-4-(3-methoxyphenyl)chroman-7-ol (1-17);
l-cis-3-(3,4-dimethoxyphenyl)-4-(4-methoxyphenyl)-8-methylchroman-7-ol (1-18);
l-cis-3-(4-hydroxyphenyl)-4-p-tolylchroman-7-ol (1-19);
l-cis-3-(4-methoxyphenyl)-4-(4-methoxyphenyl)-7-methoxychroman (1-20);
l-cis-4-(4-hydroxy-2,6-dimethoxyphenyl)-3-(4-hydroxyphenyl)chroman-7-ol (1-21);
l-cis-3-(4-hydroxyphenyl)-4-(2-hydroxyphenyl)chroman-7-ol (1-22);
l-cis-3-(4-hydroxyphenyl)-4-(3-acyl-2-hydroxy-4-methoxyphenyl)chroman-7-ol (1-23);
l-cis-3-(3-hydroxyphenyl)-4-(3-methoxyphenyl)chroman-7-ol (1-24);
l-cis-3-(4-bromophenyl)-4-(4-methoxyphenyl)chroman-7-ol (1-25);
l-cis-3-(4-hydroxyphenyl)-4-(3-methoxyphenyl)chroman-7-ol (1-26);
l-cis-4-(3-aminophenyl)-3-(4-hydroxyphenyl)chroman-7-ol (1-27); and
l-cis-3-(4-hydroxyphenyl)-4-(4-phenoxyphenyl)chroman-7-ol (1-28).

In specific embodiments, a compound of Formulas (I), (II), (III), or (IV) is d-cis-3-(4-hydroxyphenyl)-4-(4-hydroxyphenyl)chroman-7-ol. In other embodiments, a compound of Formulas (I), (II), (III), or (IV) is d-cis-3-(4-hydroxyphenyl)-4-(4-hydroxyphenyl)-8-methylchroman-7-ol.

In certain embodiments, a compound of Formulas (I), (II), (III), or (IV) is the d-isomer. Accordingly, provided herein, in some embodiments, is the optically active d-isomer having a structure of Formulas (I), (II), (III), or (IV) in enantiomeric excess. In some embodiments, the d-isomer is provided in at least 50%, 55%, 60%, 65%, 70%, 75%, 80%, 85%, 88%, 90%, 91%, 92%, 93%, 94%, 95%, 96%, 97%, 98%, 99%, 95.5%, or 99.9% enantiomeric excess. In other embodiments, the d-isomer is provided in greater than 50%, 55%, 60%, 65%, 70%, 75%, 80%, 85%, 88%, 90%, 91%, 92%, 93%, 94%, 95%, 96%, 97%, 98%, 99%, 99.5%, or 99.9% enantiomeric excess. In specific embodiments, a compound of Formulas (I), (II), (III), or (IV) has greater than 95% enantiomeric excess. In specific embodiments, a compound of Formulas (I), (II), (III), or (IV) has greater than 98% enantiomeric excess. In specific embodiments, a compound of Formulas (I), (II), (III), or (IV) has greater than 99% enantiomeric excess. In specific embodiments, a compound of Formulas (I), (II), (III), or (IV) has greater than 99.9% enantiomeric excess.

In some embodiments, the benzopyran derivative is a super-benzopyran. In some embodiments, the benzopyran derivative is Trilexium™ (TRXE-009), Cantrixil™ (TRXE-002, Trx-1), or combinations thereof. In some embodiments, the benzopyran derivative is Trilexium™. In some embodiments, the benzopyran derivative is Cantrixil™.

In additional or further embodiments, the compounds described herein are used in the form of pro-drugs. In additional or further embodiments, the compounds described herein are metabolized upon administration to an organism in need to produce a metabolite that is then used to produce a desired effect, including a desired therapeutic effect.

Any compound described herein may be synthesized according to the exemplary synthesis shown in Schemes 1 and 2. For example, compounds 6 and 7 are synthesized from 4'-bis-tert-butyldimethylsilyoxy-8-methyldihydrodaidzein. 4'-bis-tert-butyldimethylsilyoxy-8-methyldihydrodaidzein is treated with 4-methoxy-3-methylphenylmagnesium bromide in anhydrous THF. The reaction mixture is treated with wet ether (50:50 H$_2$O/Et$_2$O). The resultant mixture is extracted with Et$_2$O. The organic layer is washed with water, brine, dried over anhydrous magnesium sulfate and concentrated in vacuo. The resultant residue is treated with pTsOH and ethanol. The reaction mixture is heated to reflux for 3 hours. The reaction mixture is concentrated in vacuo then poured into water (0° C.). The mixture is extracted with EtOAc, then the organic layer is washed with water (3×), brine, dried (MgSO$_4$), filtered and concentrated in vacuo to provide the 3-alkene intermediate. The intermediate is treated with Pd catalyst and ethanol. The reaction mixture is hydrogenated at low pressure for 3 h. The reaction is filtered through Celite and the filtrate is concentrated to a volume of 15 mL. The resultant solution is added to water. The mixture is extracted with Et$_2$O (3×), the organic layers are combined and washed with water, brine, dried (MgSO$_4$), filtered and concentrated in vacuo. The resultant residue is purified by recrystallization to provide compound 7.

Scheme 1

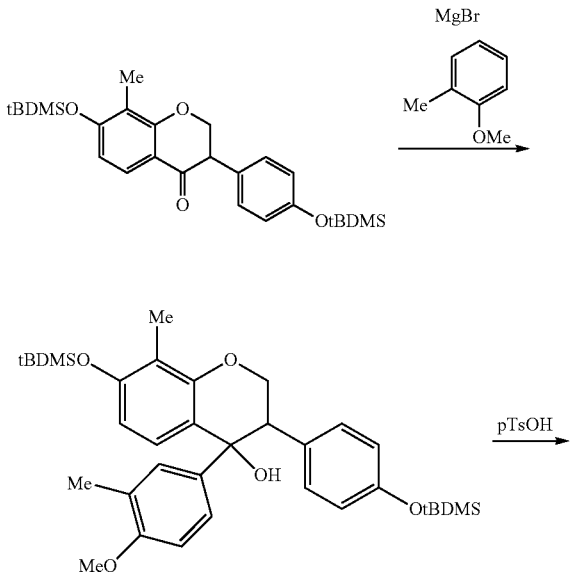

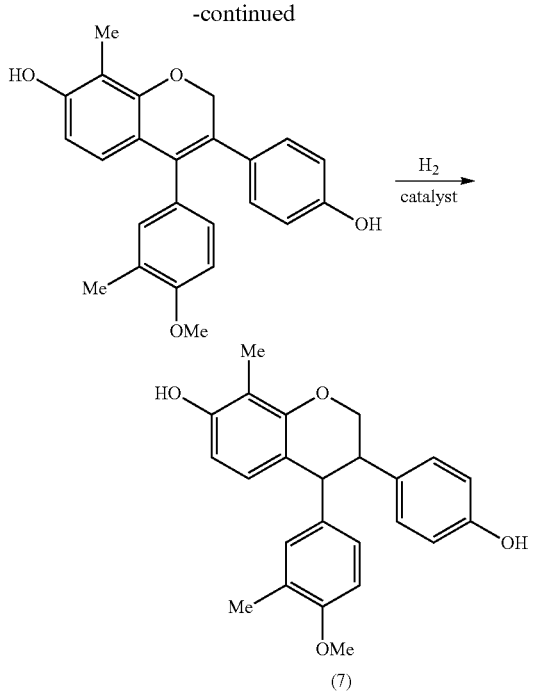

(7)

Compound 7 is transferred to a flask purged with nitrogen. Hydrogen bromide in acetic acid (33 wt %) is added drop-wise to the reaction mixture. The mixture is heated to reflux at 130° C. for 7 h. The reaction mixture is placed in an ice bath and the pH is adjusted 6. The reaction mixture is extracted with EtOAc and the organic layer is washed with water, brine, dried ($MgSO_4$), filtered and concentrated in vacuo. The resultant residue is purified by column chromatography to yield compound 6.

Scheme 2

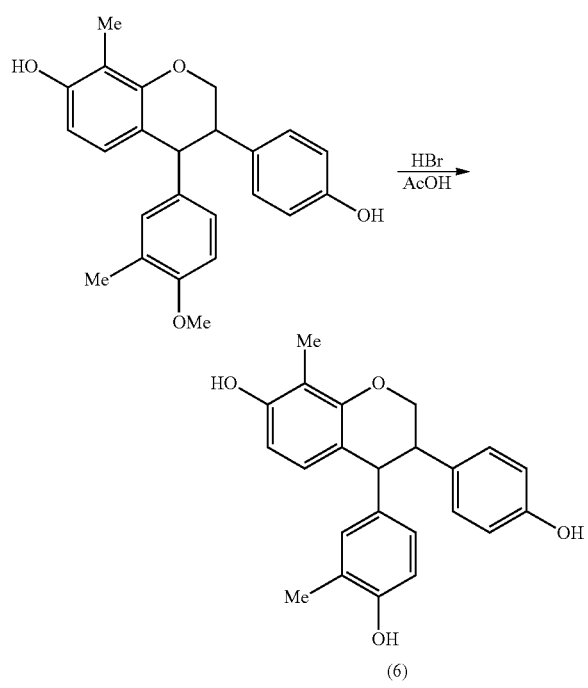

(6)

In some embodiments, compounds described herein are prepared as prodrugs. A "prodrug" refers to an agent that is converted into the parent drug in vivo. Prodrugs are often useful because, in some situations, they are easier to administer than the parent drug. They are, for instance, bioavailable by oral administration whereas the parent is not. Further or alternatively, the prodrug also has improved solubility in pharmaceutical compositions over the parent drug. In some embodiments, the design of a prodrug increases the effective water solubility. An example, without limitation, of a prodrug is a compound described herein, which is administered as an ester (the "prodrug") but then is metabolically hydrolyzed to provide the active entity. A further example of a prodrug is a short peptide (polyaminoacid) bonded to an acid group where the peptide is metabolized to reveal the active moiety. In certain embodiments, upon in vivo administration, a prodrug is chemically converted to the biologically, pharmaceutically or therapeutically active form of the compound. In certain embodiments, a prodrug is enzymatically metabolized by one or more steps or processes to the biologically, pharmaceutically or therapeutically active form of the compound.

Prodrugs of the compounds described herein include, but are not limited to, esters, ethers, carbonates, thiocarbonates, N-acyl derivatives, N-acyloxyalkyl derivatives, quaternary derivatives of tertiary amines, N-Mannich bases, Schiff bases, amino acid conjugates, phosphate esters, and sulfonate esters. See for example Design of Prodrugs, Bundgaard, A. Ed., Elseview, 1985 and Method in Enzymology, Widder, K. et al., Ed.; Academic, 1985, vol. 42, p. 309-3%; Bundgaard, H. "Design and Application of Prodrugs" in A Textbook of Drug Design and Development, Krosgaard-Larsen and H. Bundgaard, Ed., 1991, Chapter 5, p. 113-191; and Bundgaard, H., Advanced Drug Delivery Review, 1992, 8, 1-38, each of which is incorporated herein by reference. In some embodiments, a hydroxyl group in the compounds disclosed herein is used to form a prodrug, wherein the hydroxyl group is incorporated into an acyloxyalkyl ester, alkoxycarbonyloxyalkyl ester, alkyl ester, aryl ester, phosphate ester, sugar ester, ether, and the like. In some embodiments, a hydroxyl group in the compounds disclosed herein is a prodrug wherein the hydroxyl is then metabolized in vivo to provide a carboxylic acid group. In some embodiments, a carboxyl group is used to provide an ester or amide (i.e. the prodrug), which is then metabolized in vivo to provide a carboxylic acid group. In some embodiments, compounds described herein are prepared as alkyl ester prodrugs.

Prodrug forms of the herein described compounds, wherein the prodrug is metabolized in vivo to produce a compound described herein as set forth herein are included within the scope of the claims. In some cases, some of the herein-described compounds are prodrugs for another derivative or active compound.

In additional or further embodiments, the compounds described herein are metabolized upon administration to an organism in need to produce a metabolite that is then used to produce a desired effect, including a desired therapeutic effect.

A "metabolite" of a compound disclosed herein is a derivative of that compound that is formed when the compound is metabolized. The term "active metabolite" refers to a biologically active derivative of a compound that is formed when the compound is metabolized. The term "metabolized," as used herein, refers to the sum of the processes (including, but not limited to, hydrolysis reactions and reactions catalyzed by enzymes) by which a particular substance is changed by an organism. Thus, enzymes may produce specific structural alterations to a compound. For example, cytochrome P450 catalyzes a variety of oxidative and reductive reactions while uridine diphosphate glucuronyltransferases catalyze the transfer of an activated glucuronic-acid molecule to aromatic alcohols, aliphatic alcohols, carboxylic acids, amines and free sulphydryl groups. Metabolites of the compounds disclosed herein are optionally identified either by administration of compounds to a host and analysis of tissue samples from the host, or by incubation of compounds with hepatic cells in vitro and analysis of the resulting compounds.

Glycolic Inhibitors

Some embodiments provided herein describe glycolytic inhibitors that are capable of inhibiting at least one step of the glycolytic pathway in a cell. In some embodiments, the glycolytic inhibitor is a hexokinase inhibitor. In some embodiments, the hexokinase inhibitor is 2-deoxyglucose, 6-fluoroglucose, 6-thioglucose, 2-fluorodeoxyglucose, 3-bromopyruvate, or a pharmaceutically acceptable salt thereof. In some embodiments, the hexokinase inhibitor is 2-deoxyglucose, 2-fluorodeoxyglucose, 3-bromopyruvate, or a pharmaceutically acceptable salt thereof. In certain embodiments, the glycolytic inhibitor is a homolog, analog and/or derivative of 2-deoxy-D-glucose. Non-limiting examples of 2-deoxyglucose derivatives include 2-deoxy-D-glucose, 2-deoxy-L-glucose; 2-bromo-D-glucose, 2-fluoro-D-glucose, 2-iodo-D-glucose, 6-fluoro-D-glucose, 6-thio-D-glucose, 7-glucosyl fluoride, 3-fluoro-D-glucose, 4-fluoro-D-glucose, 1-O-propyl ester of 2-deoxy-D-glucose, 1-O-tridecyl ester of 2-deoxy-D-glucose, 1-O-pentadecyl ester of 2-deoxy-D-glucose, 3-O-propyl ester of 2-deoxy-D-glucose, 3-O-tridecyl ester of 2-deoxy-D-glucose, 3-O-pentadecyl ester of 2-deoxy-D-glucose, 4-O-propyl ester of 2-deoxy-D-glucose, 4-O-tridecyl ester of 2-deoxy-D-glucose, 4-O-pentadecyl ester of 2-deoxy-D-glucose, 6-O-propyl ester of 2-deoxy-D-glucose, 6-O-tridecyl ester of 2-deoxy-D-glucose, 6-O-glycolytic inhibitor is a 3-halopyruvate. In certain embodiments, the 3-halopyruvate is 3-fluoropyruvate, 3-chloropyruvate, 3-bromopyruvate or 3-iodopyruvate.

In some embodiments, the glycolytic inhibitor is a lactic dehydrogenase inhibitor. In certain embodiments, the lactic dehydrogenase inhibitor is oxamate or a pharmaceutically acceptable salt thereof. In some embodiments, the glycolytic inhibitor is a glyceraldehyde 3-phosphate dehydrogenase (e.g., iodoacetate or a pharmaceutically acceptable salt thereof).

In some embodiments, the glycolytic inhibitor is a glucose-6-phosphate dehydrogenase inhibitor. In some instances, the glucose-6-phosphate dehydrogenase inhibitor is red algal bromophenols.

In some embodiments, the glycolytic inhibitor is an angiogenesis inhibitor. In some embodiments, the angiogenesis inhibitor is a multi-tyrosine kinase inhibitor. In some embodiments, angiogenesis inhibitors include agents targeting (e.g. inhibiting) endothelial-specific receptor tyrosine kinase (Tie-2), epidermal growth factor (receptor) (EGF(R)), insulin-like growth factor (receptor) (IGF-(R)), fibroblast growth factor (receptor) (FGF(R)), platelet-derived growth factor (receptor) (PDGF(R)), hepatocyte growth factor (receptor) (HGF(R)), or vascular endothelial growth factor (VEGF) or VEGF receptor (VEGFR); as well as thrombospondin analogs, matrix metalloprotease (e.g. MMP-2 or MMP-9) inhibitors, thalidomide or thalidomide analogs, integrins, angiostatin, endostatin, vascular disrupting agents, protein kinase C(PKC) inhibitors, and the like.

In some embodiments, angiogenesis inhibitors are agents targeting (e.g. inhibiting) vascular endothelial growth factor (VEGF) or VEGF receptor (VEGFR). Agents targeting (e.g. inhibiting) VEGF/VEGFR relate to compounds which target (e.g. inhibit) one or more members of the VEGF or VEGFR family (VEGFR1, VEGFR2, VEGFR3) and include inhibitors of any vascular endothelial growth factor (VEGF) ligand (such as e.g. ligand antibodies or soluble receptors) as well as inhibitors of any VEGF receptor (VEGFR) (such as e.g. VEGFR tyrosin kinase inhibitors, VEGFR antagonists or receptor antibodies). Examples of small molecule VEGFR inhibitors include, without being limited to, sorafenib (Nexavar, also an inhibitor of Raf, PDGFR, Flt3, Kit and RETR), sunitinib (Sutent, also inhibitor of Kit, Flt3 and PDGFR), pazopanib (GW-786034, also inhibitor of Kit and PDGFR), cediranib (Recentin, AZD-2171), axitinib (AG-013736, also inhibitor of PDGFR and Kit), vandetanib (Zactima, ZD-6474, also inhibitor of EGFR and Ret), vatalanib (also inhibitor of PDGFR and Kit), motesanib (AMG-706, also inhibitor of PDGFR and Kit), brivanib (also FGFR inhibitor), linifanib (ABT-869, also inhibitor of PDGFR, Flt3 and Kit), tivozanib (KRN-951, also inhibitor of PDGFR, Kit, and MAP), BMS-690514 (also and inhibitor of EGFR and HER-2), E-7080 (also inhibitor of Kit and Kdr), regorafenib (BAY-73-4506, also inhibitor of Tek), foretinib (XL-880, also inhibitor of Flt3, Kit and Met), telatinib (BAY-57-9352), MGCD-265 (also inhibitor of c-MET, Tie2 and Ron), dovitinib (also inhibitor of PDGFR, Flt3, Kit and FGFR), nintedanib (also inhibitor of FGFR and PDGFR), XL-184 (cabozantinib, also inhibitor of Met, Flt3, Ret, Tek and Kit). Examples of biological entities inhibiting VEGF (R) include, without being limited to, anti-VEGF ligand antibodies such as bevacizumab (Avastin); soluble receptors such as aflibercept (VEGF-Trap); anti-VEGF receptor antibodies such as ramucirumab (IMC-1121b) or IMC-18F1; VEGFR antagonists such as CT-322 or CDP-791.

Agents targeting (e.g. inhibiting) PDGFR relate to compounds which target (e.g. inhibit) one or more members of the PDGFR family and include inhibitors of a platelet-derived growth factor receptor (PDGFR) family tyrosin kinase (either as single kinase inhibitor or as multikinase inhibitor) as well as anti-PDGFR antibodies. Examples of small molecule PDGFR inhibitors include, without being limited to, nintedanib (also inhibitor of VEGFR and FGFR), axitinib (also inhibitor of VEGFR and Kit), dovitinib (also inhibitor of VEGFR, Flt3, Kit and FGFR), sunitinib (also inhibitor of VEGFR, Flt3 and Kit), motesanib (also inhibitor of VEGFR and Kit), pazopanib (also inhibitor of VEGFR and Kit), nilotinib (also inhibitor of Abl and Kit), tandutinib (also inhibitor of Flt3 and Kit), vatalanib (also inhibitor of VEGFR and Kit), tivozanib (KRN-951, also inhibitor of VEGFR, Kit, and MAP), AC-220 (also inhibitor of Flt3 and Kit), TSU-68 (also inhibitor of FGFR and VEGFR), KRN-633 (also inhibitor of VEGFR, Kit and Flt3), linifinib (also inhibitor of Flt3. Kit and VEGFR), sorafenib (Nexavar, also an inhibitor of Raf, VEGFR. Flt3, Kit and RETR), imatinib (Gleevec, also inhibitor of Abl and Kit). Examples of anti-PDGFR antibodies include IMC-3G3.

Agents targeting FGFR relate to compounds which target one or more members of the FGFR family and include inhibitors of a fibroblast growth factor receptor family tyrosin kinase (either as single kinase inhibitor or as multi-kinase inhibitor). Examples of small molecule FGFR inhibitors include, without being limited to, nintedanib (also inhibitor of VEGFR and PDGFR), dovitinib (also inhibitor of VEGFR, Flt3, Kit and PDGFR). KW-2449 (also inhibitor of Flt3 and Abl), brivanib (also VEGFR inhibitor), TSU-68 (also inhibitor of PDGFR and VEGFR).

Agents targeting (e.g. inhibiting) EGFR relate to compounds which target (e.g. inhibit) one or more members of the epidermal growth factor receptor family (erbB1, erbB2, erbB3, erbB4) and include inhibitors of one or more members of the epidermal growth factor receptor (EGFR) family kinases (either as single kinase inhibitor or as multikinase inhibitor) as well as antibodies binding to one or more members of the epidermal growth factor receptor (EGFR) family. Examples of small molecule epidermal growth factor receptor (EGFR) inhibitors include, without being limited to, erlotinib (Tarceva), gefitinib (Iressa), afatinib, lapatinib (Tykerb), vandetanib (Zactima, also inhibitor of VEGFR and RETR), BMS-690514 (also an inhibitor of VEGFR), neratinib (HKI-272), varlitinib, AZD-8931, AC-480, AEE-788 (also inhibitor of VEGFR). Examples of antibodies against the epidermal growth factor receptor (EGFR) include the anti-ErbB1 antibodies cetuximab, panitumumab or nimotuzumab, the anti-ErbB2 antibodies trastuzumab (Herceptin), pertuzumab (Omnitarg) or ertumaxomab, and the anti-EGFR antibody zalutumumab.

IGF(R) inhibitors are agents that target one or more members of the insulin-like growth factor (IGF) family (e.g. IGF1 and/or IGF2), particularly of the IGFR family of tyrosine kinases, e.g. IGFR-1 (either as single kinase inhibitor or as multikinase inhibitor), and/or of insulin receptor pathways, and may include, without being limited to, the IGFR tyrosin kinase inhibitors OSI-906 (linsitinib) and 1-{4-[(5-cyclopropyl-1H-pyrazol-3-yl)amino]pyrrolo[2,1-f][1,2,4]triazin-2-yl}-N-(6-fluoro-3-pyridinyl)-2-methyl-L-prolinamide (BMS-754807), as well as the anti-IGF(R) antibodies figitumumab, cixutumumab, dalotuzumab, ganitumab and robatumumab.

HGF(R) inhibitors are agents that target one or more members of the hepatocyte growth factor (HGF) family, particularly of the HGFR family of tyrosine kinases (either as single kinase inhibitor or as multikinase inhibitor), and may include, without being limited to, the HGFR tyrosin kinase inhibitors cabozantinib (XL-184, also inhibitor of VEGFR, Flt3, Ret, Tek and Kit), crizotinib (also inhibitor of Alk), foretinib (also inhibitor of Flt3, Kit and VEGFR) and tivantinib, as well as the anti-HGF(R) antibodies ficlatuzumab and onartuzumab.

In some embodiments, vascular disrupting agents include, without being limited to, 5,6-dimethylxanthenone-4-acetic acid (DMXAA, vadimezan), combretastatin A4 phosphate (Zybrestat) or combretastatin A4 analogues, such as ombrabulin (AVE-8062).

In some instances, the angiogenesis inhibitor is nintedanib (BIBF 1120, Vargatef), bevacizumab (Avastin), everolimus (Afinitor), temsirolimus (Torisel), lenalidomide (Revlimid), pazopanib (Votrient), ramucirumab (Cyramza), sorafenib (Nexavar), sunitinib (Sutent), thalidomide (Thalomid), vandetanib (Caprelsa), cediranib (Recentin), axitinib (Inlyta), motesanib, vatalanib, dovitinib, brivanib, linifanib, tivozanib, lenvatinib, regorafenib (Stivarga), foretinib, telatinib, cabozantinib (Cometriq), nilotinib (Tasigna), tandutinib, imatinib (Gleevec), BMS-690514, quizartinib (AC220), orantinib, olaratumab, erlotinib (Tarceva), gefitinib (Iressa), afatinib (Gilotrif), lapatinib (Tykerb), varlitinib, AEE-788, trastuzumab (Herceptin), cetuximab (Erbitux), panitumumab (Vectibix), nimotuzumab, pertuzumab (Omnitarg), ertumaxomab, or zalutumumab. In some embodiments, the angiogenesis inhibitor is nintedanib (BIBF 1120), everolimus (Afinitor), temsirolimus (Torisel), pazopanib (Votrient), axitinib (Inlyta), bevacizumab (Avastin), sorafenib (Nexavar), sunitinib (Sutent), thalidomide (Thalomid), dovitinib, regorafenib (Stivarga), or imatinib (Gleevec). In certain embodiments, the angiogenesis inhibitor is dovitinib, regorafenib (Stivarga), or nintedanib (BIBF 1120). In certain embodiments, the angiogenesis inhibitor is dovitinib or nintedanib (BIBF 1120). In certain embodiments, the angiogenesis inhibitor is dovitinib. In certain embodiments, the angiogenesis inhibitor is nintedanib (BIBF 1120).

Methods

Some embodiments provided herein describe a method of inducing apoptosis in a cancer cell. Also described herein, in other embodiments, is a method of treating cancer in an individual in need of cancer therapy. In specific embodiments, the methods comprise contacting the cancer or cancer cell with an oxidative phosphorylation inhibitor (e.g., a benzopyran derivative) and a glycolytic inhibitor. In certain embodiments, the cancer or cancer cell is present in an individual. In specific embodiments, the individual is in need of cancer therapy.

In other embodiments, provided herein is a method of treating a disease or disorder associated with dysregulation of cell proliferation. In some embodiments, the disease or disorder is cancer. In other embodiments, provided herein is a method of increasing, inducing, or restoring sensitivity to a cancer therapy in an individual. Some embodiments provided herein describe a method of treating a chemoresistant cancer. In specific embodiments, the methods comprise contacting the cancer or cancer cell with an oxidative phosphorylation inhibitor (e.g., a benzopyran derivative) and a glycolytic inhibitor. In certain embodiments, the cancer or cancer cell is present in an individual. In specific embodiments, the individual is in need of cancer therapy.

In some embodiments, the cancer or cancer cell has lost sensitivity to a chemotherapeutic agent, anti-cancer agent or radiation therapy. In some embodiments, the combination of an oxidative phosphorylation inhibitor (e.g., a benzopyran derivative) and a glycolytic inhibitor has an enhanced effect. In other embodiments, the combination of an oxidative phosphorylation inhibitor (e.g., a benzopyran derivative), a glycolytic inhibitor, and an additional anti-cancer agent has an enhanced effect. In some embodiments, the combination therapies and/or compositions described herein chemosensitize cancer cells, wherein the combination therapies and/or compositions lower the amount of anti-cancer agent that is required to kill the cancer cell. In other embodiments, the combination therapies and/or compositions described herein chemosensitize cancer cells, wherein the combination therapies and/or compositions convert cancer cells from a state of chemo-resistant to chemo-sensitive. In further or additional embodiments, the combination therapies and/or compositions described herein radiosensitize cancer cells, wherein the combination therapies and/or compositions lower the amount of gamma-irradiation that is required to kill the cancer cell. In other embodiments, the combination therapies and/or compositions described herein radiosensitize cancer cells, wherein the combination therapies and/or compositions convert cancer cells from a state of radio-resistant to radio-sensitive.

In some embodiments, the cancer is drug-resistant or chemoresistant. In some embodiments, the cancer is multidrug resistant. As used herein, a "drug-resistant cancer" is a cancer that is resistant to conventional commonly known cancer therapies. Examples of conventional cancer therapies include treatment of the cancer with agents such as methotrexate, doxorubicin, 5-fluorouracil, vincristine, vinblastine, pamidronate disodium, anastrozole, exemestane, cyclophosphamide, epirubicin, toremifene, letrozole, trastuzumab, megestrol, tamoxifen, paclitaxel, docetaxel, capecitabine, goserelin acetate, etc. In some embodiments, the cancer is resistant to nintedanib. A "multi-drug resistant cancer" is a cancer that resists more than one type or class of cancer agents. i.e., the cancer is able to resist a first drug having a first mechanism of action, and a second drug having a second mechanism of action.

Provided herein in some embodiments, is a method to treat cancer in an individual, the method comprising administering to the individual an oxidative phosphorylation inhibitor (e.g., a benzopyran derivative) and a glycolytic inhibitor, wherein the side-effects associated with chemotherapy, radiotherapy, or cancer therapy is reduced or minimized. In some instances, the combination therapies and/or compositions described herein provide chemo-protective and/or radio-protective properties to non-cancerous cells. In further or additional embodiments, the lower amount of oxidative phosphorylation inhibitor (e.g., a benzopyran derivative), a glycolytic inhibitor, or additional anti-cancer agent reduces or minimizes any undesired side-effects associated with chemotherapy. Non-limiting examples of side-effects associated with chemotherapy, radiotherapy or cancer therapy include fatigue, anemia, appetite changes, bleeding problems, diarrhea, constipation, hair loss, nausea, vomiting, pain, peripheral neuropathy, swelling, skin and nail changes, urinary and bladder changes, and trouble swallowing.

Also described herein, in some embodiments, is a method of killing cancer cells in an individual, wherein the cancer cells include cancer cells that create ATP for energy anaerobically and cancer cells that aerobically generate ATP, the method comprising administering to an individual an oxidative phosphorylation inhibitor (e.g., a benzopyran derivative) and a glycolytic inhibitor.

In some instances, cancer cells, e.g., at the inner core of a tumor, are poorly oxygenated and consequently rely on anaerobic metabolism for survival. In some instances, cancer cells use steps of the glycolytic pathway to create ATP for energy anaerobically. In some instances, these tumor cells divide more slowly than outer growing aerobic cells and consequently are more resistant to standard chemotherapeutic agents which target rapidly dividing cells. In some instances, the anaerobic tumor cells are resistant to chemotherapeutic agents that target aerobic metabolism (e.g., oxidative phosphorylation). In some instances, cells growing anaerobically exhibit a form of multidrug resistance (MDR).

In some instances, cancer cells metabolize glucose at high rates to synthesize high levels of ATP, exhibiting increased glycloysis. In some instances where the glycolytic pathway is inhibited, cancer cells develop an escape mechanism and switch to mitochondrial oxidative phosphorylation to synthesize ATP. In some instances, the cancer cells shift to reliance on mitochondrial metabolism as the primary energy source.

In some embodiments, the combination therapies and/or compositions are used to treat anaerobic tumor cells and aerobic tumor cells (with inhibitors of oxidative phosphorylation). In some embodiments, the combination therapies and/or compositions provide synergistic antitumor activity. In some instances, inhibiting oxidative phosphorylation to convert aerobic tumor cells to anaerobic cells, hypersensitizes the cancer cells to glycolytic inhibitors. In some instances, inhibiting glycolysis to convert anaerobic tumor cells to aerobic cells, hypersensitizes the cancer cells to oxidative phosphorylation inhibitors (e.g., benzopyran derivatives).

The administration time of the oxidative phosphorylation inhibitors (e.g., benzopyran derivatives) and the glycolytic inhibitors is not restricted. In some embodiments, the oxidative phosphorylation inhibitors (e.g., benzopyran derivatives) and the glycolytic inhibitors are administered to an individual simultaneously. In other embodiments, the oxidative phosphorylation inhibitors (e.g., benzopyran derivatives) and the glycolytic inhibitors are administered at staggered times. In certain embodiments, the individual is first treated with a glycolytic inhibitor, followed by an oxidative phosphorylation inhibitor. In certain embodiments, the individual is first treated with an oxidative phosphorylation inhibitor, followed by a glycolytic inhibitor.

Some embodiments provided herein describe a method of treating cancer or a tumor in a subject, the method comprising i) treating the subject with a glycolytic inhibitor; ii) administering to the subject a positron emission tomography (PET) scan (or other imaging procedure suitable to assess efficacy of anti-cancer or anti-tumor treatment with the glycolytic inhibitor); and iii) if the result of the PET scan (or other imaging) testing procedure in step ii is positive (i.e., if the cancer or tumor is responsive), treating the subject with the glycolytic inhibitor and an oxidative phosphorylation inhibitor (e.g., a benzopyran derivative). In some instances, if the result of the PET scan (or other imaging procedure) in step ii is negative (i.e., the tumor or cancer is unresponsive to the glycolytic inhibitor), treatment with the glycolytic inhibitor is continued and the PET scan (or other imaging procedure) in step ii is re-administered in 1 month, 2 months, 3 months, 4 months, 5 months, or 6 months, at which point, if the result of the PET scan (or other imaging) testing procedure in step ii is positive (i.e., if the cancer or tumor is responsive), treating the subject with the glycolytic inhibitor and an oxidative phosphorylation inhibitor (e.g., a benzopyran derivative).

In some embodiments, the cancer is selected from the group consisting of bladder cancer, breast cancer, metastatic breast cancer, metastatic HER2-negative breast cancer, colon cancer, rectal cancer, metastatic colorectal cancer, endometrial cancer, cervical cancer, uterine cancer, ovarian cancer, kidney cancer, liver cancer, leukemia, lung cancer (both small cell and non-small cell), squamous non-small cell lung cancer, non-squamous non-small cell lung cancer, melanoma, Lewis lung carcinoma, non-Hodgkin lymphoma, pancreatic cancer, testicular cancer, prostate cancer, thyroid cancer, sarcoma (including osteosarcoma), esophageal cancer, gastric cancer, head and neck cancer, lung cancer melanoma, myeloma, neuroblastoma, glioblastoma, and cancers of the brain. In some embodiments, the cancer is selected from, by way of non-limiting example, human breast, prostate, ovarian, pancreatic, or cervical cancer. In certain specific embodiments, the cancer is human breast cancer or ovarian cancer.

A tumor cell in a subject or individual may be part of any type of cancer. Some examples of cancer include, but are not limited to, biliary tract cancer; bladder cancer; brain cancer including glioblastomas and medulloblastomas; breast cancer; cervical cancer; choriocarcinoma; colon cancer; endometrial cancer; esophageal cancer; gastric cancer; hematological neoplasms including acute lymphocytic and myelogenous leukemia; multiple myeloma; AIDS-associated leukemias and adult T-cell leukemia lymphoma; intraepithelial neoplasms including Bowen's disease and Paget's disease; liver cancer; lung cancer; lymphomas including Hodgkin's disease and lymphocytic lymphomas; neuroblastomas; oral cancer including squamous cell carcinoma; ovarian cancer including those arising from epithelial cells, stromal cells, germ cells and mesenchymal cells; pancreatic cancer; prostate cancer; rectal cancer; sarcomas including leiomyosarcoma, rhabdomyosarcoma, liposarcoma, fibrosarcoma, and osteosarcoma; skin cancer including melanoma, Kaposi's sarcoma, basocellular cancer, and squamous cell cancer; testicular cancer including germinal tumors such as seminoma, non-seminoma, teratomas, choriocarcinomas; stromal tumors and germ cell tumors; thyroid cancer including thyroid adenocarcinoma and medullar carcinoma; and renal cancer including adenocarcinoma and Wilms' tumor.

In some embodiments, the methods described herein are useful in treating various cancers including but not limited to bone cancers including Ewing's sarcoma, osteosarcoma, chondrosarcoma and the like, brain and CNS tumours including acoustic neuroma, neuroblastomas, glioma and other brain tumours, spinal cord tumours, breast cancers including ductal adenocarcinoma, metastatic ductal breast carcinoma, colorectal cancers, advanced colorectal adenocarcinomas, colon cancers, endocrine cancers including adenocortical carcinoma, pancreatic cancer, pituitary cancer, thyroid cancer, parathyroid cancer, thymus cancer, multiple endocrine neoplasma, gastrointestinal cancers including stomach cancer, esophageal cancer, small intestine cancer, liver cancer, extra hepatic bile duct cancer, gastrointestinal carcinoid tumour, gall bladder cancer, genitourinary cancers including testicular cancer, penile cancer, prostate cancer, gynaecological cancers including cervical cancer, ovarian cancer, vaginal cancer, uterus/endometrium cancer, vulva cancer, gestational trophoblastic cancer, fallopian tube cancer, uterine sarcoma, head and neck cancers including oral cavity cancer, lip cancer, salivary gland cancer, larynx cancer, hypopharynx cancer, orthopharynx cancer, nasal cancer, paranasal cancer, nasopharynx cancer, leukemias including childhood leukemia, acute lymphocytic leukemia, acute myeloid leukemia, chronic lymphocytic leukemia, chronic myeloid leukemia, hairy cell leukemia, acute promyelocytic leukemia, plasma cell leukemia, erythroleukemia, myelomas, haematological disorders including myelodysplasia syndromes, myeloproliferative disorders, aplastic anemia. Fanconi anemia, Waldenstroms Macroglobulinemia, lung cancers including small cell lung cancer, non-small cell lung cancer, squamous cell lung cancer. Lewis lung carcinoma, mesothelioma, lymphomas including Hodgkin's disease, non-Hodgkin's lymphoma, cutaneous T-cell lymphoma, peripheral T-cell lymphoma, AIDS related Lymphoma, B-cell lymphoma, Burkitt's lymphoma, eye cancers including retinoblastoma, intraocular melanoma, skin cancers including melanoma, non-melanoma skin cancer, squamous cell carcinoma, merkel cell cancer, soft tissue sarcomas such as childhood soft tissue sarcoma, adult soft tissue sarcoma, Kaposi's sarcoma, urinary system cancers including kidney cancer, Wilms tumour, bladder cancer, urethral cancer, and transitional cell cancer.

In some embodiments, the cancer is a hematological malignancy. In some embodiments, wherein the hematological malignancy is acute myeloid leukemia (AML), chronic myeloid leukemia (CML), chronic myelomonocytic leukemia, thrombolytic leukemia, a myelodysplasia syndrome (MDS), a myeloproliferative disorder, refractory anemia, a preleukemia syndrome, a lymphoid leukemia, lymphoma, non-Hodgkin's lymphoma, or an undifferentiated leukemia. In some specific embodiments, the cancer is myelodysplasia syndrome (MDS) or acute myeloid leukemia (AML). Non-limiting examples of non-Hodgkin's lymphoma include diffuse large B-cell lymphoma (DLBCL), mantle cell lymphoma (MCL), and chronic lymphocytic leukemia (CLL).

Other exemplary cancers that may be treated by the methods described herein include but are not limited to leukemias such as erythroleukemia, acute promyelocytic leukemia, acute myeloid leukemia, acute lymphocytic leukemia, acute T-cell leukemia and lymphoma such as B-cell lymphoma (e.g. Burkitt's lymphoma), cutaneous T-cell lymphoma (CTCL), and peripheral T-cell lymphoma.

Additional Agents

Any of the methods described herein, in some embodiments, further comprise administering cancer therapy to the individual or patient. In certain embodiments, the cancer therapy is, by way of non-limiting example, at least one anti-cancer agent (e.g., chemotherapeutic agent), radiation therapy, or surgery. In some embodiments, a combination of (1) administration of an effective amount of a compound described herein and (2) 1 to 3 therapies selected from the group consisting of (i) administration of an effective amount of an additional anticancer agents, (ii) administration of an effective amount of hormonal therapeutic agents and (iii) non-drug therapy prevents and/or treats cancer more effectively.

The administration time of the combination therapy/composition and a concomitant anti-cancer agent is not restricted. In some embodiments, the combination therapy/composition and a concomitant anti-cancer agent are administered to an individual simultaneously. In other embodiments, the combination therapy/composition and a concomitant anti-cancer agent are administered at staggered times.

An anti-cancer agent includes but is not limited to a chemotherapeutic agent, immunotherapeutic agent, a pharmaceutical agent that inhibits the action of cell growth factor and a receptor thereof and the like. Among the chemotherapeutic agents that are optionally employed, by way of non-limiting example, are cisplatin, carboplatin, paclitaxel, gemcitabine or doxorubicin. Further, non-limiting examples of chemotherapeutic agents include alkylating agents, antimetabolites, anticancer antibiotics, plant-derived anticancer agents, and the like.

Alkylating agents include but are not limited to nitrogen mustard, nitrogen mustard-N-oxide hydrochloride, chlorambutyl, cyclophosphamide, ifosfamide, thiotepa, carboquone, improsulfan tosylate, busulfan, nimustine hydrochloride, mitobronitol, melphalan, dacarbazine, ranimustine, sodium estramustine phosphate, triethylenemelamine, carmustine, lomustine, streptozocin, pipobroman, etoglucid, carboplatin, cisplatin, miboplatin, nedaplatin, oxaliplatin, altretamine, ambamustine, dibrospidium hydrochloride, fotemustine, prednimustine, pumitepa, ribomustin, temozolomide, treosulphan, trophosphamide, zinostatin stimalamer, adozelesin, cystemustine, bizelesin, and the like.

Antimetabolites include but are not limited to mercaptopurine, 6-mercaptopurine riboside, thioinosine, methotrexate, enocitabine, cytarabine, cytarabine ocfosfate, ancitabine hydrochloride, 5-FU drugs (e.g., fluorouracil, tegafur, UFT, doxifluridine, carmofur, gallocitabine, emitefur, and the like), aminopterine, leucovorin calcium, tabloid, butocine, folinate calcium, levofolinate calcium, cladribine, emitefur, fludarabine, gemcitabine, hydroxycarbamide, pentostatin, piritrexim, idoxuridine, mitoguazone, thiazophrine, ambamustine and the like.

Anticancer antibiotics include but are not limited to actinomycin-D, actinomycin-C, mitomycin-C, chromomycin-A3, bleomycin hydrochloride, bleomycin sulfate, peplomycin sulfate, daunorubicin hydrochloride, doxorubicin hydrochloride, aclarubicin hydrochloride, pirarubicin hydrochloride, epirubicin hydrochloride, neocarzinostatin, mithramycin, sarcomycin, carzinophilin, mitotane, zorubicin hydrochloride, mitoxantrone hydrochloride, idarubicin hydrochloride, and the like.

Plant-derived anticancer agents include but are not limited to etoposide, etoposide phosphate, vinblastine sulfate, vincristine sulfate, vindesine sulfate, teniposide, paclitaxel, docetaxel, vinorelbine, and the like.

Immunotherapeutic agents include but are not limited to picibanil, krestin, sizofuran, lentinan, ubenimex, interferons, interleukins, macrophage colony-stimulating factor, granulocyte colony-stimulating factor, erythropoietin, lymphotoxin, BCG vaccine, *Corynebacterium parvum*, levamisole, polysaccharide K, procodazole, and the like.

Non-limiting examples of a cell growth factor in pharmaceutical agents that inhibit the action of cell growth factors or cell growth factor receptors include any substances that promote cell proliferation, which are normally peptides having a molecular weight of not more than 20,000 that are capable of exhibiting their activity at low concentrations by binding to a receptor, including (1) EGF (epidermal growth factor) or substances possessing substantially the same activity as it [e.g., EGF, heregulin, and the like], (2) insulin or substances possessing substantially the same activity as it [e.g., insulin, IGF (insulin-like growth factor)-1, IGF-2, and the like], (3) FGF (fibroblast growth factor) or substances possessing substantially the same activity as it [e.g., acidic FGF, basic FGF, KGF (keratinocyte growth factor), FGF-10, and the like], (4) other cell growth factors [e.g., CSF (colony stimulating factor), EPO (erythropoietin), IL-2 (interleukin-2), NGF (nerve growth factor), PDGF (platelet-derived growth factor), TGFβ (transforming growth factor β), HGF (hepatocyte growth factor), VEGF (vascular endothelial growth factor), and the like], and the like.

Cell growth factor receptors include but are not limited to any receptors capable of binding to the aforementioned cell growth factors, including EGF receptor, heregulin receptor (HER2), insulin receptor, IGF receptor, FGF receptor-1 or FGF receptor-2, and the like.

Pharmaceutical agents that inhibit the action of cell growth factor include but are not limited to HER2 antibody (e.g., trastuzumab), imatinib mesylate, ZD1839 or EGFR antibody (e.g., cetuximab), antibody to VEGF (e.g., bevacizumab), VEGFR antibody, VEGFR inhibitor, and EGFR inhibitor (e.g., erlotinib).

In addition to the aforementioned drugs, other anti-cancer agents include but are not limited to L-asparaginase, aceglatone, procarbazine hydrochloride, protoporphyrin-cobalt complex salt, mercuric hematoporphyrin-sodium, topoisomerase I inhibitors (e.g., irinotecan, topotecan, and the like), topoisomerase II inhibitors (e.g., sobuzoxane, and the like), differentiation inducers (e.g., retinoid, vitamin D, and the like), α-blockers (e.g., tamsulosin hydrochloride, naftopidil, urapidil, alfuzosin, terazosin, prazosin, silodosin, and the like) serine/threonine kinase inhibitor, endothelin receptor antagonist (e.g., atrasentan, and the like), proteasome inhibitor (e.g., bortezomib, and the like), Hsp 90 inhibitor (e.g., 17-AAG, and the like), spironolactone, minoxidil, 11α-hydroxyprogesterone, bone resorption inhibiting/metastasis suppressing agent (e.g., zoledronic acid, alendronic acid, pamidronic acid, etidronic acid, ibandronic acid, clodronic acid) and the like.

Non-limiting examples of hormonal therapeutic agents include fosfestrol, diethylstylbestrol, chlorotrianisene, medroxyprogesterone acetate, megestrol acetate, chlormadinone acetate, cyproterone acetate, danazol, dienogest, asoprisnil, allylestrenol, gestrinone, nomegestrol, Tadenan, mepartricin, raloxifene, ormeloxifene, levormeloxifene, anti-estrogens (e.g., tamoxifen citrate, toremifene citrate, and the like), ER down-regulator (e.g., fulvestrant and the like), human menopausal gonadotrophin, follicle stimulating hormone, pill preparations, mepitiostane, testrolactone, aminoglutethimide, LH-RH agonists (e.g., goserelin acetate, buserelin, leuprorelin, and the like), droloxifene, epitiostanol, ethinylestradiol sulfonate, aromatase inhibitors (e.g., fadrozole hydrochloride, anastrozole, retrozole, exemestane, vorozole, formestane, and the like), anti-androgens (e.g., flutamide, bicartamide, nilutamide, and the like), 5α-reductase inhibitors (e.g., finasteride, dutasteride, epristeride, and the like), adrenocorticohormone drugs (e.g., dexamethasone, prednisolone, betamethasone, triamcinolone, and the like), androgen synthesis inhibitors (e.g., abiraterone, and the like), and retinoid and drugs that retard retinoid metabolism (e.g., liarozole, and the like), etc. and LH-RH agonists (e.g., goserelin acetate, buserelin, leuprorelin).

The non-drug therapy is exemplified by surgery, radiotherapy, gene therapy, thermotherapy, cryotherapy, laser cauterization, and the like, and any combinations thereof.

Formulation

Some embodiments provided herein describe a pharmaceutical composition, wherein the composition further comprises one or more pharmaceutical carriers, excipients, auxiliaries, binders and/or diluents. Pharmaceutical compositions are formulated in a conventional manner using one or more pharmaceutically acceptable inactive ingredients that facilitate processing of the active compounds into preparations that are used pharmaceutically. Proper formulation is dependent upon the route of administration chosen. A summary of pharmaceutical compositions described herein is found, for example, in Remington: The Science and Practice of Pharmacy. Nineteenth Ed (Easton, Pa.: Mack Publishing Company, 1995); Hoover, John E., Remington's Pharmaceutical Sciences, Mack Publishing Co., Easton, Pennsylvania 1975; Liberman, H. A. and Lachman, L., Eds., Pharmaceutical Dosage Forms, Marcel Decker, New York, N.Y., 1980; and Pharmaceutical Dosage Forms and Drug Delivery Systems. Seventh Ed. (Lippincott Williams & Wilkins 1999), herein incorporated by reference for such disclosure.

Any composition described herein optionally comprises minor amounts of non-toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins. In some embodiments, the composition further comprises one or more of lactose, dextrose, mannitol, pH buffering agents, antioxidant agents, preservative agents, tonicity adjusters or a combination thereof. Examples of pharmaceutically acceptable carriers that are optionally used include, but are not limited to aqueous vehicles, nonaqueous vehicles, antimicrobial agents, local anesthetics, suspending and dispersing agents, emulsifying agents, sequestering or chelating agents and other pharmaceutically acceptable substances.

In some embodiments, the compounds described herein exist as their pharmaceutically acceptable salts. In some embodiments, the methods disclosed herein include methods of treating diseases by administering such pharmaceutically acceptable salts. In some embodiments, the methods disclosed herein include methods of treating diseases by administering such pharmaceutically acceptable salts as pharmaceutical compositions.

In some embodiments, the compounds described herein possess acidic or basic groups and therefore react with any of a number of inorganic or organic bases, and inorganic and organic acids, to form a pharmaceutically acceptable salt. In some embodiments, these salts are prepared in situ during the final isolation and purification of the compounds of the invention, or by separately reacting a purified compound in its free form with a suitable acid or base, and isolating the salt thus formed.

Examples of pharmaceutically acceptable salts include those salts prepared by reaction of the compounds described herein with a mineral, organic acid or inorganic base, such salts including, acetate, acrylate, adipate, alginate, aspartate, benzoate, benzenesulfonate, bisulfate, bisulfite, bromide, butyrate, butyn-1,4-dioate, camphorate, camphorsulfonate, caproate, caprylate, chlorobenzoate, chloride, citrate, cyclopentanepropionate, decanoate, digluconate, dihydrogenphosphate, dinitrobenzoate, dodecylsulfate, ethanesulfonate, formate, fumarate, glucoheptanoate, glycerophosphate, glycolate, hemisulfate, heptanoate, hexanoate, hexyne-1,6-dioate, hydroxybenzoate, γ-hydroxybutyrate, hydrochloride, hydrobromide, hydroiodide, 2-hydroxyethanesulfonate, iodide, isobutyrate, lactate, maleate, malonate, methanesulfonate, mandelate metaphosphate, methanesulfonate, methoxybenzoate, methylbenzoate, monohydrogenphosphate, 1-napthalenesulfonate, 2-napthalenesulfonate, nicotinate, nitrate, palmoate, pectinate, persulfate, 3-phenylpropionate, phosphate, picrate, pivalate, propionate, pyrosulfate, pyrophosphate, propiolate, phthalate, phenylacetate, phenylbutyrate, propanesulfonate, salicylate, succinate, sulfate, sulfite, succinate, suberate, sebacate, sulfonate, tartrate, thiocyanate, tosylate undeconate and xylenesulfonate.

Further, the compounds described herein, in some embodiments, are prepared as pharmaceutically acceptable salts formed by reacting the free base form of the compound with a pharmaceutically acceptable inorganic or organic acid, including, but not limited to, inorganic acids such as hydrochloric acid, hydrobromic acid, sulfuric acid, nitric acid, phosphoric acid metaphosphoric acid, and the like; and organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, Q-toluenesulfonic acid, tartaric acid, trifluoroacetic acid, citric acid, benzoic acid, 3-(4-hydroxybenzoyl)benzoic acid, cinnamic acid, mandelic acid, arylsulfonic acid, methanesulfonic acid, ethanesulfonic acid, 1,2-ethanedisulfonic acid, 2-hydroxyethanesulfonic acid, benzenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid and muconic acid. In some embodiments, other acids, such as oxalic, while not in themselves pharmaceutically acceptable, are employed in the preparation of salts useful as intermediates in obtaining the compounds of the invention and their pharmaceutically acceptable acid addition salts.

In some embodiments, those compounds described herein which comprise a free acid group react with a suitable base, such as the hydroxide, carbonate, bicarbonate, sulfate, of a pharmaceutically acceptable metal cation, with ammonia, or with a pharmaceutically acceptable organic primary, secondary or tertiary amine. Representative alkali or alkaline earth salts include the lithium, sodium, potassium, calcium, magnesium, and aluminum salts and the like. Illustrative examples of bases include sodium hydroxide, potassium hydroxide, choline hydroxide, sodium carbonate, N+(C1-4alkyl)4, and the like.

Representative organic amines useful for the formation of base addition salts include ethylamine, diethylamine, ethylenediamine, ethanolamine, diethanolamine, piperazine and the like. It should be understood that the compounds described herein also include the quaternization of any basic nitrogen-containing groups they contain. In some embodiments, water or oil-soluble or dispersible products are obtained by such quaternization. The compounds described herein can be prepared as pharmaceutically acceptable salts formed when an acidic proton present in the parent compound either is replaced by a metal ion, for example an alkali metal ion, an alkaline earth ion, or an aluminum ion; or coordinates with an organic base. Base addition salts are be prepared by reacting the free acid form of the compounds described herein with a pharmaceutically acceptable inorganic or organic base, including, but not limited to organic bases such as ethanolamine, diethanolamine, triethanolamine, tromethamine, N-methylglucamine, and the like and inorganic bases such as aluminum hydroxide, calcium hydroxide, potassium hydroxide, sodium carbonate, sodium hydroxide, and the like. In addition, the salt forms of the disclosed compounds can be prepared using salts of the starting materials or intermediates.

In some embodiments, the compounds described herein are administered either alone or in combination with pharmaceutically acceptable carriers, excipients or diluents, in a pharmaceutical composition. Administration of the compounds and compositions described herein can be effected by any method that enables delivery of the compounds to the site of action. These methods include, though are not limited to delivery via enteral routes (including oral, gastric or duodenal feeding tube, rectal suppository and rectal enema), parenteral routes (injection or infusion, including intraarterial, intracardiac, intradermal, intraduodenal, intramedullary, intramuscular, intraosseous, intraperitoneal, intrathecal, intravascular, intravenous, intravitreal, epidural and subcutaneous), inhalational, transdermal, transmucosal, sublingual, buccal and topical (including epicutaneous, dermal, enema, eye drops, ear drops, intranasal, vaginal) administration, although the most suitable route may depend upon for example the condition and disorder of the recipient. By way of example only, compounds described herein can be administered locally to the area in need of treatment, by for example, local infusion during surgery, topical application such as creams or ointments, injection, catheter, or implant. The administration can also be by direct injection at the site of a diseased tissue or organ.

In some embodiments, pharmaceutical compositions suitable for oral administration are presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. In some embodiments, the active ingredient is presented as a bolus, electuary or paste.

Pharmaceutical compositions which can be used orally include tablets, push-fit capsules made of gelatin, as well as soft, sealed capsules made of gelatin and a plasticizer, such as glycerol or sorbitol. Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with an inert liquid diluent. In some embodiments, the tablets are coated or scored and are formulated so as to provide slow or controlled release of the active ingredient therein. Tablets contain the active ingredient in admixture with non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, such as microcrystalline cellulose, sodium crosscarmellose, corn starch, or alginic acid; binding agents, for example starch, gelatin, polyvinyl-pyrrolidone or acacia, and lubricating agents, for example, magnesium stearate, stearic acid or talc. The tablets may be un-coated or coated by known techniques to mask the taste of the drug or delay disintegration and absorption in the gastrointestinal tract and thereby provide a sustained action over a longer period. For example, a water soluble taste masking material such as hydroxypropylmethyl-cellulose or hydroxypropylcellulose, or a time delay material such as ethyl cellulose, or cellulose acetate butyrate may be employed as appropriate. Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water soluble carrier such as polyethyleneglycol or an oil medium, for example peanut oil, liquid paraffin, or olive oil.

All formulations for oral administration should be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In some embodiments, stabilizers are added. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or Dragee coatings for identification or to characterize different combinations of active compound doses.

In some embodiments, pharmaceutical compositions are formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. The compositions may be presented in unit-dose or multi-dose containers, for example sealed ampoules and vials, and may be stored in powder form or in a freeze-dried (lyophilized) condition requiring only the addition of the sterile liquid carrier, for example, saline or sterile pyrogen-free water, immediately prior to use. Extemporaneous injection solutions and suspensions may be prepared from sterile powders, granules and tablets of the kind previously described.

Pharmaceutical compositions for parenteral administration include aqueous and non-aqueous (oily) sterile injection solutions of the active compounds which may contain antioxidants, buffers, bacteriostats and solutes which render the formulation isotonic with the blood of the intended recipient, and aqueous and non-aqueous sterile suspensions which may include suspending agents and thickening agents. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Pharmaceutical compositions may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example, as an emulsion in an acceptable oil) or ion exchange resins, or as sparingly soluble derivatives, for example, as a sparingly soluble salt.

For buccal or sublingual administration, the compositions may take the form of tablets, lozenges, pastilles, or gels formulated in conventional manner. Such compositions may comprise the active ingredient in a flavored basis such as sucrose and acacia or tragacanth.

Pharmaceutical compositions may also be formulated in rectal compositions such as suppositories or retention enemas, e.g., containing conventional suppository bases such as cocoa butter, polyethylene glycol, or other glycerides.

Pharmaceutical compositions may be administered topically, that is by non-systemic administration. This includes the application of a compound of the present invention externally to the epidermis or the buccal cavity and the instillation of such a compound into the ear, eye and nose, such that the compound does not significantly enter the blood stream. In contrast, systemic administration refers to oral, intravenous, intraperitoneal and intramuscular administration.

Pharmaceutical compositions suitable for topical administration include liquid or semi-liquid preparations suitable for penetration through the skin to the site of inflammation such as gels, liniments, lotions, creams, ointments or pastes, and drops suitable for administration to the eye, ear or nose. The active ingredient may comprise, for topical administration, from 0.001% to 10% w/w, for instance from 1% to 2% by weight of the formulation.

Pharmaceutical compositions for administration by inhalation are conveniently delivered from an insufflator, nebulizer pressurized packs or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Alternatively, for administration by inhalation or insufflation, pharmaceutical preparations may take the form of a dry powder composition, for example a powder mix of the compound and a suitable powder base such as lactose or starch. The powder composition may be presented in unit dosage form, in for example, capsules, cartridges, gelatin or blister packs from which the powder may be administered with the aid of an inhalator or insufflator.

Aqueous suspensions contain the active material in admixture with excipients suitable for the manufacture of aqueous suspensions. Such excipients are suspending agents, for example sodium carboxymethylcellulose, methylcellulose, hydroxypropylmethyl-cellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose, saccharin or aspartame.

Suitable pharmaceutical carriers include inert diluents or fillers, water and various organic solvents. In some embodiments, the pharmaceutical composition contains additional ingredients such as flavorings, binders, excipients and the like. Thus for oral administration, tablets containing various excipients, such as citric acid are employed together with various disintegrants such as starch, alginic acid and certain complex silicates and with binding agents such as sucrose, gelatin and acacia. Additionally, lubricating agents such as magnesium stearate, sodium lauryl sulfate and talc are often useful for tableting purposes. In other embodiments, solid compositions of a similar type are employed in soft and hard filled gelatin capsules. Preferred materials, therefore, include lactose or milk sugar and high molecular weight polyethylene glycols. In certain embodiments where aqueous suspensions or elixirs are desired for oral administration, the active compound therein is combined with various sweetening or flavoring agents, coloring matters or dyes and, if desired, emulsifying agents or suspending agents, together with diluents such as water, ethanol, propylene glycol, glycerin, or combinations thereof.

In some embodiments, oily suspensions are formulated by suspending the active ingredient in a vegetable oil, for example arachis oil, olive oil, sesame oil or coconut oil, or in mineral oil such as liquid paraffin. In certain embodiments, the oily suspensions contain a thickening agent, for example beeswax, hard paraffin or cetyl alcohol. In further or additional embodiments, sweetening agents such as those set forth above, and flavoring agents are added to provide a palatable oral preparation. In other embodiments, these compositions are preserved by the addition of an anti-oxidant such as butylated hydroxyanisol or alpha-tocopherol.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. In some embodiments, additional excipients, for example sweetening, flavoring and coloring agents, are also present. In further or additional embodiments, these compositions are preserved by the addition of an anti-oxidant such as ascorbic acid.

In some embodiments, pharmaceutical compositions are in the form of oil-in-water emulsions. In some embodiments, the oily phase is a vegetable oil, for example olive oil or arachis oil, or a mineral oil, for example liquid paraffin or mixtures of these. Suitable emulsifying agents include but are not limited to naturally-occurring phosphatides, for example soy bean lecithin, and esters or partial esters derived from fatty acids and hexitol anhydrides, for example sorbitan monooleate, and condensation products of the said partial esters with ethylene oxide, for example polyoxyethylene sorbitan monooleate. In further or additional embodiments, the emulsions contain sweetening agents, flavoring agents, preservatives and antioxidants.

In some embodiments, pharmaceutical compositions described herein are in the form of a sterile injectable aqueous solution. Acceptable vehicles and solvents that are employed include but are not limited to water, Ringer's solution, phosphate buffered saline solution, U.S.P. and isotonic sodium chloride solution, ethanol, and 1,3-butanediol.

In addition, sterile, fixed oils are optionally employed as a solvent or suspending medium. For this purpose any bland fixed oil is optionally employed including synthetic mono- or diglycerides. Suitable lipophilic solvents or vehicles include fatty oils such as sesame oil, or synthetic fatty acid esters, such as ethyl oleate or triglycerides, or liposomes or other microparticulate systems may be used to target the agent to blood components or one or more organs. In some embodiments, the sterile injectable preparation is a sterile injectable oil-in-water microemulsion where the active ingredient is dissolved in the oily phase. In certain embodiments, the active ingredient is first dissolved in a mixture of soybean oil and lecithin. The oil solution then introduced into a water and glycerol mixture and processed to form a microemulsion. In further or additional embodiments, the injectable solutions or microemulsions are introduced into an individual's blood-stream by local bolus injection. Alternatively, in some embodiments, it is advantageous to administer the solution or microemulsion in such a way as to maintain a constant circulating concentration of the instant compound. In order to maintain such a constant concentration, a continuous intravenous delivery device are utilized. An example of such a device is the Deltec CADD-PLUS™ model 5400 intravenous pump.

In other embodiments, the pharmaceutical composition is in the form of a sterile injectable aqueous or oleagenous suspension for intramuscular and subcutaneous administration. In further or additional embodiments, this suspension is formulated using those suitable dispersing or wetting agents and suspending agents which have been mentioned above. In some embodiments, the sterile injectable preparation is a sterile injectable solution or suspension in a non-toxic parenterally-acceptable diluent or solvent, for example as a solution in 1,3-butanediol. In addition, sterile, fixed oils are conventionally employed as a solvent or suspending medium. For this purpose in some embodiments, any bland fixed oil is optionally employed including synthetic mono- or diglycerides. In addition, fatty acids such as oleic acid find use in the preparation of injectables.

In certain embodiments, pharmaceutical compositions are administered in the form of suppositories for rectal administration of the drug. These compositions are prepared by mixing the active ingredient with a suitable non-irritating excipient which is solid at ordinary temperatures but liquid at the rectal temperature and will therefore melt in the rectum to release the drug. Such materials include cocoa butter, glycerinated gelatin, hydrogenated vegetable oils, mixtures of polyethylene glycols of various molecular weights and fatty acid esters of polyethylene glycol.

In some embodiments, the compounds or compositions described herein are delivered in a vesicle, such as a liposome. In further or alternative embodiments, the compounds and pharmaceutical compositions described herein are delivered in a controlled release system, or a controlled release system can be placed in proximity of the therapeutic target. In one embodiment, a pump is used.

For topical use, creams, ointments, jellies, solutions or suspensions, etc., containing an active agent is used. As used herein, topical application includes mouth washes and gargles.

In certain embodiments, pharmaceutical compositions are administered in intranasal form via topical use of suitable intranasal vehicles and delivery devices, or via transdermal routes, using transdermal skin patches. To be administered in the form of a transdermal delivery system, the dosage administration will be continuous rather than intermittent throughout the dosage regimen.

In some embodiments, the pharmaceutical composition described herein further comprises a cyclodextrin. In some embodiments, the cyclodextrin has a concentration (w/v) ranging from about 0.001% to about 50%. In other embodiments, the cyclodextrin has a concentration (w/v) ranging from about 2% to about 48%. In other embodiments, the cyclodextrin has a concentration (w/v) ranging from about 4% to about 45%. In other embodiments, the cyclodextrin has a concentration (w/v) ranging from about 10% to about 43%. In other embodiments, the cyclodextrin has a concentration (w/v) ranging from about 15% to about 40%. In other embodiments, the cyclodextrin has a concentration (w/v) ranging from about 20% to about 38%. In other embodiments, the cyclodextrin has a concentration (w/v) ranging from about 22% to about 37%. In other embodiments, the cyclodextrin has a concentration (w/v) ranging from about 25% to about 35%. In a preferred embodiment, the cyclodextrin has a concentration (w/v) ranging from about 28% to about 32%.

Some embodiments described herein provide a composition further comprising cyclodextrin, wherein the cyclodextrin has a concentration (w/v) of about 15%, 18%, 20%, 22%, 25%, 26%, 27%, 28%, 29%, 30%, 31%, 32%, 33%, 34%, 35%, 36%, 37%, or 38% when cyclodextrin derivative is SBE7-β-CD (Captisol®). In one embodiment, the cyclodextrin has a concentration (w/v) of about 30° % when cyclodextrin derivative is SBE7-β-CD (Captisol®). In another embodiment, the solubility enhancer has a concentration (w/v) of about 29.4% when the cyclodextrin derivative is SBE7-β-CD (Captisol®).

Additional cyclodextrin derivatives suitable for use in intravenous compositions described herein are known in the art and are described in, e.g., U.S. Pat. Nos. 5,134,127 and 5,376,645 each of which is incorporated by reference herein for such disclosure. In addition, examples of suitable cyclodextrin derivatives are described below.

Suitable cyclodextrins and derivatives useful in certain embodiments of the compositions, methods and kits described herein include, for example, those described in Challa et al., AAPS PharmSciTech 6(2): E329-E357 (2005), U.S. Pat. Nos. 5,134,127, 5,376,645, 5,874,418, each of which is incorporated by reference herein for such disclosure. In some embodiments, suitable cyclodextrins or cyclodextrin derivatives for use in certain embodiments of the compositions, methods and kits described herein include, but are not limited to, α-cyclodextrins, β-cyclodextrins, γ-cyclodextrins, SAE-CD derivatives (e.g., SBE-α-CD, SBE-β-CD, SBE1-β-CD, SBE4-β-CD, SBE7-β-CD (Captisol®), and SBE-γ-CD) (Cydex, Inc. Lenexa, KS), hydroxyethyl, hydroxypropyl (including 2- and 3-hydroxypropyl) and dihydroxypropyl ethers, their corresponding mixed ethers and further mixed ethers with methyl or ethyl groups, such as methylhydroxyethyl, ethyl-hydroxyethyl and ethyl-hydroxypropyl ethers of α-, β- and γ-cyclodextrin; and the maltosyl, glucosyl and maltotriosyl derivatives of α-, β- and γ-cyclodextrin, which may contain one or more sugar residues, e. g. glucosyl or diglucosyl, maltosyl or dimaltosyl, as well as various mixtures thereof, e. g. a mixture of maltosyl and dimaltosyl derivatives. Specific cyclodextrin derivatives for use herein include hydroxypropyl-β-cyclodextrin, hydroxyethyl-β-cyclodextrin, hydroxypropyl-γ-cyclodextrin, hydroxyethyl-γ-cyclodextrin, dihydroxypropyl-β-cyclodextrin, glucosyl-α-cyclodextrin, glucosyl-β-cyclodextrin, diglucosyl-β-cyclodextrin, maltosyl-α-cyclodextrin, maltosyl-β-cyclodextrin, maltosyl-γ-cyclodextrin, maltotriosyl-β-cyclodextrin, maltotriosyl-γ-cyclodextrin, dimaltosyl-β-cyclodextrin, diethyl-β-cyclodextrin, glucosyl-α-cyclodextrin, glucosyl-β-cyclodextrin, diglucosyl-β-cyclodextrin, tri-O-methyl-β-cyclodextrin, tri-O-ethyl-β-cyclodextrin, tri-O-butyryl-β-cyclodextrin, tri-O-valeryl-β-cyclodextrin, and di-O-hexanoyl-β-cyclodextrin, as well as methyl-β-cyclodextrin, and mixtures thereof such as maltosyl-β-cyclodextrin/dimaltosyl-β-cyclodextrin. Any suitable procedure may be utilized for preparing such cyclodextrins including, e.g., those procedures described in U.S. Pat. No. 5,024,998, which is incorporated by reference herein for such disclosure. Other cyclodextrins suitable for use in certain embodiments of the compositions, methods and kits described herein include the carboxyalkyl thioether derivatives such as ORG 26054 and ORG 25969 by ORGANON (AKZO-NOBEL), hydroxybutenyl ether derivatives by EASTMAN, sulfoalkyl-hydroxyalkyl ether derivatives, sulfoalkyl-alkyl ether derivatives, and other derivatives, for example as described in U.S. Patent Application Nos. 2002/0128468, 2004/0106575, 2004/0109888, and 2004/0063663, or U.S. Pat. Nos. 6,610,671, 6,479,467, 6,660,804, or 6,509,323, each of which is specifically incorporated by reference herein for such disclosure.

Hydroxypropyl-β-cyclodextrin can be obtained from Research Diagnostics Inc. (Flanders, NJ). Exemplary hydroxypropyl-β-cyclodextrin products include Encapsin® (degree of substitution ~4) and Molecusol® (degree of substitution ~8); however, embodiments including other degrees of substitution are also available and are within the scope of the present invention.

Dimethyl cyclodextrins are available from FLUKA Chemie (Buchs, CH) or Wacker (Iowa). Other derivatized cyclodextrins suitable for use in the invention include water soluble derivatized cyclodextrins. Exemplary water-soluble derivatized cyclodextrins include carboxylated derivatives; sulfated derivatives; alkylated derivatives; hydroxyalkylated derivatives; methylated derivatives; and carboxy-D-cyclodextrins, e. g., succinyl-D-cyclodextrin (SCD). All of these materials can be made according to methods known in the art and/or are available commercially. Suitable derivatized cyclodextrins are disclosed in Modified Cyclodextrins: Scaffolds and Templates for Supramolecular Chemistry (Eds. Christopher J. Easton, Stephen F. Lincoln, Imperial College Press, London, U K, 1999) and New Trends in Cyclodextrins and Derivatives (Ed. Dominique Duchene, Editions de Sante, Paris, France, 1991).

Dosing and Treatment Regiments

In one embodiment, the inhibitors and agents described herein, or a pharmaceutically acceptable salt thereof, are used in the preparation of medicaments for the treatment of diseases or conditions. Methods for treating any of the diseases or conditions described herein in an individual in need of such treatment, involves administration of pharmaceutical compositions described herein to said individual.

In certain embodiments, the compositions described herein are administered for prophylactic and/or therapeutic treatments. In certain therapeutic applications, the compositions are administered to a patient already suffering from a disease or condition, in an amount sufficient to cure or at least partially arrest at least one of the symptoms of the disease or condition. Amounts effective for this use depend on the severity and course of the disease or condition, previous therapy, the patient's health status, weight, and response to the drugs, and the judgment of the treating physician. Therapeutically effective amounts are optionally determined by methods including, but not limited to, a dose escalation and/or dose ranging clinical trial.

In prophylactic applications, compositions containing the compounds described herein are administered to a patient susceptible to or otherwise at risk of a particular disease, disorder or condition. Such an amount is defined to be a "prophylactically effective amount or dose." In this use, the precise amounts also depend on the patient's state of health, weight, and the like. When used in patients, effective amounts for this use will depend on the severity and course of the disease, disorder or condition, previous therapy, the patient's health status and response to the drugs, and the judgment of the treating physician. In one aspect, prophylactic treatments include administering to a mammal, who previously experienced at least one symptom of the disease being treated and is currently in remission, a pharmaceutical composition comprising a compound described herein, or a pharmaceutically acceptable salt thereof, in order to prevent a return of the symptoms of the disease or condition.

In certain embodiments wherein the patient's condition does not improve, upon the doctor's discretion the administration of the compounds are administered chronically, that is, for an extended period of time, including throughout the duration of the patient's life in order to ameliorate or otherwise control or limit the symptoms of the patient's disease or condition.

In certain embodiments wherein a patient's status does improve, the dose of drug being administered is temporarily reduced or temporarily suspended for a certain length of time (i.e., a "drug holiday"). In specific embodiments, the length of the drug holiday is between 1 day and 1 year, including by way of example only, 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 28 days, 35 days, 50 days, 70 days, 100 days, 120 days, 150 days, 180 days, 200 days, 250 days, 280 days, 300 days, 320 days, 350 days, or 365 days. The dose reduction during a drug holiday is, by way of example only, by 10%-100%, including by way of example only 10%, 15%, 20%, 25%, 30%, 35%, 40%, 45%, 50%, 55%, 60%, 65%, 70%, 75%, 80%, 85%, 90%, 95%, and 100%.

Once improvement of the patient's conditions has occurred, a maintenance dose is administered if necessary. Subsequently, in specific embodiments, the dosage or the frequency of administration, or both, is reduced, as a function of the symptoms, to a level at which the improved disease, disorder or condition is retained. In certain embodiments, however, the patient requires intermittent treatment on a long-term basis upon any recurrence of symptoms.

The amount of a given agent that corresponds to such an amount varies depending upon factors such as the particular compound, disease condition and its severity, the identity (e.g., weight, sex) of the subject or host in need of treatment, but nevertheless is determined according to the particular circumstances surrounding the case, including, e.g., the specific agent being administered, the route of administration, the condition being treated, and the subject or host being treated.

The daily dosages appropriate for the active agents are from about 0.1 mg to about 3000 mg, conveniently administered in divided doses, including, but not limited to, up to four times a day or in extended release form. Suitable unit dosage forms for oral administration include from about 0.1 to 1000 mg active ingredient, from about 0.1 to 500 mg active ingredient, from about 1 to 250 mg of active ingredient, from about 1 to about 100 mg active ingredient, from about 1 to about 75 mg active ingredient, from about 1 to about 50 mg active ingredient, from about 1 to about 30 mg active ingredient, from about 1 to about 20 mg active ingredient, or from about 1 to about 10 mg active ingredient. Such dosages are optionally altered depending on a number of variables, not limited to the activity of the compound used, the mode of administration, the requirements of an individual, the severity of the disease or condition being treated, and the judgment of the practitioner. In one embodiment, the desired dose is conveniently presented in a single dose or in divided doses administered simultaneously or at appropriate intervals, for example as two, three, four or more sub-doses per day.

In one embodiment, the dosages appropriate for the compound described herein, or a pharmaceutically acceptable salt thereof, are from about 0.01 to about 50 mg/kg per body weight. In some embodiments, the dosage or the amount of active in the dosage form are lower or higher than the ranges indicated herein, based on a number of variables in regard to an individual treatment regime. In various embodiments, the unit dosages are altered depending on a number of variables including, but not limited to, the activity of the compound used, the disease or condition to be treated, the mode of administration, the requirements of the individual subject, the severity of the disease or condition being treated, and the judgment of the practitioner.

In some embodiments, the dosage of the oxidative phosphorylation inhibitor (e.g., benzopyran derivative), or pharmaceutically acceptable salt thereof, is about 5 mg/kg to about 30 mg/kg, e.g., about 25 mg/kg, about 20 mg/kg, about 15 mg/kg, or about 10 mg/kg. In some instances, the dosage of the oxidative phosphorylation inhibitor is reduced to a level at which the oxidative phosphorylation inhibitor is efficacious in combination with the glycolytic inhibitor. In some embodiments, the reduced dosage is about 0.5 mg/kg to about 10 mg/kg, e.g., about: 9 mg/kg, 8 mg/kg, 7 mg/kg, 6 mg/kg, 5 mg/kg, 4 mg/kg, 3 mg/kg, 2 mg/kg, or 1 mg/kg. In certain embodiments, the reduced dosage is about 5 mg/kg. In some embodiments, the frequency of administration of the oxidative phosphorylation inhibitor is reduced, either independently of, or in conjunction with, reduction in the dosage of the oxidative phosphorylation inhibitor.

In some embodiments, the dosage of sorafenib (Nexavar) is 400 mg twice a day. In some embodiments, the dosage of sunitinib (Sutent) is 50 mg daily for 4 weeks, followed by 2 weeks off. In some embodiments, the dosage of pazopanib is 800 mg daily. In some embodiments, the dosage of axitinib is 5 mg twice daily. In some instances, the maintenance dosage of axitinib is 2 to 10 mg twice daily. In some embodiments, the dosage of regorafenib is 160 mg once daily for 21 days for each 28 day cycle. In some embodiments, the dosage of cabozantinib is 140 mg once daily. In some embodiments, the dosage of temsirolimus is 25 mg IV infusion over a 30 to 60 minute period once a week. In some embodiments, the dosage of everolimus is 10 mg daily. In some embodiments, the dosage of erlotinib is 150 mg daily. In some embodiments, the dosage of nintedanib is 150 mg. In some embodiments, the dosage of nintedanib is 150 mg twice daily. In some embodiments, the dosage of dovitinib is about 500 mg/kg 5 days on and 2 days off in 28 day cycles. In some embodiments, the dosage of dovitinib is about 250 mg/kg 5 days on and 2 days off in 28 day cycles. In some embodiments, the dosage of dovitinib is about 400 mg/kg 5 days on and 2 days off in 28 day cycles.

In any of the aforementioned aspects are further embodiments in which the effective amount of the compound described herein, or a pharmaceutically acceptable salt thereof, is: (a) systemically administered to the individual; and/or (b) administered orally to the individual; and/or (c) intravenously administered to the individual; and/or (d) administered by injection to the individual; and/or (e) administered topically to the individual, and/or (f) administered non-systemically or locally to the individual.

In any of the aforementioned aspects are further embodiments comprising multiple administrations of the effective amount of the compound, including further embodiments in which (i) the compound is administered continuously or intermittently: as in a single dose; (ii) the time between multiple administrations is every 6 hours; (iii) the compound is administered to the individual every 8 hours; (iv) the compound is administered to the individual every 12 hours; (v) the compound is administered to the individual every 24 hours. In further or alternative embodiments, the method comprises a drug holiday, wherein the administration of the compound is temporarily suspended or the dose of the compound being administered is temporarily reduced; at the end of the drug holiday, dosing of the compound is resumed. In one embodiment, the length of the drug holiday varies from 1 day to 1 year.

In some embodiments, the oxidative phosphorylation inhibitor (e.g., benzopyran derivative), or pharmaceutically acceptable salt thereof, is administered to a subject three times per week and the glycolytic inhibitor is administered to the subject 5 days per week (e.g., Monday through Friday).

In some embodiments, the pharmaceutical compositions described herein are in unit dosage forms suitable for single administration of precise dosages. In unit dosage form, the formulation is divided into unit doses containing appropriate quantities of one or more active ingredient. In some embodiments, the unit dosage is in the form of a package containing discrete quantities of the formulation. Non-limiting examples are packaged tablets or capsules, and powders in vials or ampoules. In some embodiments, aqueous suspension compositions are packaged in single-dose non-reclosable containers. Alternatively, multiple-dose reclosable containers are used, in which case it is typical to include a preservative in the composition. By way of example only, formulations for parenteral injection are presented in unit dosage form, which include, but are not limited to ampoules, or in multi dose containers, with an added preservative.

Some embodiments described herein provide a pharmaceutical composition comprising a compound of formula (I), (II), (III), or (IV), or an enantiomer thereof, as described herein, for use in combination with a pharmaceutical composition comprising a glycolytic inhibitor, as described herein, for the treatment of a disease or disorder associated with dysregulation of cell proliferation, as described herein.

Some embodiments described herein provide a pharmaceutical composition comprising a compound of formula (I), (II), (III), or (IV), or an enantiomer thereof, as described herein, and a glycolytic inhibitor, as described herein, for the treatment of a disease or disorder associated with dysregulation of cell proliferation, as described herein.

Some embodiments provide a pharmaceutical composition comprising a glycolytic inhibitor for use in combination with a pharmaceutical composition comprising a compound of (I), (II), (III), or (IV), or an enantiomer thereof, as described herein, for the treatment of a disease or disorder associated with dysregulation of cell proliferation, as described herein.

Some preferred embodiments include a pharmaceutical composition comprising a compound of formula (I), (II), (III), or (IV) for use in combination with a pharmaceutical composition comprising a glycolytic inhibitor, as described herein, for the treatment of a disease or disorder associated with dysregulation of cell proliferation, as described herein. In some preferred embodiments, there is provided a pharmaceutical composition comprising d-cis-3-(4-hydroxyphenyl)-4-(4-hydroxyphenyl)-8-methylchroman-7-ol for use in combination with a pharmaceutical composition comprising a glycolytic inhibitor, as described herein, for the treatment of a disease or disorder associated with dysregulation of cell proliferation, as described herein. In some embodiments, the glycolytic inhibitor is a hexokinase, a lactic dehydrogenase inhibitor, a glucose-6-phosphate dehydrogenase inhibitor or an angiogenesis inhibitor, as described herein.

Some preferred embodiments include a pharmaceutical composition comprising a compound of formula (I), (II), (III), or (IV) and a glycolytic inhibitor, as described herein, for the treatment of a disease or disorder associated with dysregulation of cell proliferation, as described herein. In some preferred embodiments, the pharmaceutical composition comprises d-cis-3-(4-hydroxyphenyl)-4-(4-hydroxyphenyl)-8-methylchroman-7-ol and a glycolytic inhibitor, as described herein. In some embodiments, the glycolytic inhibitor is a hexokinase, a lactic dehydrogenase inhibitor, a glucose-6-phosphate dehydrogenase inhibitor or an angiogenesis inhibitor, as described herein. In some embodiments, the angiogenesis inhibitor is nintedanib (BIBF 1120).

Some preferred embodiments include a pharmaceutical composition comprising a hexokinase, a lactic dehydrogenase inhibitor, a glucose-6-phosphate dehydrogenase inhibitor or an angiogenesis inhibitor, as described herein, for use in combination with a pharmaceutical composition comprising a compound of formula (I), (II), (III), or (IV), as described herein, for the treatment of a disease or disorder associated with dysregulation of cell proliferation, as described herein. In some preferred embodiments, there is provided a pharmaceutical composition comprising a hexokinase, a lactic dehydrogenase inhibitor, a glucose-6-phosphate dehydrogenase inhibitor or an angiogenesis inhibitor, as described herein, for use in combination with a pharmaceutical composition comprising d-cis-3-(4-hydroxyphenyl)-4-(4-hydroxyphenyl)-8-methylchroman-7-ol for the treatment of a disease or disorder associated with dysregulation of cell proliferation, as described herein. In certain embodiments, there is provided a pharmaceutical composition comprising a hexokinase, a lactic dehydrogenase inhibitor, a glucose-6-phosphate dehydrogenase inhibitor or an angiogenesis inhibitor in combination with a pharmaceutical composition comprising a d-isomer of a compound of formula (I), (II), (III), or (IV), as described herein, in at least, or greater than, 50%, 55%, 60%, 65%, 70%, 75%, 80%, 85%, 88%, 90%, 91%, 92%, 93%, 94%, 95%, 96%, 97%, 98%, 99%, 99.5%, or 99.9% enantiomeric excess for treatment of a disease or disorder associated with dysregulation of cell proliferation, as described herein. In certain embodiments, there is provided a pharmaceutical composition comprising a hexokinase, a lactic dehydrogenase inhibitor, a glucose-6-phosphate dehydrogenase inhibitor or an angiogenesis inhibitor, as described herein, for combination with a pharmaceutical composition comprising d-cis-3-(4-hydroxyphenyl)-4-(4-hydroxyphenyl)-8-methylchroman-7-ol in at least, or greater than, 50%, 55%, 60%, 65%, 70%, 75%, 80%, 85%, 88%, 90%, 91%, 92%, 93%, 94%, 95%, 96%, 97%, 98%, 99%, 99.5%, or 99.9% enantiomeric excess for treatment of a disease or disorder associated with dysregulation of cell proliferation, as described herein. In some embodiments the glycolytic inhibitor is nintedanib (BIBF 1120).

Some embodiments described herein provide use of a compound of formula (I), (II), (III), or (IV), or an enantiomer thereof, as described herein, for the manufacture of a medicament for use in combination with a pharmaceutical composition comprising a glycolytic inhibitor, as described herein, for the treatment of a disease or disorder associated with dysregulation of cell proliferation, as described herein. In some embodiments, the angiogenesis inhibitor is nintedanib (BIBF 1120).

Some embodiments described herein provide use of a compound of formula (I), (II), (III), or (IV), or an enantiomer thereof, as described herein, and a glycolytic inhibitor, for the manufacture of a medicament for use in the treatment of a disease or disorder associated with dysregulation of cell proliferation, as described herein.

Some embodiments described herein provide use of a glycolytic inhibitor for the manufacture of a medicament for use in combination with a pharmaceutical composition comprising a compound of (I), (II), (III), or (IV), or an enantiomer thereof, as described herein, for the treatment of a disease or disorder associated with dysregulation of cell proliferation, as described herein.

Some preferred embodiments include use of a a compound of formula (I), (II), (III), or (IV) for manufacture of a medicament for use in combination with a pharmaceutical composition comprising a glycolytic inhibitor, as described herein, for the treatment of a disease or disorder associated with dysregulation of cell proliferation, as described herein. The medicament comprises d-cis-3-(4-hydroxyphenyl)-4-(4-hydroxyphenyl)-8-methylchroman-7-ol. In some embodiments, the glycolytic inhibitor is a hexokinase, a lactic dehydrogenase inhibitor, a glucose-6-phosphate dehydrogenase inhibitor or an angiogenesis inhibitor, as described herein. In some embodiments, the angiogenesis inhibitor is nintedanib (BIBF 1120).

Some preferred embodiments include use of a hexokinase, a lactic dehydrogenase inhibitor, a glucose-6-phosphate dehydrogenase inhibitor or an angiogenesis inhibitor, as described herein, in the manufacture of a medicament for use in combination with a pharmaceutical composition comprising a compound of formula (I), (II), (III), or (IV), as described herein, for the treatment of a disease or disorder associated with dysregulation of cell proliferation, as described herein. In some preferred embodiments, the medicament is for use in combination with a pharmaceutical composition comprising d-cis-3-(4-hydroxyphenyl)-4-(4-hydroxyphenyl)-8-methylchroman-7-ol for the treatment of a disease or disorder associated with dysregulation of cell proliferation, as described herein. In certain embodiments, the medicament comprises a hexokinase, a lactic dehydrogenase inhibitor, a glucose-6-phosphate dehydrogenase inhibitor or an angiogenesis inhibitor for use in combination with a pharmaceutical composition comprising a d-isomer of a compound of formula (I), (II), (III), or (IV), as described herein, in at least, or greater than, 50%, 55%, 60%, 65%, 70%, 75%, 80%, 85%, 88%, 90%, 91%, 92%, 93%, 94%, 95%, 96%, 97%, 98%, 99%, 99.5%, or 99.9% enantiomeric excess for treatment of a disease or disorder associated with dysregulation of cell proliferation, as described herein. In certain embodiments, the medicament comprising a hexokinase, a lactic dehydrogenase inhibitor, a glucose-6-phosphate dehydrogenase inhibitor or an angiogenesis inhibitor, as described herein, is for use in combination with a pharmaceutical composition comprising d-cis-3-(4-hydroxyphenyl)-4-(4-hydroxyphenyl)-8-methylchroman-7-ol in at least, or greater than, 50%, 55%, 60%, 65%, 70%, 75%, 80%, 85%, 88%, 90%, 91%, 92%, 93%, 94%, 95%, 96%, 97%, 98%, 99%, 99.5%, or 99.9% enantiomeric excess for treatment of a disease or disorder associated with dysregulation of cell proliferation, as described herein. In some embodiments, the angiogenesis inhibitor is nintedanib (BIBF 1120).

EXAMPLES

The following examples are provided for illustrative purposes only and not to limit the scope of the claims provided herein.

Materials and Methods

Mouse Models. PyMT [FVB/NTg(MMTV–PyVT)$^{634Mul/}$$_J$]mice were obtained from W. Muller (McMaster University, Ontario, Canada). C57BL/6JOlaHsd were obtained from the CNIO Animal House (Madrid, Spain). Four- to 6-week-old female athymic nude mice (Hsd: Athymic Nude-Foxn1nu) were purchased from Charles River Laboratories (Spain). Pulm24 PDX was kindly provided by Dr. Manuel Hidalgo. Tumors were implanted subcutaneously in the lower back of Athymic Nude-Foxn1nu, and mouse-mouse passages were performed to obtain the experimental animal cohorts.

Animal Treatments. The treatment allocations were randomly assigned using computer-generated random numbers (www.randomization.com). The researcher performing tumor measurements was blinded to the treatment allocation. Treatment started with the different drugs at 7 weeks of age (T0). The animals were treated on a continuous schedule, as in a clinical setting. The adaptive changes occurring during treatment were monitored along a time course: T0, T1 (week 1 of treatment), and Tend. The efficacy parameter under study was tumor growth inhibition (TGI) at the time when vehicle treated animals reached the euthanization humane endpoint (Tend).

Nintedanib (BIBF) and regorafenib (Rego) were administered at 85 and 10 mg/kg/d, respectively, by oral gavage Monday through Friday. Compound 5 (ME) was administered at 50 mg/kg intraperitoneally three times per week. Dovitinib (Dovi) was freshly prepared in pH 2.5 water and administered by oral gavage at 40 mg/kg/d Monday through Friday.

Tumor measurements and treatment combinations effects. Tumor dimensions were measured once per week using calipers. Tumor volumes were calculated using the formula V=(D×d2)/2 mm3, where D is the largest diameter and d is the shortest diameter; all measurements were in millimeters. All tumors arising in mammary glands were measured in each animal. To calculate TGI, we used the following formula: TGI=[1−(TF/T0)A/(TF/T0)V]×100, where TF is the time point analyzed, T0 is the initial time, A is the corresponding drug, and V is the vehicle.

For treatment combinations, the thresholds for antagonistic, additive, or synergistic effects were calculated as follows: TA=Fa+Fb(1−Fa), where Fa is the relative TGI (from 0 to 1) value at a given time point for the first drug and Fb is the relative TGI value at the same time point for the second drug. Variations within ±15% of the additive threshold are considered to be the result of additive drug interactions; combinations exerting <85% of the predicted additive effect are considered indifferent (and below 70%, antagonistic); combinations exerting >115% of the predicted threshold for additive effect synergistic.

Example 1: Breast Cancer Mouse Model

FVB-PyMT mice, used as a genetically engineered mouse model of breast cancer, were treated at the first appearance of tumor cell growth with nintedanib (FIG. 1). Upon reaching almost sacrifice size (10 weeks), the animal cohort was split in two; one cohort received nintedanib plus compound 5 (BIBF-BIBF+ME) and the other was treated with continued nintedanib (BIBF—BIBF) alone. Chronic exposure to nintedanib led to tumor cell resistance despite an initial delay in tumor growth, suggesting that the acquired resistance was characterized by a switch from a mainly glycolytic metabolism to a mostly mitochondrial metabolism. The animals treated with nintedanib+compound 5 experienced sustained tumor regression.

Example 2: Breast Cancer Mouse Model (nintedanib+Compound 5)

Figure 2:
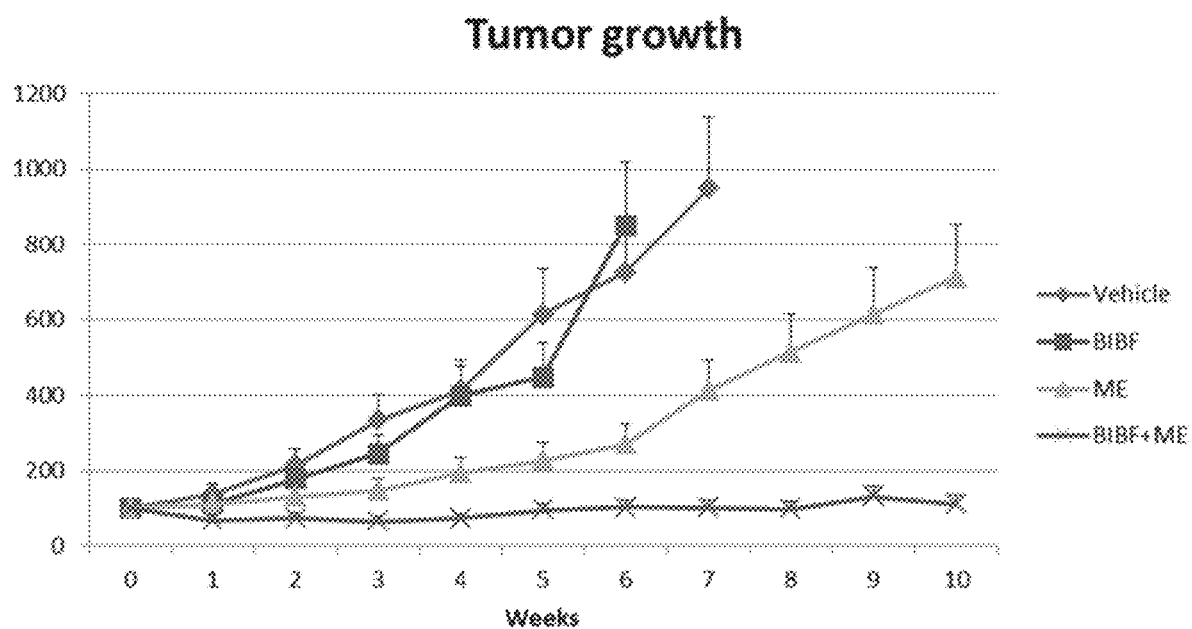
FIG. 2 depicts inhibition of tumor growth in a mouse model of breast cancer following treatment with vehicle, single agent treatment with nintedanib (BIBF), single agent treatment with compound 5 (ME), and combination treatment of nintedanib (BIBF) and compound 5 (ME).

FVB-PyMT mice were treated at the first appearance of tumor cell growth with vehicle, nintedanib (BIBF1120), compound 5 (ME) or the combination nintedanib+compound 5 (BIBF+ME). The animals treated with the combination of nintedanib+compound 5 experienced sustained tumor growth inhibition (FIG. 2).

Example 3: Breast Cancer Mouse Model (dovitinib+Compound 5)

Figure 3:
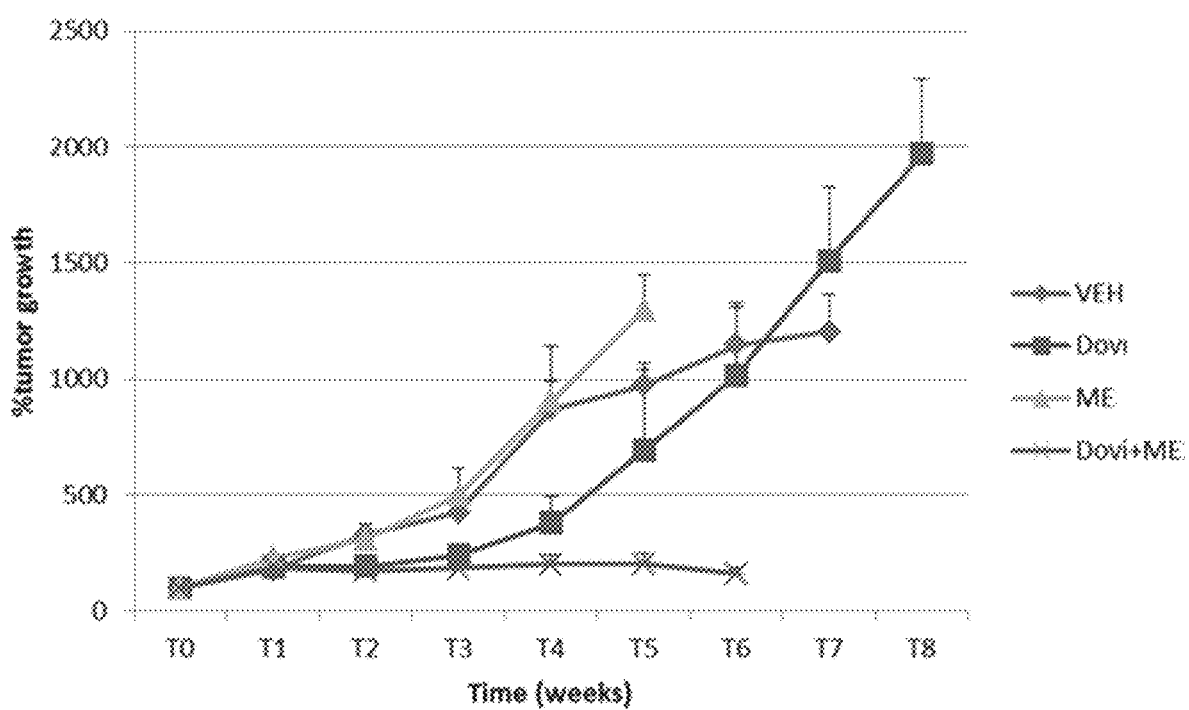
FIG. 3 depicts tumor growth in a mouse model of breast cancer following treatment with vehicle (VEH), single agent treatment with dovitinib (Dovi), single agent treatment with compound 5 (ME), and combination treatment of dovitinib (Dovi) and compound 5 (ME).

FVB-PyMT mice (model for breast cancer) were treated at the first appearance of tumor cell growth with vehicle, dovitinib (Dovi), compound 5 (ME) or the combination dovitinib+compound 5 (Dovi+ME). The animals treated with the combination of dovitinib+compound 5 experienced sustained tumor growth inhibition (FIG. 3).

Example 4: Breast Cancer Mouse Model (regorafenib+Compound 5)

Figure 4:
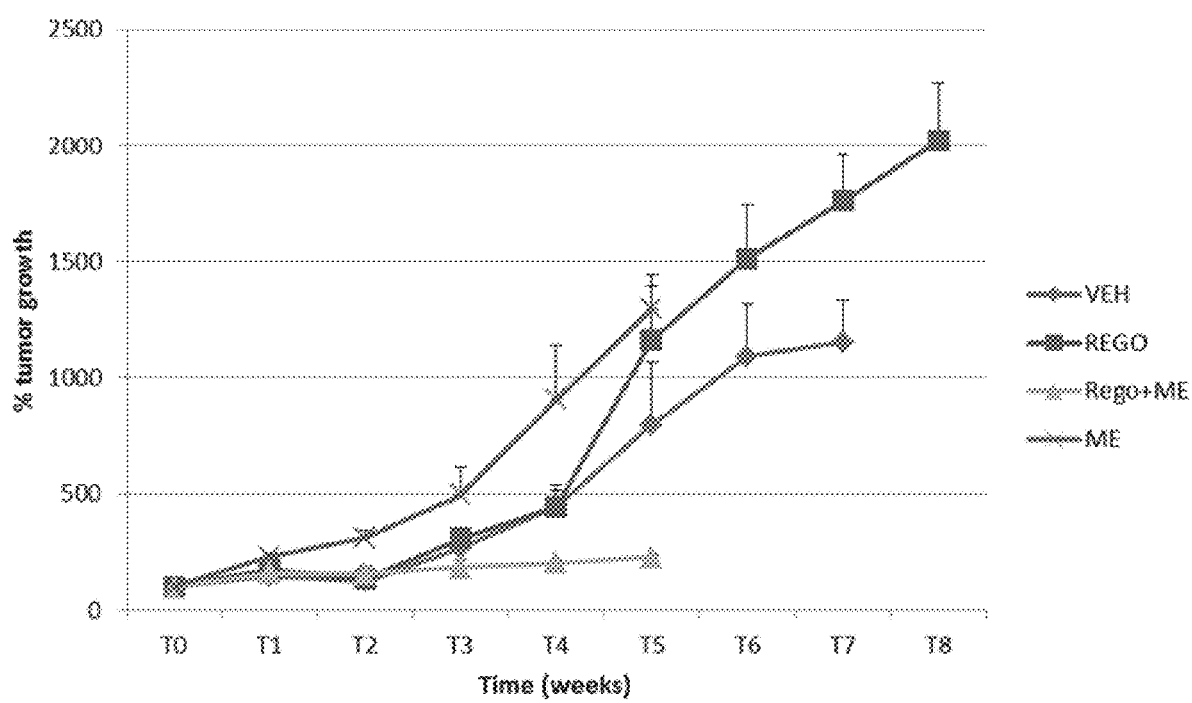
FIG. 4 depicts tumor growth in a mouse model of breast cancer following treatment with vehicle (VEH), single agent treatment of regorafenib (Rego), single agent treatment with compound 5 (ME), and combination treatment of regorafenib (Rego) and compound 5 (ME).

FVB-PyMT mice (model for breast cancer) were treated at the first appearance of tumor cell growth with vehicle, regorafenib (Rego), compound 5 (ME) or the combination regorafenib+compound 5 (Rego+ME). Regorafenib as a monotherapy lacked efficacy. The animals treated with the combination of regorafenib+compound 5 experienced sustained tumor growth inhibition (FIG. 4).

Example 5: Lune Cancer Mouse Model

Figure 5:
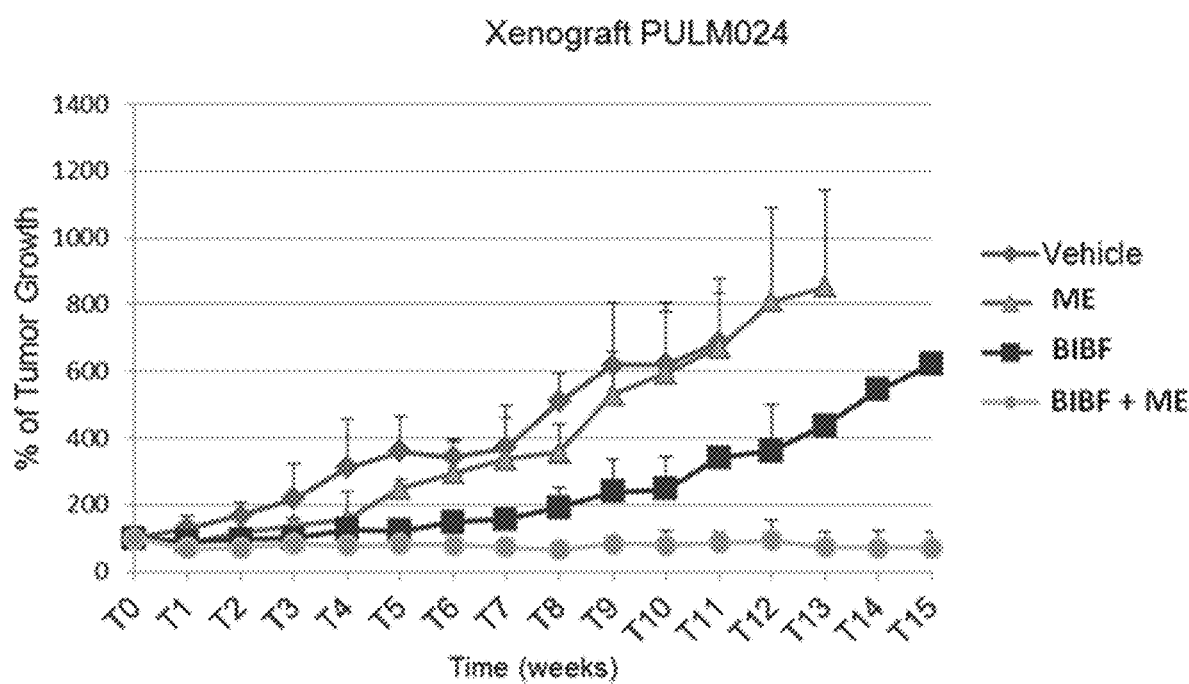
FIG. 5 depicts non-small cell lung cancer growth inhibition in a mouse xenograft model (PULM024) following treatment with Vehicle, single agent treatment with nintedanib (BIBF), single agent treatment with compound 5 (ME), and combination treatment of nintedanib (BIBF) and compound 5 (ME).

A mouse xenograft model (Pulm024) was used as a non-small cell lung cancer model. Pulm024 is a lung cancer patient-derived xenograft (PDX). This PDX is an adenocarcinoma of the lung, mutant for KRAS and wild type for EGFR, which represents the most frequent variant of lung cancer. Tumor growth inhibition analysis demonstrated that nintedanib alone was able to delay tumor growth, but the combination of nintedanib (BIBF) plus compound 5 (ME) completely abrogated tumor growth (FIG. 5).

Example 6: Lune Cancer Mouse Model

Figure 6:
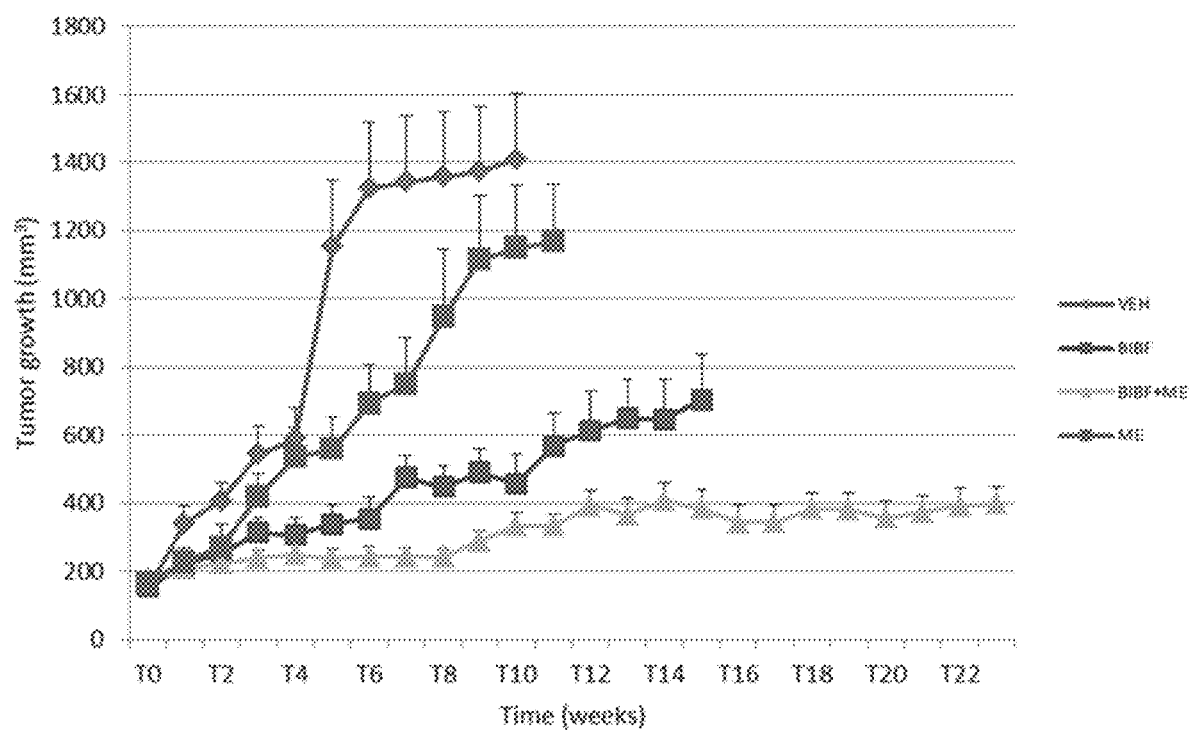
FIG. 6 depicts squamous cell lung cancer growth inhibition in a mouse xenograft model (ECB1) following treatment with vehicle (VEH), single agent treatment with nintedanib (BIBF), single agent treatment with compound 5 (ME), and combination treatment of nintedanib (BIBF) and compound 5 (ME).

A mouse xenograft model (ECB1) was used as a squamous cell lung cancer model. Tumor growth inhibition analysis was completed following single agent treatment of vehicle, nintedanib, and compound 5, and combination treatment of nintedanib and compound 5. Tumor growth inhibition analysis demonstrated that combination treatment of nintedanib and compound 5 significantly delayed tumor growth (FIG. 6).

Example 7: Combination Treatment for Ovarian Cancer

Human Clinical Trial of the Safety and/or Efficacy of Combination Treatment for Ovarian Cancer Objective: To compare the safety and pharmacokinetics of administration of compound 5 and nintedanib.

Study Design: This study will be a Phase I, single-center, open-label, randomized dose escalation study followed by a Phase II study in ovarian cancer patients. Patients should not have had exposure to compound 5 prior to the study entry. Patients must not have received treatment for their cancer within 2 weeks of beginning the trial. Treatments include the use of chemotherapy, hematopoietic growth factors, and biologic therapy such as monoclonal antibodies. Patients must have recovered from all toxicities (to grade 0 or 1) associated with previous treatment. All subjects are evaluated for safety and all blood collections for pharmacokinetic analysis are collected as scheduled. All studies are performed with institutional ethics committee approval and patient consent.

Phase I: Patients receive i.v. compound 5 (10 mg/kg) on days 1, 8, and 15 of each 28-day cycle. Doses of compound 5 may be held or modified for toxicity based on assessments as outlined below. Patients receive nintedanib (150 mg) orally (PO) twice daily (BID) on days 1-28. Courses repeat every 28 days in the absence of disease progression or unacceptable toxicity. Cohorts of 3-6 patients receive escalating doses of compound 5 and nintedanib until the maximum tolerated dose (MTD) for compound 5 and nintedanib is determined. The MTD is defined as the dose preceding that at which 2 of 3 or 2 of 6 patients experience dose-limiting toxicity. Dose limiting toxicities are determined according to the definitions and standards set by the National Cancer Institute (NCI) Common Terminology for Adverse Events (CTCAE) Version 3.0 (Aug. 9, 2006).

Phase II: Patients receive compound 5 and nintedanib as in phase I at the MTD determined in phase I. Treatment repeats every 4 weeks for 2-6 courses in the absence of disease progression or unacceptable toxicity. After completion of 2 courses of study therapy, patients who achieve a complete or partial response may receive an additional 4 courses. Patients who maintain stable disease for more than 2 months after completion of 6 courses of study therapy may receive an additional 6 courses at the time of disease progression, provided they meet original eligibility criteria.

Example 8: Combination Treatment for Small Cell Lung Cancer

Human Clinical Trial of the Safety and/or Efficacy of Combination Treatment for Small Cell Lung Cancer Objective: To compare the safety and pharmacokinetics of administering compound 5 and nintedanib.

Study Design: This study will be a Phase 1, single-center, open-label, randomized dose escalation study followed by a Phase II study in small cell lung cancer patients. Patients should not have had exposure to compound 5 prior to the study entry. Patients must not have received treatment for their cancer within 2 weeks of beginning the trial, with the exception of nintedanib. Treatments include the use of chemotherapy, hematopoietic growth factors, and biologic therapy such as monoclonal antibodies. Patients must have recovered from all toxicities (to grade 0 or 1) associated with previous treatment. All subjects are evaluated for safety and all blood collections for pharmacokinetic analysis are collected as scheduled. All studies are performed with institutional ethics committee approval and patient consent.

Phase I: Patients receive i.v. compound 5 (10 mg/kg) on days 1, 8, and 15 of each 28-day cycle. Doses of compound 5 may be held or modified for toxicity based on assessments as outlined below. Patients receive nintedanib (150 mg) orally (PO) twice daily (BID) on days 1-28. Courses repeat every 28 days in the absence of disease progression or unacceptable toxicity. Cohorts of 3-6 patients receive escalating doses of compound 5 and nintedanib until the maximum tolerated dose (MTD) for compound 5 and nintedanib is determined. The MTD is defined as the dose preceding that at which 2 of 3 or 2 of 6 patients experience dose-limiting toxicity. Dose limiting toxicities are determined according to the definitions and standards set by the National Cancer Institute (NCI) Common Terminology for Adverse Events (CTCAE) Version 3.0 (Aug. 9, 2006).

Phase II: Patients receive compound 5 and nintedanib as in phase I at the MTD determined in phase I. Treatment repeats every 4 weeks for 2-6 courses in the absence of disease progression or unacceptable toxicity. After completion of 2 courses of study therapy, patients who achieve a complete or partial response may receive an additional 4 courses. Patients who maintain stable disease for more than 2 months after completion of 6 courses of study therapy may receive an additional 6 courses at the time of disease progression, provided they meet original eligibility criteria.

Example 9: Combination Treatment for Breast Cancer

Human Clinical Trial of the Safety and Efficacy of Compound 5 and Nintedanib for Treatment of Breast Cancer Study Design: This study will be a Phase II study in breast cancer patients. Patients must not have received treatment for their cancer within 2 weeks of beginning the trial. Treatments include the use of chemotherapy, hematopoietic growth factors, and biologic therapy such as monoclonal antibodies. Patients must have recovered from all toxicities (to grade 0 or 1) associated with previous treatment. All subjects are evaluated for safety and all blood collections for pharmacokinetic analysis are collected as scheduled. All studies are performed with institutional ethics committee approval and patient consent.

Phase II: Patients receive i.v. compound 5 (10 mg/kg) on days 1, 8, and 15 of each 28-day cycle. Patients receive nintedanib (150 mg) orally (PO) twice daily (BID) on days 1-28. Treatment repeats every 4 weeks for 2-6 courses in the absence of disease progression or unacceptable toxicity. After completion of 2 courses of study therapy, patients who achieve a complete or partial response may receive an additional 4 courses. Patients who maintain stable disease for more than 2 months after completion of 6 courses of study therapy may receive an additional 6 courses at the time of disease progression, provided they meet original eligibility criteria.

Blood Sampling Serial blood is drawn by direct vein puncture before and after administration of compound 5. Venous blood samples (5 mL) for determination of serum concentrations are obtained at about 10 minutes prior to dosing and at approximately the following times after dosing: days 1, 8, 15, and 22. Each serum sample is divided into two aliquots. All serum samples are stored at −2° C. Serum samples are shipped on dry ice.

Pharmacokinetics: Patients undergo plasma/serum sample collection for pharmacokinetic evaluation before beginning treatment and at days 1, 8, 15, and 22. Pharmacokinetic parameters are calculated by model independent methods on a Digital Equipment Corporation VAX 8600 computer system using the latest version of the BIOAVL software. The following pharmacokinetics parameters are determined: peak serum concentration ($C_{max}$); time to peak serum concentration ($t_{max}$); area under the concentration-time curve (AUC) from time zero to the last blood sampling time ($AUC_{0-72}$) calculated with the use of the linear trapezoidal rule, and terminal elimination half-life ($t_{1/2}$), computed from the elimination rate constant. The elimination rate constant is estimated by linear regression of consecutive data points in the terminal linear region of the log-linear concentration-time plot. The mean, standard deviation (SD), and coefficient of variation (CV) of the pharmacokinetic parameters are calculated for each treatment. The ratio of the parameter means (preserved formulation/non-preserved formulation) is calculated.

Patient Response to combination therapy: Patient response is assessed via imaging with X-ray, CT scans, MRI, and imaging is performed prior to beginning the study and at the end of the first cycle, with additional imaging performed every four weeks or at the end of subsequent cycles. Imaging modalities are chosen based upon the cancer type and feasibility/availability, and the same imaging modality is utilized for similar cancer types as well as throughout each patient's study course. Response rates are determined using the RECIST criteria. (Therasse et al, J. Natl. Cancer Inst. 2000 Feb. 2; 92(3):205-16; http://ctep.cancer.gov/forms/TherasseRECISTJNCI.pdf). Patients also undergo cancer/tumor biopsy to assess changes in progenitor cancer cell phenotype and clonogenic growth by flow cytometry, Western blotting, and IHC, and for changes in cytogenetics by FISH. After completion of study treatment, patients are followed periodically for 4 weeks.

Example 10: Combination Treatment for Ovarian Cancer

Human Clinical Trial of the Safety and/or Efficacy of Combination Treatment for Ovarian Lung Cancer Objective: To compare the safety and pharmacokinetics of administering Trilexium™ and nintedanib.

Study Design: This study will be a Phase I, single-center, open-label, randomized dose escalation study followed by a Phase II study in small cell lung cancer patients. Patients should not have had exposure to Trilexium™ prior to the study entry. Patients must not have received treatment for their cancer within 2 weeks of beginning the trial, with the exception of nintedanib. Treatments include the use of chemotherapy, hematopoietic growth factors, and biologic therapy such as monoclonal antibodies. Patients must have recovered from all toxicities (to grade 0 or 1) associated with previous treatment. All subjects are evaluated for safety and all blood collections for pharmacokinetic analysis are collected as scheduled. All studies are performed with institutional ethics committee approval and patient consent.

Phase I: Patients receive Trilexium™ on days 1, 8, and 15 of each 28-day cycle injected intraperitoneally in their abdominal cavity. Doses of Trilexium™ may be held or modified for toxicity based on assessments as outlined below. Patients receive nintedanib (150 mg) orally (PO) twice daily (BID) on days 1-28. Courses repeat every 28 days in the absence of disease progression or unacceptable toxicity. Cohorts of 3-6 patients receive escalating doses of Trilexium™ and nintedanib until the maximum tolerated dose (MTD) for Trilexium™ and nintedanib is determined. The MTD is defined as the dose preceding that at which 2 of 3 or 2 of 6 patients experience dose-limiting toxicity. Dose limiting toxicities are determined according to the definitions and standards set by the National Cancer Institute (NCI) Common Terminology for Adverse Events (CTCAE) Version 3.0 (Aug. 9, 2006).

Phase II: Patients receive Trilexium™ and nintedanib as in phase I at the MTD determined in phase I. Treatment repeats every 4 weeks for 2-6 courses in the absence of disease progression or unacceptable toxicity. After completion of 2 courses of study therapy, patients who achieve a complete or partial response may receive an additional 4 courses. Patients who maintain stable disease for more than 2 months after completion of 6 courses of study therapy may receive an additional 6 courses at the time of disease progression, provided they meet original eligibility criteria.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

Example 11: Combination Treatment for Renal Cell Carcinoma

Human Clinical Trial of the Safety and Efficacy of Compound 5 and sorafenib (Nexavar) for Treatment of Renal Cell Carcinoma Study Design: This study will be a Phase II study in renal cell carcinoma patients. Patients must have recovered from all toxicities (to grade 0 or 1) associated with previous treatment. All subjects are evaluated for safety and all blood collections for pharmacokinetic analysis are collected as scheduled. All studies are performed with institutional ethics committee approval and patient consent.

Phase II: Patients receive i.v. compound 5 (10 mg/kg) on days 1, 8, and 15 of each 28-day cycle. Patients receive 400 mg sorafenib (two 200 mg tablets) orally (PO) twice daily (BID) either one hour before or two hours after meals on days 1-28. Treatment repeats every 4 weeks for 2-6 courses in the absence of disease progression or unacceptable toxicity. After completion of 2 courses of study therapy, patients who achieve a complete or partial response may receive an additional 4 courses. Patients who maintain stable disease for more than 2 months after completion of 6 courses of study therapy may receive an additional 6 courses at the time of disease progression, provided they meet original eligibility criteria.

Example 12: Combination Treatment for Liver Carcinoma

Human Clinical Trial of the Safety and Efficacy of Compound 5 and sorafenib (Nexavar) for Treatment of Liver Carcinoma Study Design: This study will be a Phase II study in liver carcinoma patients. Patients must have recovered from all toxicities (to grade 0 or 1) associated with previous treatment. All subjects are evaluated for safety and all blood collections for pharmacokinetic analysis are collected as scheduled. All studies are performed with institutional ethics committee approval and patient consent.

Phase II: Patients receive i.v. compound 5 (10 mg/kg) on days 1, 8, and 15 of each 28-day cycle. Patients receive 400 mg sorafenib (two 200 mg tablets) orally (PO) twice daily (BID) either one hour before or two hours after meals on days 1-28. Treatment repeats every 4 weeks for 2-6 courses in the absence of disease progression or unacceptable toxicity. After completion of 2 courses of study therapy, patients who achieve a complete or partial response may receive an additional 4 courses. Patients who maintain stable disease for more than 2 months after completion of 6 courses of study therapy may receive an additional 6 courses at the time of disease progression, provided they meet original eligibility criteria.

Example 13: Combination Treatment for Ovarian Cancer

Human Clinical Trial of the Safety and/or Efficacy of Combination Treatment for Ovarian Cancer Objective: To compare the safety and pharmacokinetics of administration of compound 5 and dovitinib.

Study Design: This study will be a Phase I, single-center, open-label, randomized dose escalation study followed by a Phase II study in ovarian cancer patients. Patients should not have had exposure to compound 5 prior to the study entry. Patients must not have received treatment for their cancer within 2 weeks of beginning the trial. Treatments include the use of chemotherapy, hematopoietic growth factors, and biologic therapy such as monoclonal antibodies. Patients must have recovered from all toxicities (to grade 0 or 1) associated with previous treatment. All subjects are evaluated for safety and all blood collections for pharmacokinetic analysis are collected as scheduled. All studies are performed with institutional ethics committee approval and patient consent.

Phase I: Patients receive i.v. compound 5 (10 mg/kg) on days 1, 8, and 15 of each 28-day cycle. Doses of compound 5 may be held or modified for toxicity based on assessments as outlined below. Patients receive dovitinib (500 mg/kg) orally (PO) 5 days on and 2 days off in 28 day cycles. Courses repeat every 28 days in the absence of disease progression or unacceptable toxicity. Cohorts of 3-6 patients receive escalating doses of compound 5 and dovitinib until the maximum tolerated dose (MTD) for compound 5 and dovitinib is determined. The MTD is defined as the dose preceding that at which 2 of 3 or 2 of 6 patients experience dose-limiting toxicity. Dose limiting toxicities are determined according to the definitions and standards set by the National Cancer Institute (NCI) Common Terminology for Adverse Events (CTCAE) Version 3.0 (Aug. 9, 2006).

Phase II: Patients receive compound 5 and dovitinib as in phase I at the MTD determined in phase I. Treatment repeats every 4 weeks for 2-6 courses in the absence of disease progression or unacceptable toxicity. After completion of 2 courses of study therapy, patients who achieve a complete or partial response may receive an additional 4 courses. Patients who maintain stable disease for more than 2 months after completion of 6 courses of study therapy may receive an additional 6 courses at the time of disease progression, provided they meet original eligibility criteria.

Example 14: Combination Treatment for Breast Cancer

Human Clinical Trial of the Safety and Efficacy of Compound 5 and dovitinib for Treatment of Breast Cancer Study Design: This study will be a Phase II study in breast cancer patients. Patients must not have received treatment for their cancer within 2 weeks of beginning the trial. Treatments include the use of chemotherapy, hematopoietic growth factors, and biologic therapy such as monoclonal antibodies. Patients must have recovered from all toxicities (to grade 0 or 1) associated with previous treatment. All subjects are evaluated for safety and all blood collections for pharmacokinetic analysis are collected as scheduled. All studies are performed with institutional ethics committee approval and patient consent.

Phase II: Patients receive i.v. compound 5 (10 mg/kg) on days 1, 8, and 15 of each 28-day cycle. Patients receive dovitinib (500 mg/kg) orally (PO) 5 days on and 2 days off in 28 day cycles. Treatment repeats every 4 weeks for 2-6 courses in the absence of disease progression or unacceptable toxicity. After completion of 2 courses of study therapy, patients who achieve a complete or partial response may receive an additional 4 courses. Patients who maintain stable disease for more than 2 months after completion of 6 courses of study therapy may receive an additional 6 courses at the time of disease progression, provided they meet original eligibility criteria.

Blood Sampling Serial blood is drawn by direct vein puncture before and after administration of compound 5. Venous blood samples (5 mL) for determination of serum concentrations are obtained at about 10 minutes prior to dosing and at approximately the following times after dosing: days 1, 8, 15, and 22. Each serum sample is divided into two aliquots. All serum samples are stored at −20° C. Serum samples are shipped on dry ice.

Pharmacokinetics: Patients undergo plasma/serum sample collection for pharmacokinetic evaluation before beginning treatment and at days 1, 8, 15, and 22. Pharmacokinetic parameters are calculated by model independent methods on a Digital Equipment Corporation VAX 8600 computer system using the latest version of the BIOAVL software. The following pharmacokinetics parameters are determined: peak serum concentration ($C_{max}$); time to peak serum concentration ($t_{max}$) area under the concentration-time curve (AUC) from time zero to the last blood sampling time ($AUC_{0-72}$) calculated with the use of the linear trapezoidal rule; and terminal elimination half-life ($t_{1/2}$), computed from the elimination rate constant. The elimination rate constant is estimated by linear regression of consecutive data points in the terminal linear region of the log-linear concentration-time plot. The mean, standard deviation (SD), and coefficient of variation (CV) of the pharmacokinetic parameters are calculated for each treatment. The ratio of the parameter means (preserved formulation/non-preserved formulation) is calculated.

Patient Response to combination therapy: Patient response is assessed via imaging with X-ray, CT scans, MRI, and imaging is performed prior to beginning the study and at the end of the first cycle, with additional imaging performed every four weeks or at the end of subsequent cycles. Imaging modalities are chosen based upon the cancer type and feasibility/availability, and the same imaging modality is utilized for similar cancer types as well as throughout each patient's study course. Response rates are determined using the RECIST criteria. (Therasse et al, J. Natl. Cancer Inst. 2000 Feb. 2; 92(3):205-16; http://ctep.cancer.gov/forms/TherasseRECISTJNC1.pdf). Patients also undergo cancer/tumor biopsy to assess changes in progenitor cancer cell phenotype and clonogenic growth by flow cytometry, Western blotting, and IHC, and for changes in cytogenetics by FISH. After completion of study treatment, patients are followed periodically for 4 weeks.

What is claimed is:

1. A method of treating a cancer that is prostate cancer, pancreatic cancer, leukemia, lymphoma, ovarian cancer, neuroblastoma, glioblastoma, kidney cancer, bladder cancer, gastrointestinal stromal tumors, liver cancer, head and neck cancer, lung cancer, melanoma, or a hematological malignancy, comprising administering to a subject in need thereof an effective amount of
   (i) an angiogenesis inhibitor; and
   (ii) 3-(4-hydroxyphenyl)-4-(4-hydroxyphenyl)-8-methylchroman-7-ol (compound 5).

2. The method of claim 1, wherein the angiogenesis inhibitor is nintedanib, bevacizumab, sorafenib, sunitinib, thalidomide, dovitinib, regorafenib, or imatinib.

3. The method of claim 1, wherein the angiogenesis inhibitor is nintedanib.

4. The method of claim 1, wherein the angiogenesis inhibitor is bevacizumab.

5. The method of claim 1, wherein the cancer is ovarian cancer, kidney cancer, liver cancer, or lung cancer.

6. The method of claim 1, wherein the cancer is lung cancer.

7. The method of claim 1, wherein the cancer is refractory, non-responsive, or resistant to chemotherapy and/or haploidentical stem cell transplantation.

8. The method of claim 7, wherein the cancer is non-responsive or resistant to the angiogenesis inhibitor.

9. The method of claim 1, wherein the angiogenesis inhibitor and 3-(4-hydroxyphenyl)-4-(4-hydroxyphenyl)-8-methylchroman-7-ol (compound 5) are administered simultaneously or sequentially.

10. A method of treating a chemoresistant cancer that is prostate cancer, pancreatic cancer, leukemia, lymphoma, ovarian cancer, neuroblastoma, glioblastoma, kidney cancer, bladder cancer, gastrointestinal stromal tumors, liver cancer, head and neck cancer, lung cancer, melanoma, or a hematological malignancy, comprising administering to a subject in need thereof an effective amount of
   (i) an angiogenesis inhibitor; and
   (ii) 3-(4-hydroxyphenyl)-4-(4-hydroxyphenyl)-8-methylchroman-7-ol (compound 5).

11. The method of claim 10, wherein the chemoresistant cancer is ovarian cancer, kidney cancer, liver cancer, or lung cancer.

12. The method of claim 10, wherein the chemoresistant cancer is resistant to the angiogenesis inhibitor.

13. The method of claim 10, wherein the angiogenesis inhibitor is nintedanib.

* * * * *